(12) United States Patent
Tilseth et al.

(10) Patent No.: US 8,372,812 B2
(45) Date of Patent: Feb. 12, 2013

(54) PHOSPHOLIPID AND PROTEIN TABLETS

(75) Inventors: Snorre Tilseth, Bergen (NO); Nils Hoem, Oslo (NO)

(73) Assignee: Aker Biomarine ASA, Oslo (NO)

( * ) Notice: Subject to any disclaimer, the term of this patent is extended or adjusted under 35 U.S.C. 154(b) by 362 days.

(21) Appl. No.: 12/711,822

(22) Filed: Feb. 24, 2010

(65) Prior Publication Data

US 2010/0227792 A1 Sep. 9, 2010

Related U.S. Application Data

(60) Provisional application No. 61/155,758, filed on Feb. 26, 2009.

(51) Int. Cl.
   *A61K 38/17*   (2006.01)
   *A61K 31/01*   (2006.01)
   *A61K 9/20*    (2006.01)
   *A61K 9/38*    (2006.01)
   *A61K 9/42*    (2006.01)

(52) U.S. Cl. ............... 514/21.92; 514/762; 424/464; 424/476; 424/477

(58) Field of Classification Search .......... None
See application file for complete search history.

(56) References Cited

U.S. PATENT DOCUMENTS

| | | | |
|---|---|---|---|
| 4,119,619 | A | 10/1978 | Rogozhin et al. |
| 5,266,564 | A | 11/1993 | Modelell et al. |
| 5,434,183 | A | 7/1995 | Larsson-Backstrom |
| 6,537,787 | B1 | 3/2003 | Breton |
| 6,800,299 | B1 | 10/2004 | Beaudoin et al. |
| 2003/0044495 | A1 | 3/2003 | Kagan et al. |
| 2004/0241249 | A1 | 12/2004 | Sampalis |

FOREIGN PATENT DOCUMENTS

| | | |
|---|---|---|
| BR | 8701265 | 3/1987 |
| CA | 1098900 | 4/1981 |
| EP | 0609078 | 8/1994 |
| EP | 670306 | 6/1995 |
| EP | 1127497 | 8/2001 |
| EP | 1392623 | 3/2004 |
| EP | 1406641 | 4/2004 |
| EP | 1542670 | 6/2005 |
| EP | 0973532 | 9/2005 |
| EP | 1660071 | 5/2006 |
| EP | 1689413 | 8/2006 |
| EP | 1743531 | 1/2007 |
| EP | 1631280 | 3/2008 |
| EP | 1123368 | 4/2008 |
| EP | 1406641 | 1/2009 |
| EP | 1419768 | 1/2009 |
| EP | 1292294 | 3/2009 |
| EP | 1706106 | 7/2009 |
| EP | 1385500 | 7/2010 |
| GB | 2097014 | 10/1982 |
| GB | 921537 | 6/1999 |
| JP | 61281159 | 12/1986 |
| JP | 02049091 | 2/1990 |
| JP | 2215351 | 8/1990 |
| JP | 4012665 | 1/1992 |
| JP | 2963152 | 2/1992 |
| JP | 3081692 | 7/1994 |
| JP | 2524217 | 8/1996 |
| JP | 3344887 | 7/1997 |
| JP | 3611222 | 8/1997 |
| JP | 2001-158736 A | 6/2001 |
| JP | 2003-003192 A | 1/2003 |
| JP | 2003-048831 A | 2/2003 |
| JP | 2003-146883 A | 5/2003 |
| JP | 3467794 | 9/2003 |
| JP | 2003-531857 A | 10/2003 |
| JP | 3486778 | 10/2003 |
| JP | 2004-525180 A | 8/2004 |
| JP | 2004-536059 A | 12/2004 |
| JP | 3678317 | 5/2005 |
| JP | 2005-245379 A | 9/2005 |
| JP | 2006-502196 A | 1/2006 |
| JP | 2006-069948 A | 3/2006 |
| JP | 2006-083136 A | 3/2006 |
| JP | 2006-290784 A | 10/2006 |
| JP | 2006-316073 A | 11/2006 |
| JP | 2006-328014 A | 12/2006 |
| JP | 2006-528233 A | 12/2006 |
| JP | 2007-502805 A | 2/2007 |
| JP | 2007-509131 A | 4/2007 |
| JP | 2007-126455 A | 5/2007 |
| JP | 2007-518764 A | 7/2007 |
| JP | 2007-246404 A | 9/2007 |
| SU | 220741 | 1/1971 |
| WO | 86/06082 | 10/1986 |
| WO | 90/05765 | 5/1990 |
| WO | 93/24142 | 12/1993 |
| WO | 97/38585 | 10/1997 |

(Continued)

OTHER PUBLICATIONS

Dave "Overview of pharmaceutical excipients used in tablets and capsules," Drug Topics, Oct. 24, 2008.*
Takaichi et al., 2003, "Fatty Acids of astaxanthin esters in krill determined by mild mass spectrometry", Comparative Biochemistry and Physiology Part B, Biochemistry and Molecular Biology, Elsevier, Oxford, vol. 136, Jan. 1, 2003, p. 317-322.
Tanaka et al., 2004, "Extraction of Phospholipids from Salmon Roe with Supercritical Carbon Dioxide and an Entrainer", J. Oleo Sci, 53(9): 417-424.
Tanaka et al., 2005, "Extraction of Phospholipids from Unused Natrual Resources with Supercritical Carbon Dioxide and an Entrainer", Journal of Oleo Science, vol. 54(11): 569-576.
Todoric et al., 2006, "Adipose tissue inflammation induced by high-fat diet in obese diabetic mice is prevented by n-3 polyunsaturated fatty acids", Diabetologia, 49(9): 2109-2119.
Tou et al., 2007, "Krill for human consumption: nutritional value and potential health benefits.", Nutrition Rev 65 (2):63-77.

(Continued)

*Primary Examiner* — Christina Bradley
(74) *Attorney, Agent, or Firm* — Casimir Jones SC

(57) ABSTRACT

A new method for krill meal production has been developed using a two step cooking process. In the first step the proteins and phospholipids are removed from the krill and precipitated as a coagulum. In the second stage the krill without phospholipids are cooked. Following this, residual fat and astaxanthin are removed from the krill using mechanical separation methods. A novel krill meal product with superior nutritional and technical properties is prepared.

16 Claims, 7 Drawing Sheets

FOREIGN PATENT DOCUMENTS

| | | |
|---|---|---|
| WO | 97/39759 | 10/1997 |
| WO | 98/34498 | 8/1998 |
| WO | 99/39589 | 8/1999 |
| WO | 00/23546 | 4/2000 |
| WO | 00/25608 | 5/2000 |
| WO | 00/38708 | 7/2000 |
| WO | 01/28526 | 4/2001 |
| WO | 01/82928 | 11/2001 |
| WO | 02/083122 | 10/2002 |
| WO | 02/092540 | 11/2002 |
| WO | 02/102394 | 12/2002 |
| WO | 03/011873 | 2/2003 |
| WO | 03/013497 | 2/2003 |
| WO | 2004/028529 | 4/2004 |
| WO | 2004/047554 | 6/2004 |
| WO | 2004/100943 | 11/2004 |
| WO | 2005/004393 | 1/2005 |
| WO | 2005/018632 | 3/2005 |
| WO | 2005/037848 | 4/2005 |
| WO | 2005/038037 | 4/2005 |
| WO | 2005/070411 | 8/2005 |
| WO | 2006/030552 | 3/2006 |
| WO | 2007/080514 | 7/2007 |
| WO | 2007/080515 | 7/2007 |
| WO | 2007/108702 | 9/2007 |
| WO | 2008/006607 | 1/2008 |
| WO | 2008/117062 | 10/2008 |
| WO | 2009/027692 | 3/2009 |

OTHER PUBLICATIONS

Trayhurn et al., 2004, "Adipokines: inflammation and the pleiotropic role of white adipose tissue", Br. J. Nutrition, 92(3): 347-355.
Trebble et al., 2003, "Inhibition of tumour necrosis factor-alpha and interleukin 6 production by mononuclear cells following dietary fish-oil supplementation in healthy men and response to antioxidant co-supplementation", Br. J. Nutrition, 90(2): 405-412.
Ukkola et al., 2002, "Adiponectin: a link between excess adiposity and associated comorbidities?", J. Mol. Med., 80 (11): 696-702.
Van Der Veen et al., 1971 "The Lipids of Krill (*Euphausia* Species) and Red Crab (*Pleuroncodes planipes*)", Lipids, 6(7): 481-485.
Virtue, et al. 1996, Reproductive trade-off in male Antarctic krill, *Euphausia superba*, Marine Biology, vol. 126, No. 3, pp. 521-527.
Yamaguchi et al., 1983, "The Composition of Carotenoid Pigments in the Antarctic Krill *Euphausia superba*", Bulletin of the Japanese Society of Scientific Fisheries, 49(9): 1411-1415.
Yamaguchi et al., 1986, "Supercritical Carbon Dioxide Extraction of Oils From Antarctic Krill," Journal of Agricultural and Food Chemistry, vol. 34, pp. 904-907.
Yanase M; 1974, "Modification of a Russian method for separation of heat-coagulated protein from Antarctic krill", Database FSTA (online); International Food Information Service (IFIS); Frankfurt-Main, DE.
Yen et al., 1994, "Effect of dietary omega-3 and omega-6 fatty acid sources on PUVA-induced cutaneous toxicity and tumorogenesis in the hairless mouse", Arch. Dermatol, Res., 286(6): 331-6.
Database WPI Week 200682, Thomson Scientific, London, GB, 2006.
English Abstract; JP 2003-531857; See abstract from corresponding WO 2001/082928 filed herewith.
English Abstract; JP 2004-525180; See abstract from corresponding WO 2002/083122 filed herewith.
English Abstract; JP 2006-528233; See abstract from corresponding WO 2004/100943 filed herewith.
English Abstract; JP 2007-502805; See abstract from corresponding WO 2005/018632 filed herewith.
English Abstract; JP 2007-509131; See abstract from corresponding WO 2005/037848 filed herewith.
English Abstract; JP 2007-518764; See abstract from corresponding WO 2005/070411 filed herewith.
English Abstract; JP 2004-536059; See abstract from corresponding WO 2002/09254 filed herewith.
English Abstract; JP 2006-502196; See abstract from corresponding WO 2004/028529 filed herewith.

Ando and Hatano, 1988, "Isolation of apolipoproteins from carotenoid-carrying lipoprotein in the serum of chum salmon, *Oncorhynchus keta*", J. Lipid Research, 29: 1264-1271.
Aoi et al., 2003, "Astaxanthin limits exercise-induced skeletal and cardiac muscle damage in mice", Antioxidants & Redox Signaling, 5(1): 139-44.
Britton, 1985, "General Carotenoid Methods", Methods in Enzymology, vol. 111, pp. 113-149.
Calder, 2006, "n-3 polyunsaturated fatty acids, inflammation, and inflammatory diseases", Am. J. Clin. Nutr., 83: 1505S.
Charest et al., 2001, "Astaxanthin Extraction from Crawfish Shells by Supercritical CO2 with Ethanol as Cosolvent", J. Aquatic Food Product Technology, 10(3): 79-93.
Chen and Meyers, 1982, "Extraction of Astaxanthin Pigment from Crawfish Waste Using a Soy Oil Process", J. Food Sci., 47: 892-896.
Clarke, 1980, "The Biochemical Composition of Krill, *Euphausia superba* dana,from South Georgia", J. Exp. Mar. Biol. Ecol., 43: 221-236.
Czeczuga, 1974, "Comparative Studies of Carotenoids in the Fauna of the Gullmar Fjord (Bohuslan, Sweden). II. Crustacea: *Eupagurus bernhardus*, *Hyas coarctatus* and *Upogebia deltaura*", Marine Biology, 28: 95-98.
De Ritter and Purcell, 1981, "Carotenoid Analytical Methods", Carotenoids as Colorants and Vitamin A Precursors: Technological and Nutritional Applications, pp. 815-882.
Deutch, 1995, "Menstrual pain in Danish women correlated with low n-3 polyunsaturated fatty acid intake", Eur. J. Clin. Nutr., 49(7): 508-16.
Diez et al., 2003, "The role of the novel adipocyte-derived hormone adiponectin in human disease", Eur. J. Endocrinol., 148(3): 293-300.
Ellingsen et al., 1987, "Biochemistry of the autolytic processes in Antarctic krill post mortem. Autoproteolysis." Biochem. J. 246, 295-305.
Emodi, 1978, "Carotenoids: Properties and Applications", Food Technology, 32(5): 38.
Felix-Valenzuela et al., 2001, "Supercritical CO2/Ethanol Extraction of Astaxanthin from Blue Crab (*Callinectes sapidus*) Shell Waste", Journal of Food Process Engineering, 24: 101-112.
Fox and Scheer, 1941, "Comparative Studies of the Pigments of Some Pacific Coast Echinoderms", The Biological Bulletin, 441-455.
Fricke, et al., 1984, "Lipid, Sterol and Fatty Acid Composition of Antarctic Krill (*Euphausia superba* Dana)", Lipids, 19 (11): 821-827.
Geusens et al., 1994, "Long-term effect of omega-3 fatty acid supplementation in active rheumatoid arthritis. A 12-month, double-blind, controlled study", Arthritis Rheum., 37(6): 824-9.
Gilchrist and Green, 1960, "The Pigments of Artemia", Proceedings of the Royal Society, Series B Biological Sciences, vol. 152 No. 946, pp. 118-136.
Goodwin and Srisukh, 1949, "Some Observations on Astaxanthin Distribution in Marine Crustacea", Department of Biochemistry, University of Liverpool, pp. 268-270.
Gulyaev and Bugrova, 1976 "Removing fats from the protein paste Okean". Konservnaya I Ovoshchesushil'naya Promyshlennost, (4), 37-8.
Hardardottir and Kinsella, 1988, "Extraction of Lipid and Cholesterol from Fish Muscle with Supercritical Fluids" Journal of Food Science, 53(6): 1656-1658.
International Aqua Feed, 2006, vol. 9.
International Search Report and Written Opinion for PCT/GB2008/002934, Dated Mar. 11, 2009.
International Search Report and Written Opinion for PCT/IB2010/000512; dated Jun. 24, 2010.
International Search Report for PCT/IB2007/000098, dated: Jun. 26, 2007.
Itoh et al., 2007; "Increased adiponectin secretion by highly purified eicosapentaenoic acid in rodent models of obesity and human obese subjects", Arteriosclerosis, Thrombosis, and Vascular Biology; 27(9): 1918-1925.
Johnson et al., 1978, "Simple Method for the Isolation of Astaxanthin from the Basidiomycetous Yeast *Phaffia rhodozyma*", Applied and Environmental Microbiology, 35(6): 1155-1159.

Kolakowska, 1989, "Krill lipids after frozen storage of about one year in relation to storage time before freezing", Die Nahrung Food, 33(3): 241-244.

Kris-Etherton et al., 2002, "Fish Consumption, Fish Oil, Omega-3 Fatty Acids, and Cardiovascular Disease", Circulation, 106:2747-2757.

Kristensen et al., 1989, "Dietary supplementation with n-3 polyunsaturated fatty acids and human platelet function: a review with particular emphasis on implications for cardiovascular disease", J. Intern. Med. Suppl. 731:141-50.

Kunesova et al., 2006, "The influence of n-3 polyunsaturated fatty acids and very low calorie diet during a short-term weight reducing regimen on weight loss and serum fatty acid composition in severely obese women", Physiol Res.; 55 (1):63-72.

Laight et al., 1999, "F2-isoprostane evidence of oxidant stress in the insulin resistant, obese Zucker rat: effects of vitamin E", Eur. J. Pharmacol. 377(1): 89-92.

Lambertson and Braekkan, 1971, "Method of Analysis of Astaxanthin and its Occurrence in some Marine Products," J. Sci. Food. Agr., vol. 22(2): 99-101.

Libby et al., 2006, "Inflammation and Atherothrombosis: From Population Biology and Bench Research to Clinical Practice", J. Amer. Coll. Card., 48 (9, Suppl. A): A33-A46.

Lopez et al., 2004, "Selective extraction of astaxanthin from crustaceans by use of supercritical carbon dioxide", Talanta, 64: 726-731.

Mandeville, 1991, "Isolation and Identification of Carotenoid Pigments, Lipids and Flavor Active Components from Raw Commercial Shrimp Waste", Food Biotechnology, 5(2): 185-195.

Meyers and Bligh, 1981, "Characterization of Astaxanthin Pigments from Heat-Processed Crawfish Waste", J. Agric. Food Chem., 29: 505-508.

Meyers, 1977, "Using Crustacean Meals and Carotenoid-Fortified Diets", Feedstuffs, vol. 49(19).

Meyers, 1994, "Developments in world aquaculture, feed formulations, and role of carotenoids", Pure & Appl. Chem, vol. 66(5): 1069-1076.

Mills et al., 1989, "Dietary N-6 and N-3 fatty acids and salt-induced hypertension in the borderline hypertensive rat", Lipids, 24(1): 17-24.

Moates and Van Bentem, 1990, "Separating out the value", Food Science and Technology Today, 4(4): 213-214.

Nikolaeva, 1967 "Amino acid composition of protein-coagulate in krill", VNIRO, 63:161-4.

Phleger, et al. (2002) "Interannual and between species comparison in the lipids, fatty acids, and sterols of Antarctic krill from the US AMLR Elephant Island survey area: 1997 and 1998". Comp Biochem Physiol 131B:733-747.

Popp-Snijders et al., 1987, "Dietary supplementation of omega-3 polyunsaturated fatty acids improves insulin sensitivity in non-insulin-dependent diabetes", Diabetes Res. 4(3): 141-7.

Sachindra, 2006, "Recovery of carotenoids from shrimp waste in organic solvents", Waste Management, 26: 1092-1098.

Saether et al., 1986, "Lipids of North Atlantic krill", J Lipid Res., 27(3):274-85.

Shahidi et al., 1998, "Carotenoid Pigments in Seafoods and Aquaculture" Critical Reviews in Food Science, 38(1): 1-67.

Sidehu et al., 1970, "Biochmical Composition and Nutritive Value of Krill (*Euphausia superb* dana)", J. Sci Food Agr., vol. 21, 293-296.

Simopoulos, 1991, "Omega-3 fatty acids in health and disease and in growth and development", Am. Clin. Nutr. 54:438-63.

Somiya, 1982, "Yellow lens' eyes of a stomiatoid deep-sea fish, *Malacosteous niger*", Proc. R. Soc. Lond., 215: 481-489.

\* cited by examiner

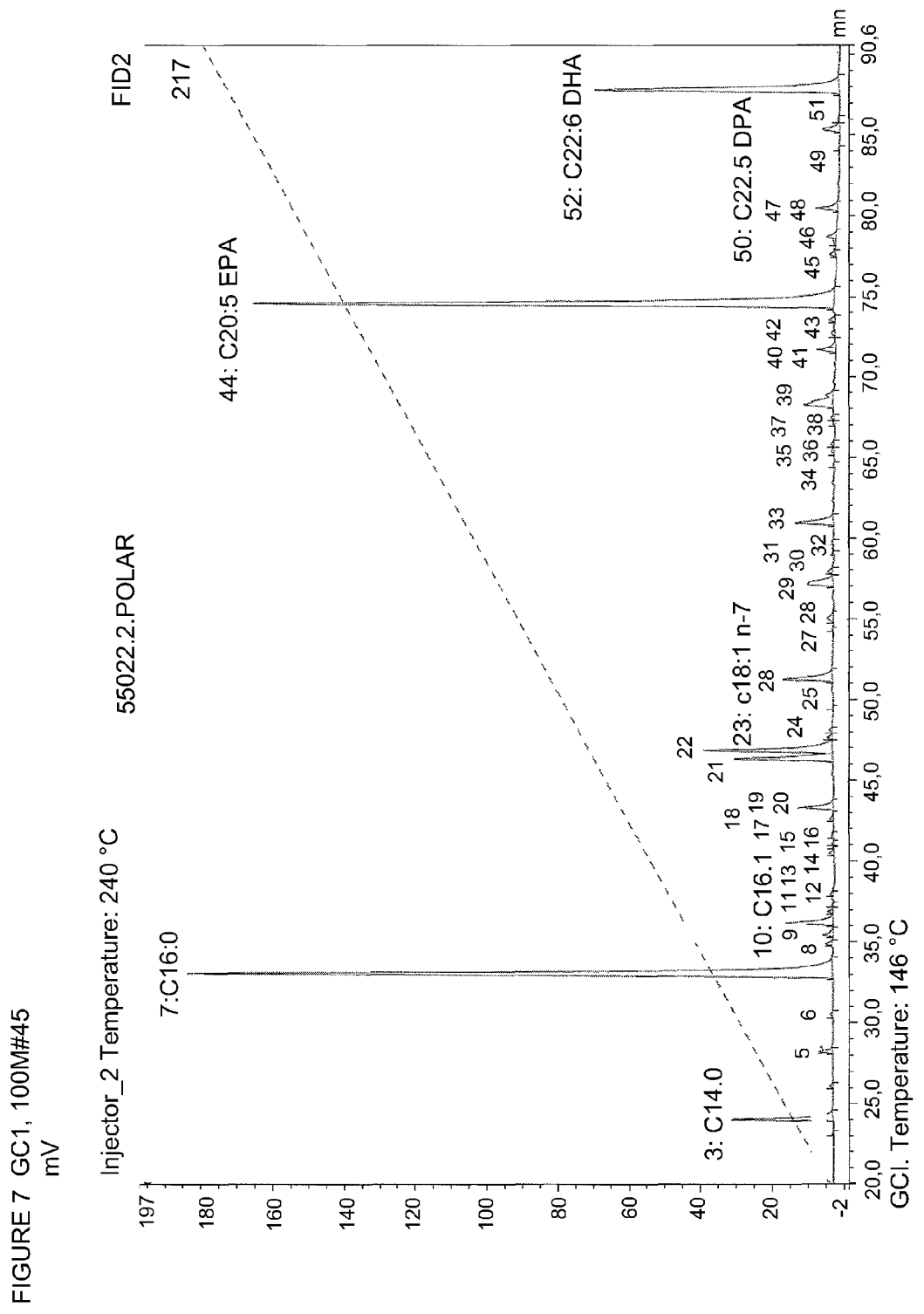

PHOSPHOLIPID AND PROTEIN TABLETS

CROSS REFERENCE TO RELATED APPLICATIONS

This application claims priority to U.S. Provisional Application Ser. No. 61/155,758, filed: Feb. 26, 2009, which is here incorporated by reference in its entirety.

FIELD OF THE INVENTION

The invention relates to tablets comprising phospholipids and protein, and in particular to the production of tablets containing astaxanthin and phospholipids comprising omega-3 fatty acid moieties.

BACKGROUND OF THE INVENTION

Krill is a small crustacean which lives in all the major oceans world-wide. For example, it can be found in the Pacific Ocean (*Euphausia pacifica*), in the Northern Atlantic (*Meganyctiphanes norvegica*) and in the Southern Ocean off the coast of Antarctica (*Euphausia superba*). Krill is a key species in the ocean as it is the food source for many animals such as fish, birds, sharks and whales. Krill can be found in large quantities in the ocean and the total biomass of Antarctic krill (*E. superba*) is estimated to be in the range of 300-500 million metric tons. Antarctic krill feeds on phytoplankton during the short Antarctic summer During winter, however, its food supply is limited to ice algae, bacteria, marine detritus as well as depleting body protein for energy. Virtue et al., Mar. Biol. 126, 521-527. For this reason, the nutritional values of krill vary during the season and to some extent annually. Phleger et al., Comp. Biochem. Physiol. 131B (2002) 733. In order to accommodate variations in food supply, krill has developed an efficient enzymatic digestive apparatus resulting in a rapid breakdown of the proteins into amino acids. Ellingsen et al., Biochem. J. (1987) 246, 295-305. This autoproteolysis is highly efficient also post mortem, making it a challenge to catch and store the krill in a way that preserves the nutritional quality of the krill. Therefore, in order to prevent the degradation of krill the enzymatic activity is either reduced by storing the krill at low temperatures or the krill is made into a krill meal.

During the krill meal process the krill is cooked so that all the active enzymes are denatured in order to eliminate all enzymatic activity. Krill is rich in phospholipids which act as emulsifiers. Thus it is more difficult to separate water, fat and proteins using mechanical separation methods than it is in a regular fish meal production line. In addition, krill becomes solid, gains weight and loose liquid more easily when mixed with hot water. Eventually this may lead to a gradual build up of coagulated krill proteins in the cooker and a non-continuous operation due to severe clogging problems. In order to alleviate this, hot steam must be added directly into the cooker. This operation is energy demanding and may also result in a degradation of unstable bioactive components in the krill such as omega-3 fatty acids, phospholipids and astaxanthin. The presence of these compounds, make krill oil an attractive source as a food supplement, a functional food products and a pharmaceutical for the animal and human applications.

Omega-3 fatty acids have recently been shown to have potential effect of preventing cardiovascular disease, cognitive disorders, joint disease and inflammation related diseases such as rheumatoid arthritis. Astaxanthin is a strong antioxidant and may therefore assist in promoting optimal health. Hence, there is a need for a method of processing krill into a krill meal at more gentle conditions which prevents the degradation of these valuable bioactive compounds.

SUMMARY OF THE INVENTION

The invention relates to processing crustaceans such as krill to provide oil and meal products, and in particular to the production of oils and other lipid extracts containing astaxanthin and phospholipids comprising omega-3 fatty acid moieties and meal rich in astaxanthin.

In some embodiments, the present invention provides compositions comprising less than about 150, 100, 10, 5, 2 or 1 mg/kg astaxanthin or from about 0.1 to about 1, 2, 5, 10 or 200 mg/kg astaxanthin, preferably endogenous, naturally occurring astaxanthin, also in the form of astaxanthin esters, from about 20% to about 50%, 15% to 45%, or 25% to 35% phospholipids on a w/w basis, and about 15% to 60%, about 20% to 50%, or about 25% to 40% protein on a w/w basis, wherein said phospholipids comprise omega-3 fatty acid residues. In some embodiments, the composition comprises a lipid fraction having an omega-3 fatty acid content of from about 5% to about 30%, from 10% to about 30%, or from about 12% to about 18% on a w/w basis. In some embodiments, the phospholipids comprise greater than about 60%, 65%, 80%, 85% or 90% phosphatidylcholine on a w/w basis. In some embodiments, the phospholipids comprise less than about 15%, 10%, 8% or 5% ethanolamine on a w/w basis. In some embodiments, the compositions comprise from about 1% to 10%, preferably 2% to 8%, and most preferably about 2% to 6% alkylacylphosphatidylcholine. In some embodiments, the compositions comprise from about 30% to about 70% triacylglycerol on a w/w basis. In further embodiments, the compositions comprise less than about 1% cholesterol. In some embodiments, the protein comprises from about 8% to about 14% leucine on a w/w basis and from about 5% to 11% isoleucine on a w/w basis.

In some embodiments, the present invention comprises an aqueous phase and a solid phase, said solid phase comprising from about 20% to about 50% phospholipids on a w/w basis, and about 20% to 50% protein on a w/w basis, wherein said phospholipids comprise from about 10% to about 20% omega-3 fatty acid residues.

In other embodiments, the present invention provides krill compositions comprising astaxanthin, a protein fraction, and a lipid fraction, wherein said lipid fraction comprises less than about 10%, 5% or 3% phospholipids on a w/w basis. In some embodiments, the phospholipids comprise less than about 15%, 10% or 5% phosphatidylcholine on a w/w basis.

In some embodiments, the present invention provides a krill meal comprising astaxanthin and from about 8% to about 31% lipids, preferably from about 8% to about 10 or 18% lipids, wherein said lipids comprises greater than about 80% neutral lipids on a w/w basis. In some embodiments, the krill meal comprises less than about 15%, 10%, 5%, 3% or 1% phospholipids. In some embodiments, the phospholipids comprise less than about 15%, 10% or 5% phosphatidylcholine on a w/w basis.

In some embodiments, the present invention provides methods of preparing a phospholipid composition from biological material or biomass comprising: mixing said biological material or biomass with water at a suitable temperature to form a solid phase and an aqueous phase comprising phospholipids and proteins; separating said solid phase from said aqueous phase; heating said aqueous phase at a temperature sufficient to form a phospholipid-protein precipitate; and separating said phospholipid-protein precipitate from said aqueous phase. In some embodiments, the present invention provides a phospholipid-protein precipitate obtained by using the foregoing method. In some embodiments, the biological material or biomass is krill. In other embodiments, the biological material or biomass is selected from crabs, shrimp, calanus, plankton, crayfish, eggs or other phospholipid containing biological materials or biomass. In some embodiments, the methods further comprise the step of forming a meal from said solid phase. In some embodiments, the step of forming a meal comprises: heating the solid phase in the presence of water; separating fat and protein in said solid phase; and drying said protein to form a meal. In some embodiments, the processes further comprise the steps of pressing and drying the coagulum to form a coagulum meal. In some embodiments, the drying is by hot air or steam. In some embodiments, the present invention provides a phospholipid-protein precipitate obtained by using the foregoing method. In some embodiments, the present invention provides a composition comprising a krill solid phase according to the foregoing methods. In some embodiments, the present invention provides a krill meal obtained by the foregoing methods.

In some embodiments, the present invention provides processes comprising: extracting a first lipid fraction from a krill biomass; extracting a second lipid fraction from a krill biomass; and blending said first lipid fraction and said second lipid fraction to provide a krill lipid composition having a desired composition. In some embodiments, the one or more of the extracting steps are performed in the absence of substantial amounts of organic solvents. In some embodiments, the first lipid fraction is extracted by: mixing krill with water at a suitable temperature to form a solid phase and an aqueous phase comprising phospholipids and protein; separating said solid phase from said aqueous phase; heating said aqueous phase at a temperature sufficient to form a phospholipid-protein precipitate; separating said phospholipid-protein precipitate from said aqueous phase; and separating said phospholipids from said protein. In some embodiments, the second lipid fraction is extracted by: heating the solid phase in the presence of water; and separating fat and protein in said solid phase. In some embodiments, the first lipid fraction comprises a phospholipid fraction comprising greater than about 90% phosphatidylcholine on a w/w basis. In some embodiments, the second lipid fraction comprises greater than about 80% neutral lipids on a w/w basis.

In some embodiments, the present invention provides processes of producing a phospholipid composition from biological material or biomass comprising: mixing said biological material or biomass with water to increase the temperature of said biological material to about 25 to 80° C., preferably to about 50 to 75° C., and most preferably to about 60 to 75° C. to form a first solid phase and a first aqueous phase comprising phospholipids and proteins; separating said first solid phase from said first aqueous phase; and separating a protein and phospholipid fraction from said first aqueous phase. In some embodiments, the biomass is heated to the first temperature for at least 3 minutes, preferably from about 3 minutes to 60 minutes, more preferably from about 3 minutes to 20 minutes, and most preferably from about 3 minutes to 10 minutes. The present invention is not limited to the use of any particular biological materials or biomass. In some embodiments, the biological material is a marine biomass. In some preferred embodiments, the biological material or biomass comprises krill crabs, shrimp, calanus, plankton, crayfish, eggs or other phospholipid containing biological materials or biomass. The present invention is not limited to the use of any particular type of krill. In some embodiments, the krill is fresh, while in other embodiments, the krill is frozen. In some embodiments, the krill is of the species *Euphausia superba*. In some embodiments, the step of separating a protein and phospholipid fraction from said first aqueous phase comprises heating said first aqueous phase at a temperature sufficient to form a phospholipid-protein coagulate and separating said phospholipid-protein coagulate from said aqueous phase. In some embodiments, the processes utilize a second heating step. In some embodiments, the first aqueous phase is heated to over 80° C., preferably to about 80 to 120° C., and most preferably to about 90 to 100° C. In some embodiments, the krill milk is held at these temperatures for from about 1 minute to about 60 minutes, preferably about 1 minute to about 10 minutes, and most preferably for about 2 minutes to 8 minutes. In some embodiments, the heating is at atmospheric pressure, while in other embodiments, the pressure is greater than atmospheric pressure. In some embodiments, the processes further comprise the step of pressing said phospholipid-protein coagulate to form a coagulate liquid phase and a coagulate press cake. In some embodiments, the processes further comprise drying said coagulate press cake to form a coagulate meal. In some embodiments, the processes further comprise extracting a coagulate oil from said coagulate meal. In some embodiments, the processes further comprise the steps of pressing and drying the coagulum to form a coagulum meal. In some embodiments, the drying is by hot air or steam.

In some embodiments, the step of separating a protein and phospholipid fraction from said first aqueous phase comprises filtration of said aqueous phase to provide a phospholipid-protein retentate comprising proteins and phospholipids. In some embodiments, filtration is via membrane filtration. In some embodiments, the filtration comprises filtering said aqueous phase through a microfilter with a pore size of from about 50 to 500 nm. In some embodiments, the processes further comprise the step of dewatering said phospholipid-protein retentate to form a retentate liquid phase and a retentate concentrate. In some embodiments, the processes further comprise the step of removing water from said retentate concentrate so that said retentate concentrate is microbially stable. In some embodiments, the processes further comprise the step of extracting a retentate oil from said retentate concentrate. In some embodiments, the processes further comprise the step of heating said first solid phase and then pressing said first solid phase to form a first press cake and a second liquid phase. In some embodiments, the processes further comprise the step of drying said first press cake to provide a first krill meal. In some embodiments, the processes further comprise the steps of heating said second liquid phase and then separating said second liquid phase to provide a first krill oil and stickwater. In some embodiments, the stickwater is evaporated and added to said first press cake, and a meal is formed from said evaporated stickwater and said first press cake to provide a second krill meal. In some embodiments, the second liquid phase is heated to over 80° C., preferably to about 80 to 120° C., and most preferably to about 90 to 100° C. prior to said separation. In some embodiments, the processes further comprise the step of combining the previously described coagulate oil or the retentate oil and the first krill oil to provide a blended oil. In other embodiments, the coagulate oil, retentate oil, or oil pressed from the first solid phase are combined with the coagulate meal or retentate. In further embodiments, the processes of the present invention comprise the further step of supplementing the meals or oils produced as described above with additional proteins, phospholipids, triglycerides, fatty acids, and/or astaxanthin to produce an oil or meal with a desired defined composition. As such, a person of skill in the art will readily recognize that the processes described above serve as a starting point for producing compositions that are further supplemented in subsequent process steps to produce a desired composition, such a composition containing elevated levels of proteins, lipids or astaxanthin. In some embodiments, the present invention provides the lipid-protein composition produced by the foregoing processes. In some embodiments, the present invention provides the coagulate meal produced by the foregoing processes. In some embodiments, the present invention provides the coagulate oil produced by the foregoing processes. In some embodiments, the present invention provides the retentate meal produced by the foregoing processes. In some embodiments, the present invention provides the retentate oil produced by the foregoing processes. In some embodiments, the present invention provides the krill meal produced by the foregoing processes. In some embodiments, the present invention provides a krill oil produced by the foregoing processes. In some embodiments, the present invention provides a blended oil produced by the foregoing processes. In some embodiments, the compositions of the present invention are supplemented with additional proteins, phospholipids, triglycerides, fatty acids, and/or astaxanthin to produce an oil or meal with a desired defined composition. As such, a person of skill in the art will readily recognize that the compositions described above serve as a starting point for producing compositions that are further supplemented in subsequent process steps to produce a desired composition, such a composition containing elevated levels of proteins, lipids or astaxanthin.

In some embodiments, the present invention provides processes comprising: heating a krill biomass to about 25 to 80° C., preferably to about 50 to 75° C., and most preferably to about 60 to 75° C.; separating said krill biomass into solid and liquid phases; extracting a first lipid fraction from said solid phase; extracting a second lipid fraction from said liquid phases; and blending said first lipid fraction and said second lipid fraction to provide a krill lipid composition having a desired composition. In some embodiments, the extracting steps are performed in the absence of substantial amounts of organic solvents. In some embodiments, the first lipid fraction comprises a phospholipid fraction comprising greater than about 90% phosphatidylcholine on a w/w basis. In some embodiments, the second lipid fraction comprises greater than about 80% neutral lipids on a w/w basis.

In some embodiments, the present invention provides krill compositions comprising from about 0.01 to about 200 mg/kg astaxanthin, from about 45% to about 65% fat w/w, and about 20% to 50% protein w/w, wherein said fat comprises omega-3 fatty acid residues. In some embodiments, the fat has an omega-3 fatty acid content of from about 10% to 30%, preferably 15% to about 25% on a w/w basis. In some embodiments, the fat comprises from about 20% to about 50% phospholipids w/w, wherein said phospholipids comprise greater than about 65% phosphatidylcholine w/w and from about 1% to about 10% alkylacylphosphatidylcholine. In some embodiments, the phospholipids comprise less than about 10% ethanolamine on a w/w basis. In some embodiments, the fat comprises from about 40% to about 70% triacylglycerol w/w. In some embodiments, the compositions further comprise less than about 1% cholesterol. In some embodiments, the protein comprises from about 8% to about 14% leucine on a w/w basis and from about 5% to 11% isoleucine on a w/w basis.

In some embodiments, the present invention provides krill compositions comprising from about 10% to about 20% protein w/w, about 15% to about 30% fat w/w, and from about 0.01 to about 200 mg/kg astaxanthin. In some embodiments, the fat has an omega-3 fatty acid content of from about 10% to about 30% on a w/w basis. In some embodiments, the fat comprises from about 30% to about 50% phospholipids w/w. In some embodiments, the phospholipids comprise greater than about 65% phosphatidylcholine w/w. In some embodiments, the phospholipids comprise less than about 10% ethanolamine on a w/w basis. In some embodiments, the fat comprises from about 40% to about 70% triacylglycerol w/w. In some embodiments, the compositions comprise less than about 1% cholesterol. In some embodiments, the protein comprises from about 7% to about 13% leucine on a w/w basis and from about 4% to 10% isoleucine on a w/w basis.

In some embodiments, the present invention provides krill meal press cakes comprising from about 65% to about 75% protein w/w (dry matter), from about 10% to about 25% fat w/w (dry matter), and from about 1 to about 200 mg/kg astaxanthin (wet base). In some embodiments, the fat comprises greater than about 30% neutral lipids and greater than about 30% phospholipids on a w/w basis. In some embodiments, the fat comprises from about 50 to about 60% neutral lipids w/w and from about 40% to about 55% polar lipids w/w. In some embodiments, the protein comprises from about 5% to about 11% leucine w/w and from about 3% to about 7% isoleucine w/w.

In some embodiments, the present invention provides krill meals comprising from about 65% to about 75% protein w/w (dry matter), from about 10% to about 25% fat w/w (dry matter), and from about 1 to about 200 mg/kg astaxanthin (wet base). In some embodiments, the fat comprises greater than about 30% neutral lipids and greater than about 30% phospholipids on a w/w basis. In some embodiments, the fat comprises from about 50 to about 60% neutral lipids w/w and from about 40% to about 55% polar lipids w/w. In some embodiments, the polar lipids comprise greater than about 90% phosphatidyl choline w/w. In some embodiments, the polar lipids comprise less than about 10% phosphatidyl ethanolamine w/w. In some embodiments, the protein comprises from about 5% to about 11% leucine w/w and from about 3% to about 7% isoleucine w/w.

In some embodiments, the present invention provides krill oil compositions comprising greater than about 1500 mg/kg total esterified astaxanthin, wherein said esterified astaxanthin comprises from about 25 to 35% astaxanthin monoester on a w/w basis and from about 50 to 70% astaxanthin diester on a w/w basis, and greater than about 20 mg/kg free astaxanthin.

In some embodiments, the present invention provides krill compositions comprising from about 3% to about 10% protein w/w, about 8% to about 20% dry matter w/w, and about 4% to about 10% fat w/w. In some embodiments, the fat comprises from about 50% to about 70% triacylglycerol w/w. In some embodiments, the fat comprises from about 30% to about 50% phospholipids w/w. In some embodiments, the phospholipids comprise greater than about 90% phosphatidyl choline w/w. In some embodiments, the fat comprises from about 10% to about 25% n-3 fatty acids. In some embodiments, the fat comprises from about 10% to about 20% EPA and DHA.

In some embodiments, the krill compositions of the present invention are supplemented with additional proteins, phospholipids, triglycerides, fatty acids, and/or astaxanthin to produce an oil or meal with a desired defined composition. As such, a person of skill in the art will readily recognize that the krill compositions described above serve as a starting point for producing compositions that are further supplemented in subsequent process steps to produce a desired composition, such a composition containing elevated levels of proteins, lipids or astaxanthin.

The meal and oil compositions of the present invention described above are characterized in containing low levels, or being substantially free of many volatile compounds that are commonly found in products derived from marine biomass. In some embodiments, the meals and oils of the present invention are characterized as being substantially free of one or more of the following volatile compounds: acetone, acetic acid, methyl vinyl ketone, 1-penten-3-one, n-heptane, 2-ethyl furan, ethyl propionate, 2-methyl-2-pentenal, pyridine, acetamide, toluene, N,N-dimethyl formamide, ethyl butyrate, butyl acetate, 3-methyl-1,4-heptadiene, isovaleric acid, methylpyrazine, ethyl isovalerate, N,N-dimethyl acetamide, 2-heptanone, 2-ethyl pyridine, butyrolactone, 2,5-dimethylpyrazine, ethyl pyrazine, N,N-dimethyl propanamide, benzaldehyde, 2-octanone, β-myrcene, dimethyl trisulfide, trimethyl pyrazine, 1-methyl-2-pyrrolidone. In other embodiments, the meals and oils of the present invention are characterized in containing less than 1000, 100, 10, 1 or 0.1 ppm (alternatively less than 10 mg/100 g, preferably less than 1 mg/100 g and most preferably less than 0.1 mg/100 g) of one or more of the following volatile compounds: acetone, acetic acid, methyl vinyl ketone, 1-penten-3-one, n-heptane, 2-ethyl furan, ethyl propionate, 2-methyl-2-pentenal, pyridine, acetamide, toluene, N,N-dimethyl formamide, ethyl butyrate, butyl acetate, 3-methyl-1,4-heptadiene, isovaleric acid, methylpyrazine, ethyl isovalerate, N,N-dimethyl acetamide, 2-heptanone, 2-ethyl pyridine, butyrolactone, 2,5-dimethylpyrazine, ethyl pyrazine, N,N-dimethyl propanamide, benzaldehyde, 2-octanone, β-myrcene, dimethyl trisulfide, trimethylpyrazine, 1-methyl-2-pyrrolidone. In further embodiments, the compositions of the present invention are characterized in comprising less than 10 mg/100 g, and preferably less than 1 mg/100 g (dry weight) of trimethylamine (TMA), trimethylamine oxide (TMAO) and/or lysophosphatidylcholine.

In some embodiments, the present invention provides systems for processing of marine biomass comprising: a mixer for mixing marine biomass and water to form a mixture having a defined temperature, wherein said mixture has a first solid phase and a first liquid phase. In some embodiments, the water is heated and said defined temperature of said mixture is from about 25 to 80° C., preferably to about 50 to 75° C., and most preferably to about 60 to 75° C. In some embodiments, the systems further comprise a separator in fluid communication with said mixer for separating said first solid phase and said first liquid phase. In some embodiments, the first separator is a filter. In some embodiments, the systems further comprise a first heater unit in fluid communication with said first separator, wherein said first heater unit heats said first liquid phase to a defined temperature. In some embodiments, the defined temperature is about 80° C. to about 100° C., preferably 90° C. to about 100° C., most preferably 95° C. to about 100° C. In some embodiments, the systems further comprise a microfilter in fluid communication with said mixer, wherein said liquid phase is separated into a retentate phase and a permeate phase by said microfilter. In some embodiments, the systems further comprise a prefilter in line with said microfilter. In some embodiments, the prefilter is a sieve In some embodiments, the water is heated and said defined temperature of said mixture is from about 25 to 80° C., preferably to about 50 to 75° C., and most preferably to about 60 to 75° C. In some embodiments, the systems further comprise a first separator in fluid communication with said mixer for separating said first solid phase and said first liquid phase. In some embodiments, the first separator is a filter.

In some embodiments, the present invention provides krill compositions comprising from about 10% to about 20% protein w/w, about 15% to about 30% fat w/w, from about 0.01% to about 200 mg/kg astaxanthin, and less than about 1 mg/100 g trimethyl amine, trimethyl amine, volatile nitrogen, or 1 g/100 g lysophosphatidylcholine or combinations thereof. In some embodiments, the fat has an omega-3 fatty acid content of from about 10% to about 25% on a w/w basis. In some embodiments, the fat comprises from about 35% to about 50% phospholipids w/w. In some embodiments, the phospholipids comprise greater than about 90% phosphatidylcholine w/w. In some embodiments, the phospholipids comprise less than about 10% ethanolamine on a w/w basis. In some embodiments, the fat comprises from about 40% to about 60% triacylglycerol w/w. In some embodiments, the compositions further comprise less than about 1% cholesterol. In some embodiments, the protein comprises from about 7% to about 13% leucine on a w/w basis and from about 4% to 10% isoleucine on a w/w basis.

In some embodiments, the present invention provides processes for processing of marine biomass comprising: providing a marine biomass and a mixer for mixing marine biomass and water to form a mixture having a defined temperature, wherein said mixture comprises a first solid phase and a first liquid phase. In some embodiments, the defined temperature of said mixture is from about 25 to 80° C., preferably to about 50 to 75° C., and most preferably to about 60 to 75° C. In some embodiments, the processes further comprise the steps of separating said liquid phase from said solid phase, and heating said liquid phase to about 80° C. to about 100° C., preferably 90° C. to about 100° C., most preferably 95° C. to about 100° C., to produce a coagulate. In some embodiments, the coagulate comprises proteins and lipids. In some embodiments, the coagulate is separated from residual liquid by filtering.

In some embodiments, the present invention provides systems for processing of marine biomass comprising: a ship; a trawl net towable from said ship, said trawl net configured to catch the marine biomass; and a mixer for mixing said marine biomass and water to form a mixture having a defined temperature, wherein said mixture has a first solid phase and a first liquid phase. In some embodiments, the marine biomass is krill. In some embodiments, the krill is fresh krill and the trawl and ship are configured to deliver the fresh krill to the mixer. In some embodiments, system comprises a pump to transfer the biomass from the krill to the ship. In some embodiments, the system comprises a microfilter in fluid communication with said mixer, wherein said microfilter separates said first solid phase and said first liquid phase. In some embodiments, the marine biomass is krill. In some embodiments, the krill is fresh krill.

In some embodiments, the present invention provides a solid dosage form (e.g., a tablet) comprising an active ingredient in a concentration of greater than about 40% by weight of said dosage form, wherein said active ingredient is a protein-phospholipid composition comprising protein in a concentration of about 30% to about 50% by weight of the active ingredient and fat in a concentration of about 50% to about 75% by weight of the active ingredient, wherein the fat comprises phospholipids in a concentration of about 35% to about 60% by weight of the fat; and an adsorption agent; wherein said dosage form has a hardness of greater than about 60 N. In some embodiments, a standard USP test is used for hardness. In some embodiments, hardness is measured by an apparatus consisting of two jaws facing each other, one of which moves towards the other. The flat surfaces of the jaws are perpendicular to the direction of movement. The crushing surfaces of the jaws are flat and larger than the zone of contact with the tablet. The apparatus is calibrated using a system with a precision of 1 newton. The tablet is placed between the jaws, taking into account, where applicable, the shape, the breakmark and the inscription; for each measurement the tablet is oriented in the same way with respect to the direction of application of the force. In some embodiments, the measurement is carried out on 10 tablets, taking care that all fragments of tablets have been removed before each determination.

In some embodiments, the protein-phospholipid composition is derived from krill. In some embodiments, the active ingredient further comprises astaxanthin. In some embodiments, the active ingredient comprises from about 1 to about 200 mg/kg astaxanthin. In some embodiments, the fat comprises omega-3 fatty acids residues in a concentration of from about 10% to about 35% by weight of said fat. In some embodiments, the phospholipids comprise phosphatidylcholine in a concentration of greater than about 65% by weight of the phospholipids. In some embodiments, the phospholipids comprise alkylacylphosphatidylcholine in a concentration of from about 2% to about 10% by weight of the phospholipids. In some embodiments, the adsorption agent is provided in a concentration of from about 18% to about 25% by weight of the dosage form. In some embodiments, the adsorption agent is magnesium aluminometasilicate or Neusilin™. In some embodiments, the solid dosage form further comprises a binding agent in a concentration of from about 8% to about 15% by weight of the dosage form. In some embodiments, the solid dosage form further comprises a disintegrant in a concentration of from about 2% to about 8% by weight of the dosage form. In some embodiments, the solid dosage form comprises omega-3 fatty residues in a concentration of about 2.5% to 15% by weight of the dosage form. In some embodiments, the fat comprises triglycerides in a concentration of from about 40% to about 65% by weight of the fat. In some embodiments, the protein comprises from about 8% to about 14% leucine by weight of said protein. In some embodiments, the dissolution of the dosage form in a medium containing demineralized water as a solvent is greater than 75 percent at about 10 minutes where the tablet is raised and lowered in said solvent at a constant frequency rate between 29 and 32 cycles per minute, through a distance of 55±2 mm. In some embodiments, the dosage form is a tablet.

In some embodiments, the present invention provides a solid dosage form comprising an active ingredient in a concentration of about 55% to about 65% by weight of said dosage form, wherein said active ingredient is a protein-phospholipid composition comprising protein in a concentration of about 30% to about 50% by weight of said active ingredient and fat in a concentration of about 50% to about 75% by weight of said active ingredient, wherein said fat comprises phospholipids in a concentration of about 35% to about 60% by weight of said fat; an adsorption agent in a concentration of about 18% to about 25% by weight of said dosage form, a binding agent in a concentration of about 8% to about 15% by weight of said dosage form; wherein said dosage form has a hardness of greater than about 60 N.

In some embodiments, the present invention provides processes for the preparation of the foregoing solid dosages forms comprising: wet granulating an inner phase comprising an active ingredient, wherein said active ingredient is a protein-phospholipid composition comprising protein in a concentration of about 30% to about 50% by weight of said active ingredient and fat in a concentration of about 50% to about 75% by weight of said active ingredient, wherein said fat comprises phospholipids in a concentration of about 35% to about 60% by weight of said fat, and one or more pharmaceutically acceptable excipients; forming an outer phase comprising one or more pharmaceutically acceptable excipients; mixing said outer phase with said inner phase to form a compressible mixture; and compressing said compressible mixture to form a tablet. In some embodiments, the one or more pharmaceutically acceptable ingredients in the inner phase comprise magnesium aluminometasilicate or Neusilin™. In some embodiments, the one or more pharmaceutically acceptable ingredients in the outer phase comprise magnesium aluminometasilicate or Neusilin™. In some embodiments, the present invention provides a solid dosage form prepared by the foregoing processes.

In some embodiments, the present invention provides a pharmaceutical composition comprising one or more of the compositions described above in combination with a pharmaceutically acceptable carrier. In some embodiments, the present invention provides a food product comprising one or of the foregoing compositions. In some embodiments, the present invention provides a dietary supplement comprising one or more of the foregoing compositions. In some embodiments, the present invention provides an animal feed comprising one or more of the foregoing compositions.

DESCRIPTION OF THE FIGURES

FIG. 7 is a GC analysis of the polar fraction extracted from krill coagulate.

DEFINITIONS

Figure 1:
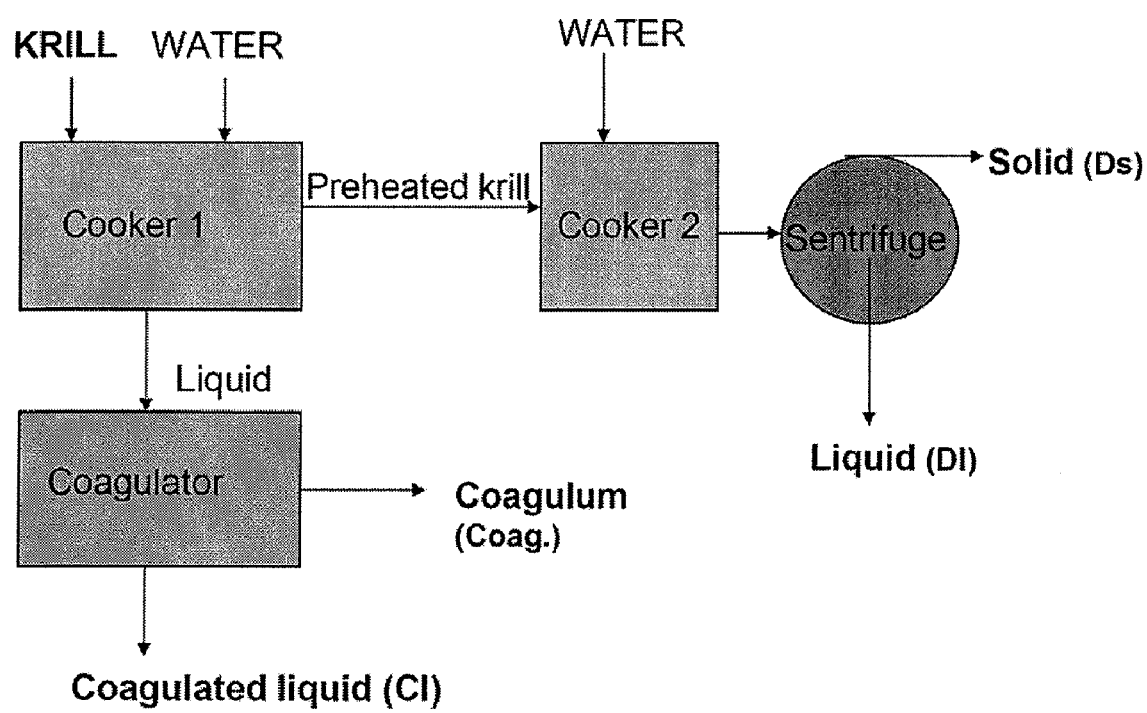
FIG. 1 shows an overview of the process of making krill meal with a two stage cooking process.

As used herein, "phospholipid" refers to an organic compound having the following general structure:

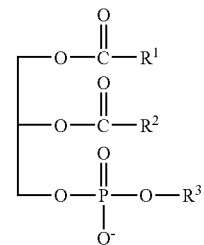

wherein R1 is a fatty acid residue, R2 is a fatty acid residue or —OH, and R3 is a —H or nitrogen containing compound choline (HOCH$_2$CH$_2$N$^+$(CH$_3$)$_3$OH$^-$), ethanolamine (HOCH$_2$CH$_2$NH$_2$), inositol or serine. R1 and R2 cannot simultaneously be OH. When R3 is an —OH, the compound is a diacylglycerophosphate, while when R3 is a nitrogen-containing compound, the compound is a phosphatide such as lecithin, cephalin, phosphatidyl serine or plasmalogen.

An "ether phospholipid" as used herein refers to a phospholipid having an ether bond at position 1 the glycerol backbone. Examples of ether phospholipids include, but are not limited to, alkylacylphosphatidylcholine (AAPC), lyso-alkylacylphosphatidylcholine (LAAPC), and alkylacylphosphatidylethanolamine (AAPE). A "non-ether phospholipid" is a phospholipid that does not have an ether bond at position 1 of the glycerol backbone.

As used herein, the term omega-3 fatty acid refers to polyunsaturated fatty acids that have the final double bond in the hydrocarbon chain between the third and fourth carbon atoms from the methyl end of the molecule. Non-limiting examples of omega-3 fatty acids include, 5,8,11,14,17-eicosapentaenoic acid (EPA), 4,7,10,13,16,19-docosahexanoic acid (DHA) and 7,10,13,16,19-docosapentanoic acid (DPA).

As used herein, astaxanthin refers to the following chemical structure:

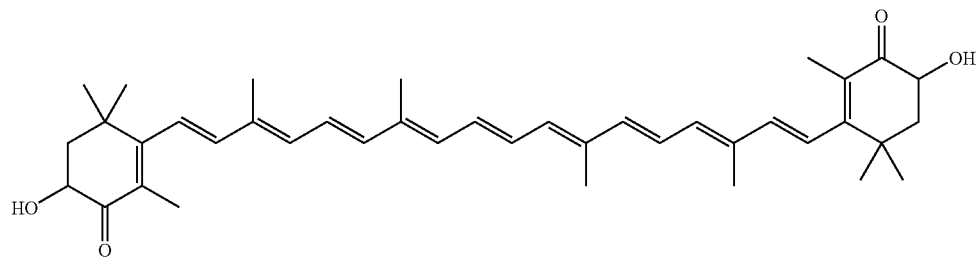 [SMILES: CC1=C(/C=C/C(C)=C/C=C/C(C)=C/C=C/C=C(C)/C=C/C=C(C)/C=C/C2=C(C)C(=O)C(O)CC2(C)C)C(C)(C)CC(O)C1=O]

As used herein, astaxanthin esters refer to the fatty acids esterified to OH group in the astaxanthin molecule.

As used herein, the term w/w (weight/weight) refers to the amount of a given substance in a composition on weight basis. For example, a composition comprising 50% w/w phospholipids means that the mass of the phospholipids is 50% of the total mass of the composition (i.e., 50 grams of phospholipids in 100 grams of the composition, such as an oil).

As used herein, the term "fresh krill" refers to krill that is has been harvested less than about 12, 6, 4, 2 or preferably 1 hour prior to processing. "Fresh krill" is characterized in that products made from the fresh krill such as coagulum comprise less than 1 mg/100 g TMA, volatile nitrogen or Trimethylamine oxide-N, alone or in combination, and less than 1 g/100 g lysophosphatidylcholine.

The term "tablet" as used herein is intended to encompass compressed pharmaceutical dosage formulations of all shapes and sizes, whether coated or uncoated.

As used herein, the term "excipient" refers to the additives used to convert an active compound into a form suitable for its intended purpose. For compositions of the present invention suitable for administration to humans, the term "excipient" is meant to include, but is not limited to, those ingredients described in Remington: The Science and Practice of Pharmacy, Lippincott Williams & Wilkins, 21.sup.st ed. (2004), which is herein incorporated by reference in its entirety.

DETAILED DESCRIPTION OF THE INVENTION

The invention relates to processing crustaceans such as krill to provide oil and meal products, and in particular to the production of oils containing astaxanthin and phospholipids comprising omega-3 fatty acid moieties and meal rich in astaxanthin. In some embodiments, the present invention provides systems and methods for the continuous processing of fresh or frozen krill into useful products, including krill oil, krill meal, and a krill protein/phospholipid coagulum.

Previous processes for treating marine biomasses such as krill have utilized a single high temperature treatment to provide a proteinaceous product. Pat No. SU220741; "Removing fats from the protein paste "Okean". Gulyaev and Bugrova, Konservnaya i Ovoshchesushil'naya Promyshlennost (1976), (4), 37-8; Amino acid composition of protein-coagulate in krill. Nikolaeva, VNIRO (1967), 63 161-4. However, these methods result in a product with a relatively low lipid content. The present invention describes a process in which the marine biomass such as krill is first heated at moderate temperatures to provide an aqueous phase which is subsequently heated at a higher temperature. This process provides a novel protein-lipid composition that has a higher lipid content than previously described compositions produced from marine biomasses. The compositions of the present invention are further distinguished from other krill oil supplements marketed for human use in that the described compositions are, in some embodiments, provided as solids or powders comprising a combination of krill lipids, including krill phospholipids and krill triglycerides, and krill-derived protein. These solids/powders may preferably be provided in capsules, gel capsules, or as tablets or caplets.

In some embodiments, the present invention provides solvent-free methods to produce a phospholipid-containing composition from a biomass such as krill, crabs, Calanus, plankton, eggs, crayfish, shrimp and the like without using organic solvents. In some embodiments, the biomass (preferably krill, freshly harvested or frozen) is heated to a temperature in the range of 25 to 80° C., preferably 40 to 75° C., and most preferably 60 to 75° C. in order to dissolve/disperse lipids and proteins from the krill into the water phase, which is called krill milk. In some embodiments, the biomass is heated to and held at this first temperature for at least 3 minutes, preferably from about 3 minutes to 60 minutes, more preferably from about 3 minutes to 20 minutes, and most preferably from about 3 minutes to 10 minutes. In some embodiments, the processes then utilize a second heating step. The proteins and phospholipids are precipitated out of the water phase produced from the first heating step by heating the krill milk (after removal of the krill solids) to a temperature of greater than about 80° C., preferably 80 to 120° C., most preferably 95 to 100° C. In some embodiments, the krill milk is held at these temperatures for from about 1 minute to about 60 minutes, preferably about 1 minute to about 10 minutes, and most preferably for about 2 minutes to 8 minutes. The water phase may be heated at atmospheric pressure, or the water phase may be heated in a closed system at an elevated pressure so that the temperature can be increased above 100° C. Accordingly, in some embodiments, the heating is at atmospheric pressure, while in other embodiments, the pressure is greater than atmospheric pressure. The precipitate formed (hereafter called a coagulum) can be isolated and characterized. In some embodiments, the processes further comprise the steps of pressing and drying the coagulum to form a coagulum meal. In some embodiments, the drying is by hot air or steam.

The solid phase (e.g., krill solids) is preferably used to make a krill meal which also has a novel composition. In other embodiments, the krill milk is microfiltrated. The solid phase produced by microfiltration (called the retentate) is similar to that of the coagulum. Data show that the coagulum and retentate are low in cholesterol. In some embodiments, the retentate and coagulum are substantially free of cholesterol. In some embodiments, the retentate and coagulum comprise less than 1% cholesterol, preferably less than 0.1% cholesterol. This is a novel method to remove at least a portion of the lipids, such as phospholipids, from the krill. Removal of lipids from krill has previously required solvent extraction using liquids such as ethanol or other polar solvents. Solvent extraction is time-consuming and may also result in loss of material and is therefore not wanted. The krill used to separate out the coagulum had been stored frozen for 10 months prior to the experimentation. It is believed that due to the release of proteolytic enzyme activity during a freezing/thawing process, more protein can be expected to be solubilized based on the processing of frozen krill than from fresh krill.

In some embodiments, the present invention provides systems and processes for processing a marine biomass. In preferred embodiments, the marine biomass is krill, preferably the Antarctic krill *Euphausia superba*. Other krill species may also be processed using the systems and processes of the present invention. In some embodiments, the krill is processed in a fresh state as defined herein. In some embodiments, the krill is processed on board a ship as described below within 12, 10, 8, 6, 4, or preferably 2 hours of catching the krill. In some embodiments, the krill is processed on board a ship within 1 or preferably 0.5 hours of catching the krill. In some embodiments, the ship tows a trawl that is configured to catch krill. The krill is then transferred from the trawl to the ship and processed. In some embodiments, the trawl comprises a pump system to pump the freshly caught krill from the trawl to the ship so that the krill can be processed in a fresh state. In preferred embodiments, the pump system comprises a tube that extends below the water the trawl and a pumping action is provided by injecting air into the tube below the waterline so that the krill is continuously drawn or pumped from the trawl, through the tube and on board the ship. Preferred trawling systems with pumps are described in PCT Applications WO 07/108,702 and WO 05/004593, incorporated herein by reference.

Some embodiments of the systems and processes of the present invention are shown in FIG. 1. As shown in FIG. 1, fresh or frozen is krill is mixed in mixer with a sufficient amount of hot water from water heater to increase the temperature of the krill mass to approximately 40 to 75° C., preferably 50 to 75° C., more preferably 60 to 75° C., and most preferably about 60 to 70° C. Many different types of water heaters are useful in the present invention. In some embodiments, the water heater is a steam heated kettle, while in other embodiments, the water heater is a scraped surface heat exchanger. The heated mass is then separated into liquid (krill milk) and krill solid fractions in a filter. In some embodiments, the separation is performed by sieving through a metal sieve. After separation, the krill milk is heated to approximately 90° C. to 100° C., preferably to about 95° C. to 100° C. in a heater. Any type of suitable water or liquid heater may be used. In preferred embodiments, the heater is a scraped surface heat exchanger. This heating step produced a solid fraction (the coagulum described above) and a liquid fraction. In some preferred embodiments, the separator utilizes a filter as previously described. The present invention is not limited to the use of any particular type of filter. In some embodiments, the filter is a woven filter. In some embodiments, the filter comprises polymeric fibers. The coagulum is introduced into a dewaterer. In some embodiments, the dewaterer is a press such as screw press. Pressing produces a liquid fraction and a press cake. The press cake is dried in a drier to produce coagulum meal.

The solid krill fraction is introduced into a dewaterer for dewatering. In some embodiments, the dewaterer is a press such as screw press. Pressing produces a press cake and a liquid fraction. The press cake is dried in a drier, such as an air drier or steam drier, to provide krill meal. The liquid fraction is centrifuged to produce a neutral krill oil containing high levels of astaxanthin and stickwater. In preferred embodiments, the stick water is added back into the krill press cake to make a full meal, including the various components of the stick water such as soluble proteins, amino acids, etc.

In alternative embodiments, the krill milk can be treated by microfiltration instead of by heating to form a coagulum. The krill milk is introduced into a microfilter. Microfiltration produces a fraction called a retentate and a liquid permeate. The retentate is concentrated by evaporation under vacuum to stability, water activity <0.5 Aw. Membrane filtration of cooking liquid is preferably performed at about 70° C. with a filter having a pore size of about 10 nm to about 1000 nm, more preferably about 50 to about 500 nm, and most preferably about 100 nm. An exemplary filter is the P19-40 100 nm $ZrO_2$ membrane. In some embodiments, the liquid fraction is pre-filtered prior to microfiltration. In preferred embodiments, the prefilter is a roto-fluid sieve (air opening 100 nm).

In yet another embodiment of the invention is a novel and more efficient method of preparing krill meal. By removing the coagulum, the krill meal process is less susceptible to clogging problems and the use of hot steam in the cooker can be avoided. The data disclosed show the coagulum contains a high percentage of phospholipids, hence the separation of the fat in the new krill meal process can be obtained using mechanical methods as in standard fish meal processes. In fact, the separation of fat from the meal is important. Ideally, the krill meal should have a low fat value in order to have satisfactory technical properties. Mechanically separating the fat from the meal will result in a neutral oil rich in astaxanthin. If the neutral oil rich in astaxanthin stays in the meal, the astaxanthin may be degraded during the drying.

In some embodiments, the present invention provides a krill coagulate and retentate compositions. The compositions are characterized in containing a combination of protein and lipids, especially phospholipids. In preferred embodiments, the compositions are solids or powders and are provided as a meal. In some embodiments, the compositions comprise from about 20% to about 50% protein w/w, preferably about 30% to 40% protein w/w, and about 40% to 70% lipids w/w, preferably about 50% to 65% lipids w/w, so that the total amount of proteins and lipids in the compositions of from 90 to 100%. In some embodiments, the lipid fraction contains from about 10 g to 30 g omega-3 fatty acid residues per 100 g of lipid, preferably about 15 g to 25 g omega-3 fatty acids residues per 100 g lipids (i.e., from 10 to 30% or preferably from 15 to 25% omega-3 residues expressed w/w as a percentage of total lipids in the composition). In some embodiments, the lipid fraction of the composition comprises from about 25 to 50 g polar lipids per 100 g lipids (25 to 50% w/w expressed as percentage of total lipids), preferably about 30 to 45 g polar lipids per 100 g total lipids (30 to 45% w/w expressed as percentage of total lipids), and about 50 to 70 g nonpolar lipids per 100 g lipids (50 to 70% w/w expressed as percentage of total lipids), so that the total amount of polar and nonpolar lipids is 90 to 100% of the lipid fraction. In some embodiments, the phospholipids comprise greater than about 60% phosphatidylcholine on a w/w basis. In some embodiments, the phospholipids comprise less than about 10% ethanolamine on a w/w basis. In some embodiments, the compositions comprise from about 20% to about 50% triacylglycerol on a w/w basis. In some embodiments, the compositions comprise less than about 1% cholesterol. In some embodiments, the protein fraction comprises from about 8% to about 14% leucine on a w/w basis and from about 5% to 11% isoleucine on a w/w basis. In some embodiments, the compositions comprise less than about 200, 10, 5 or 1 mg/kg naturally occurring or endogenous astaxanthin. In some embodiments, the compositions comprise from about 0.01 to about 200 mg/kg naturally-occurring astaxanthin. It will be recognized that the astaxanthin content of the composition can be increased by adding in astaxanthin from other (exogenous) sources, both natural and non-natural. Likewise, the compositions can be supplemented with exogenous proteins, triglycerides, phospholipids and fatty acids such as omega-3 fatty acids to produce a desired composition.

In yet another embodiment of the invention is a pre-heated krill composition. Non-limiting examples of the pre-heated krill composition is a krill composition comprising lipids with less than 10% or 5% phospholipids, and in particular phosphatidylcholine.

In yet another embodiment of the invention is a novel krill meal product produced from the solid phase left after the first heating step (i.e., the heating step at below 80 C). The krill meal has good nutritional and technical qualities such as a high protein content, low fat content and has a high flow number. Unexpectedly, the ratios of polar lipids to neutral lipids and EPA to DHA is substantially enhanced as compared to normal krill meal. In some embodiments, the krill meals comprise from about 60% to about 80% protein on a w/w basis, preferably from about 70% to 80% protein on a w/w basis, from about 5% to about 20% fat on a w/w basis, and from about 1 to about 200 mg/kg astaxanthin, preferably from about 50 to about 200 mg/kg astaxanthin. In some embodiments, the fat comprises from about 20 to 40% total neutral lipids and from about 50 to 70% total polar lipids on a w/w basis (total lipids). In some embodiments, the ratio of polar to neutral lipids in the meal is from about 1.5:1 to 3:1, preferably about 1.8:1 to 2.5:1, and most preferably from about 1.8:1 to 2.2:1. In some embodiments, the fat comprises from about 20% to 40% omega-3 fatty acids, preferably about 20% to 30% omega-3 fatty acids. In some embodiments, the ratio of EPA:DHA is from about 1.8:1 to 1:0.9, preferably from about 1.4:1 to 1:1.

In still other embodiments, the present invention provides oil produced by the processes described above. In some embodiments, the oils comprise greater than about 1800 mg/kg total esterified astaxanthin, wherein said esterified astaxanthin comprises from about 25 to 35% astaxanthin monoester on a w/w basis and from about 50 to 70% astaxanthin diester on a w/w basis, and less than about 40 mg/kg free astaxanthin.

The compositions of the present invention are highly palatable humans and other animals. In particular the oil and meal compositions of the present invention are characterized as containing low levels of undesirable volatile compounds or being substantially free of many volatile compounds that are commonly found in products derived from marine biomass. In some embodiments, the meals and oils of the present invention are characterized as being substantially free of one or more of the following volatile compounds: acetone, acetic acid, methyl vinyl ketone, 1-penten-3-one, n-heptane, 2-ethyl furan, ethyl propionate, 2-methyl-2-pentenal, pyridine, acetamide, toluene, N,N-dimethyl formamide, ethyl butyrate, butyl acetate, 3-methyl-1,4-heptadiene, isovaleric acid, methylpyrazine, ethyl isovalerate, N,N-dimethyl acetamide, 2-heptanone, 2-ethyl pyridine, butyrolactone, 2,5-dimethylpyrazine, ethyl pyrazine, N,N-dimethyl propanamide, benzaldehyde, 2-octanone, β-myrcene, dimethyl trisulfide, trimethylpyrazine, 1-methyl-2-pyrrolidone. In other embodiments, the meals and oils of the present invention are characterized in containing less than 1000, 100, 10, 1 or 0.1 ppm (alternatively less than 10 mg/100 g, preferably less than 1 mg/100 g and most preferably less than 0.1 mg/100 g) of one or more of the following volatile compounds: acetone, acetic acid, methyl vinyl ketone, 1-penten-3-one, n-heptane, 2-ethyl furan, ethyl propionate, 2-methyl-2-pentenal, pyridine, acetamide, toluene, N,N-dimethyl formamide, ethyl butyrate, butyl acetate, 3-methyl-1,4-heptadiene, isovaleric acid, methylpyrazine, ethyl isovalerate, N,N-dimethyl acetamide, 2-heptanone, 2-ethyl pyridine, butyrolactone, 2,5-dimethylpyrazine, ethyl pyrazine, N,N-dimethyl propanamide, benzaldehyde, 2-octanone, β-myrcene, dimethyl trisulfide, trimethylpyrazine, 1-methyl-2-pyrrolidone. In further embodiments, the compositions of the present invention are characterized in comprising less than 10 mg/100 g, and preferably less than 1 mg/100 g (dry weight) of trimethylamine (TMA), trimethylamine oxide (TMAO) and/or lysophosphatidylcholine.

In some embodiments, the compositions of this invention (such as those described in the preceding sections) are contained in acceptable excipients and/or carriers for oral consumption. In some embodiments, the present invention provides a pharmaceutical compositions one or more of the foregoing compositions in combination with a pharmaceutically acceptable carrier. The carrier may be a liquid, gel, gelcap, capsule, powder, solid tablet (coated caplet or non-coated), tea, or the like. The composition is preferably in the form of a tablet or capsule and most preferably in the form of a soft gel capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.).

In some embodiments, the present invention provides protein-phospholipid powders/meals in a solid dosage form, for example a tablet, comprising an active ingredient in a concentration of about greater than 55% by weight of the dosage form, wherein said active ingredient is a protein-phospholipid composition; wherein said dosage form has a hardness of greater than about 60 N.

In some preferred embodiments, the active ingredient is the meal/powder prepared from krill milk as described above. In some embodiments, the active ingredient is provided in 50%, or 60% by weight of the dosage form. In some embodiments, the active ingredient is provided in a concentration of from about 40% to 70%, preferably about 55% to about 63% or 65% by weight of the dosage form. In some embodiments, the active ingredient comprises protein in a concentration of about 30% to about 50% by weight of the active ingredient and fat in a concentration of about 45% to about 75%, preferably about 50% to about 75%, by weight of the active ingredient. In some embodiments, the fat comprises phospholipids in a concentration of about 20% to about 65%, preferably about 35% to about 60%, by weight of said fat. In embodiments, the fat comprises omega-3 fatty acids residues in a concentration of from about 10% to about 35%, preferably about 10% to about 30%, by weight of the fat. In some embodiments, the phospholipids comprise phosphatidylcholine in a concentration of greater than about 65% by weight of the phospholipids. In some embodiments, the phospholipids comprise alkylacylphosphatidylcholine in a concentration of from about 1% or 2% to about 10% by weight of the phospholipids. In some embodiments, the solid dosage form comprises omega-3 fatty residues in a concentration of about 2.5% to 20%, preferably about 2.5% to about 15% by weight of said dosage form. In some embodiments, the active ingredient further comprises astaxanthin. In some embodiments, the active ingredient comprises from about 1 to about 200 mg/kg astaxanthin.

In some embodiments, the oral dosage forms of the present invention further comprise one or more adsorption agent(s). In some preferred embodiments, the adsorption agent is magnesium aluminometasilicate. In some embodiments, the adsorption agent is provided in a concentration of from about 18% to about 30% by weight of the dosage form, preferably in a concentration of about 20% to about 26% by weight of the dosage form, and most preferably in a concentration of from about 22% to about 25% by weight of the dosage form. In some embodiments, the adsorption agent is provided in a concentration of from about 20% to about 23% by weight of the dosage form.

In some embodiments, the oral dosage forms of the present invention further comprise one or more binding agent(s). In some preferred embodiments, the binding agent is selected from the group consisting of hydroxypropyl cellulose (HPC), polyvinyl pyrrolidone (PVP), and microcrystalline cellulose. In some embodiments, the solid dosage form comprises the binding agent in a concentration of from about 8% to about 15% by weight of the dosage form. In some embodiments, the solid dosage form comprises the binding agent in a concentration of from about 10% to about 12% by weight of the dosage form. Microcrystalline cellulose, a processed cellulose, has been utilized extensively in the pharmaceutical industry as a direct compression vehicle for solid dosage forms. Microcrystalline cellulose is commercially available in several grades which range in average particle size from 20 to 200 microns such as under the tradename EMCOCEL™ (Penwest Pharmaceuticals Co. Patterson, N.Y.) and as AVICEL™ (FMC BioPolymer, Philadelphia, Pa.). Typically, microcrystalline cellulose has an apparent density of about 0.28 g/cm.sup.3 to about 0.34 g/cm$^3$ and a tap density of about 0.35 g/cm$^3$ to about 0.48 g/cm$^3$ (pages 108-111, Handbook of Pharmaceutical Excipients, 4th Ed., Pharmaceutical Press and The American Pharmaceutical Association, 2003).

In some embodiments, the oral dosage forms further comprise a disintegrant. In some preferred embodiments, the disintegrant is selected from the group consisting of crospovidone, croscarmellose sodium, and sodium starch glycolate. Dissolution of the oral dosage forms of the present invention may be analyzed by standard USP procedures. In some embodiments, the dissolution of the dosage form in a medium containing demineralized water as a solvent is greater than 75 percent at about 10 minutes where the tablet is raised and lowered in said solvent at a constant frequency rate between 29 and 32 cycles per minute, through a distance of 55±2 mm. In some embodiments, the disintegrant is provided in a concentration of from about 2% to about 8% by weight of the dosage form.

In some embodiments, the solid dosage form is a tablet. In some embodiments, the hardness of the tablets is determined by standard USP protocols and expressed as Newtons (N). In some embodiments, tablets have a hardness of greater than about 60 N, 70N, 80N, 90N or 95N. In some embodiments, the tablets have a hardness of from about 80 to about 100 N or from about 90N to 100N.

In some embodiments, the present inventions provides processes for preparation of krill powder tablets comprising granulating an inner phase, mixing the inner phase with pharmaceutically acceptable excipients, and compressing the obtained mixture. In some embodiments, the inner phase comprises the krill powder and one or pharmaceutically acceptable excipients. In some embodiments, the inner phase preferably comprises from about 70 to about 85% krill powder by weight of the inner phase. In some preferred embodiments, the inner phase preferably comprises from about 12 to about 20 percent of an adsorption agent by weight of the inner phase, for example magnesium aluminometasilicate. A variety of granulation liquids may be utilized, for example water or ethanol. In some embodiments, the inner phase further comprises a binding agent, for example HPC or PVP or combinations thereof, in an amount of from about 1% to about 10% by weight of the inner phase. In some embodiments, the inner phase is mixed with an outer phase. In some embodiments, the outer phase comprises one or more pharmaceutically acceptable agents. In some embodiments, the outer phase comprises one or more adsorption agents, for example magnesium aluminometasilicate. In some embodiments, the outer phase further comprises one or more binding agents, such as AVICEL™ PH 102, PVP or HPC. In some embodiments, the outer phase further comprises a disintegrant, such as crospovidone, croscarmellose sodium, or sodium starch glycolate. In some embodiments, the adsorption agent is included in the outer phase in an amount of about 30 to 50 percent by weight of the outer phase, the binding agent is included in the outer phase in an amount of about 30 to 50 percent by weight of the outer phase, and the disintegrant is included in the outer phase in an amount of about 10 to 30 percent by weight of the outer phase.

In some embodiments, the tablets are coated. In some embodiments, the coating is a water soluble coating. Suitable water soluble coatings include, but are not limited to, water soluble cellulose acetate, hypromellose (HPMC), microcrystalline cellulose (MCC) methyl cellulose, Sepifilm™ 050 and Sepisperse™ Dry (mixtures of MCC and HPMC), hydroxypropyl cellulose, ethyl cellulose, PVP, and enteric coating polymers such as cellulose acetate phthalate, methacrylic acid copolymers that are soluble in the small intestine but not in the low pH of the stomach.

The dietary supplements of the present invention may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: ascorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In further embodiments, the compositions comprise at least one food flavoring such as acetaldehyde (ethanal), acetoin (acetyl methylcarbinol), anethole (parapropenyl anisole), benzaldehyde (benzoic aldehyde), N butyric acid (butanoic acid), d or l carvone (carvol), cinnamaldehyde (cinnamic aldehyde), citral (2,6 dimethyloctadien 2,6 al 8, geranial, neral), decanal (N decylaldehyde, capraldehyde, capric aldehyde, caprinaldehyde, aldehyde C 10), ethyl acetate, ethyl butyrate, 3 methyl 3 phenyl glycidic acid ethyl ester (ethyl methyl phenyl glycidate, strawberry aldehyde, C 16 aldehyde), ethyl vanillin, geraniol (3,7 dimethyl 2,6 and 3,6 octadien 1 ol), geranyl acetate (geraniol acetate), limonene (d, l, and dl), linalool (linalol, 3,7 dimethyl 1,6 octadien 3 ol), linalyl acetate (bergamol), methyl anthranilate (methyl 2 aminobenzoate), piperonal (3,4 methylenedioxy benzaldehyde, heliotropin), vanillin, alfalfa (*Medicago sativa* L.), allspice (*Pimenta officinalis*), ambrette seed (*Hibiscus abelmoschus*), angelic (*Angelica archangelica*), Angostura (*Galipea officinalis*), anise (*Pimpinella anisum*), star anise (*Illicium verum*), balm (*Melissa officinalis*), basil (*Ocimum basilicum*), bay (*Laurus nobilis*), calendula (*Calendula officinalis*), (*Anthemis nobilis*), capsicum (*Capsicum frutescens*), caraway (*Carum carvi*), cardamom (*Elettaria cardamomum*), cassia, (*Cinnamomum cassia*), cayenne pepper (*Capsicum frutescens*), Celery seed (*Apium graveolens*), chervil (*Anthriscus cerefolium*), chives (*Allium schoenoprasum*), coriander (*Coriandrum sativum*), cumin (*Cuminum cyminum*), elder flowers (*Sambucus canadensis*), fennel (*Foeniculum vulgare*), fenugreek (*Trigonella foenum graecum*), ginger (*Zingiber officinale*), horehound (*Marrubium vulgare*), horseradish (*Armoracia lapathifolia*), hyssop (*Hyssopus officinalis*), lavender (*Lavandula officinalis*), mace (*Myristica fragrans*), marjoram (*Majorana hortensis*), mustard (*Brassica nigra, Brassica juncea, Brassica hirta*), nutmeg (*Myristica fragrans*), paprika (*Capsicum annuum*), black pepper (*Piper nigrum*), peppermint (*Mentha piperita*), poppy seed (*Papayer somniferum*), rosemary (*Rosmarinus officinalis*), saffron (*Crocus sativus*), sage (*Salvia officinalis*), savory (*Satureia hortensis, Satureia montana*), sesame (*Sesamum indicum*), spearmint (*Mentha spicata*), tarragon (*Artemisia dracunculus*), thyme (*Thymus vulgaris, Thymus serpyllum*), turmeric (*Curcuma longa*), vanilla (*Vanilla planifolia*), zedoary (*Curcuma zedoaria*), sucrose, glucose, saccharin, sorbitol, mannitol, aspartame. Other suitable flavoring are disclosed in such references as Remington's Pharmaceutical Sciences, 18th Edition, Mack Publishing, p. 1288-1300 (1990), and Furia and Pellanca, Fenaroli's Handbook of Flavor Ingredients, The Chemical Rubber Company, Cleveland, Ohio, (1971), known to those skilled in the art.

In other embodiments, the compositions comprise at least one synthetic or natural food coloring (e.g., annatto extract, astaxanthin, beet powder, ultramarine blue, canthaxanthin, caramel, carotenal, beta carotene, carmine, toasted cottonseed flour, ferrous gluconate, ferrous lactate, grape color extract, grape skin extract, iron oxide, fruit juice, vegetable juice, dried algae meal, tagetes meal, carrot oil, corn endosperm oil, paprika, paprika oleoresin, riboflavin, saffron, tumeric, tumeric and oleoresin).

In still further embodiments, the compositions comprise at least one phytonutrient (e.g., soy isoflavonoids, oligomeric proanthcyanidins, indol 3 carbinol, sulforaphone, fibrous ligands, plant phytosterols, ferulic acid, anthocyanocides, triterpenes, omega 3/6 fatty acids, conjugated fatty acids such as conjugated linoleic acid and conjugated linolenic acid, polyacetylene, quinones, terpenes, cathechins, gallates, and quercitin). Sources of plant phytonutrients include, but are not limited to, soy lecithin, soy isoflavones, brown rice germ, royal jelly, bee propolis, acerola berry juice powder, Japanese green tea, grape seed extract, grape skin extract, carrot juice, bilberry, flaxseed meal, bee pollen, *ginkgo biloba*, primrose (evening primrose oil), red clover, burdock root, dandelion, parsley, rose hips, milk thistle, ginger, Siberian ginseng, rosemary, curcumin, garlic, lycopene, grapefruit seed extract, spinach, and broccoli.

In still other embodiments, the compositions comprise at least one vitamin (e.g., vitamin A, thiamin (B1), riboflavin (B2), pyridoxine (B6), cyanocobalamin (B12), biotin, ascorbic acid (vitamin C), retinoic acid (vitamin D), vitamin E, folic acid and other folates, vitamin K, niacin, and pantothenic acid). In some embodiments, the particles comprise at least one mineral (e.g., sodium, potassium, magnesium, calcium, phosphorus, chlorine, iron, zinc, manganese, flourine, copper, molybdenum, chromium, selenium, and iodine). In some particularly preferred embodiments, a dosage of a plurality of particles includes vitamins or minerals in the range of the recommended daily allowance (RDA) as specified by the United States Department of Agriculture. In still other embodiments, the particles comprise an amino acid supplement formula in which at least one amino acid is included (e.g., 1-carnitine or tryptophan).

In further embodiments, the present invention provide animal feeds comprising one or more the compositions described in detail above. The animal feeds preferably form a ration for the desired animal and is balanced to meet the animals nutritional needs. The compositions may be used in the formulation of feed or as feed for animals such as fish, including fish fry, poultry, cattle, pigs, sheep, shrimp and the like.

Example 1

Four portions of krill were analysed for dry matter, fat, and protein. Most of the variation in the composition can be expected to be due to variation in the sampling. To include the effect of variation in storage time after thawing, raw material samples were also taken at different times during the working day. The observed variation in raw material input is inherent in all calculations of fat, dry matter and protein distributions based on the reported examples.

TABLE 1

Composition of krill (g/100 g)

| | Dry matter | Fat | Fat free dry matter | Protein |
|---|---|---|---|---|
| Krill 1 | 21.40 | 7.80 | 13.60 | 11.80 |
| Krill 2 | 22.13 | 7.47 | 14.66 | 12.96 |
| Krill 3 | 23.78 | 7.44 | 16.34 | 14.60 |
| Krill 4 | 23.07 | 7.55 | 15.52 | 13.83 |
| Mean | 22.60 | 7.57 | 15.03 | 13.30 |
| SD | 1.04 | 0.16 | 1.17 | 1.20 |
| RSD | 4.6% | 2.2% | 7.8% | 9.0% |

Example 2

In this example a novel method for preparing krill meal was investigated. 800 g of preheated water (95-100° C.) and 200 g of frozen krill (0° C.) were mixed in a cooker (cooker 1) at a temperature of 75° C. for 6 minutes. Next, the heated krill and the hot water were separated by filtration. The preheated krill was further cooked (cooker 2) by mixing with 300 g hot water (95° C.) in a kitchen pan and kept at 90° C. for 2 minutes before separation over a sieve (1.0×1.5 mm opening). The heated krill was separated from the liquid and transferred to a food mixer and cut for 10 seconds. The disintegrated hot krill was added back to the hot water and centrifuged at 8600×g (RCF average) for 10 minutes. The supernatant corresponding to a decanter liquid (Dl) was decanted off. The liquid from cooking step 1 was heated to 95-100° C. to coagulate the extracted protein. The coagulum was separated over a sieve (1.0×1.5 mm opening) and a weight of 40 g was found. FIG. 1 shows an overview of the process of making krill meal with a two stage cooking process.

Example 3

The total volatile nitrogen (TVN), trimethylamine (TMA) and trimethylamine oxide (TMAO) content were determined in the four products from the cooking test in example 2 (Table 2). The krill was fresh when frozen, so no TMA was detected in the products. The results show that TMAO is evenly distributed in the water phase during cooking of krill.

TABLE 2

Distribution of total volatile nitrogen (TVN), trimethylamine (TMA) and trimethylamine oxide (TMAO) in the products from the cooking procedure.
Products from test no. 10

|  |  | Krill | Coagulum from cooker | Coagulated cooker liquid | Decanter solids | Decanter liquid | SUM |
|---|---|---|---|---|---|---|---|
| Weight (wb) | g | 200 | 97.6 | 711.1 | 90.3 | 294.7 |  |
| Dry matter | g/100 g | 21.4 | 14.2 | 1.0 | 22.2 | 0.9 |  |
| Analytical values |  |  |  |  |  |  |  |
| Total volatile nitrogen | mg N/100 g | 8 | 1.3 | 1.2 | 2.3 | 1 |  |
| Trimetylamine-N | mg N/100 g | <1 | <1 | <1 | <1 | <1 |  |
| Trimetylamine oxid-N | mg N/100 g | 107 | 19.2 | 13.5 | 10.4 | 13.1 |  |
| Quantities |  |  |  |  |  |  |  |
| Total volatile nitrogen | mg N | 15.0 | 1.3 | 8.5 | 2.1 | 2.9 | 14.8 |
| Trimetylamine-N | mg N | — | — | — | — | — | — |
| Trimetylamine oxid-N | mg N | 214 | 18.7 | 96.0 | 9.4 | 38.6 | 163 |
| Distribution |  |  |  |  |  |  |  |
| Total volatile nitrogen | % of input | 100% | 8% | 57% | 14% | 20% | 99% |
| Trimetylamine-N | % of input |  |  |  |  |  |  |
| Trimetylamine oxid-N | % of input | 100% | 9% | 45% | 4% | 18% | 76% |

In addition, fat, dry matter and astaxanthin were determined in the products (Table 3). It was observed that the major part of the astaxanthin in the krill was found in the press cake (Table 3). Only a minor part is found in the coagulum which contains more than 60% of the lipid in the krill raw material. The cooking procedure with leaching of a protein-lipid emulsion increases the concentration of astaxanthin in the remaining fat. The results also show that the water free coagulum contains approximately 40% dry matter and 60% fat. The dry matter consist of mostly protein.

TABLE 3

Distribution of astaxanthin in the products from the cooking procedure.
Products from test no. 10

|  |  | Krill | Coagulum from cooker | Coagulated cooker liquid | Decanter solids | Decanter liquid | SUM |
|---|---|---|---|---|---|---|---|
| Weight (wb) | g | 200 | 97.6 | 711.1 | 90.3 | 294.7 |  |
| Fat | g/100 g | 7.8 | 10.3 | 0.1 | 5.3 | 0.2 |  |
| Fat free dry matter | g/100 g | 13.6 | 3.9 | 0.9 | 16.9 | 0.8 |  |

TABLE 3-continued

Distribution of astaxanthin in the products from the cooking procedure.
Products from test no. 10

|  |  | Krill | Coagulum from cooker | Coagulated cooker liquid | Decanter solids | Decanter liquid | SUM |
|---|---|---|---|---|---|---|---|
| Analytical values |  |  |  |  |  |  |  |
| Fri Astaxanthin | mg/kg | 3 | <1 | <1 | 4.5 | <1 |  |
| Astaxanthin esters | mg/kg | 33 | 1.2 | <0.02 | 59 | 0.18 |  |
| Conc. in lipid |  |  |  |  |  |  |  |
| Fri Astaxanthin | mg/kg lipid | 38 | — | — | 85 | — |  |
| Astaxanthin esters | mg/kg lipid | 423 | 12 | — | 1111 | 113 |  |
| Quantities |  |  |  |  |  |  |  |
| Free Astaxanthin | mg | 0.6 | — | — | 0.4 | — | 0.4 |
| Astaxanthin esters | mg | 6.6 | 0.1 | — | 5.3 | 0.1 | 6.2 |
| Distribution |  |  |  |  |  |  |  |
| Free Astaxanthin | % of input | 100% | — | — | 68% | — | 68% |
| Astaxanthin esters | % of input | 100% | 2% | — | 81% | 1% | 83% |

The coagulum from the cooking experiment in Example 2 were analysed for lipid classes. The coagulum lipid was dominated by triacylglycerol and phosphatidyl choline with a small quantity of phosphatidyl ethanolamine (Table 4).

TABLE 4

Distribution of lipid classes in the coagulum from cooking experiments.

| Experiment |  | Krill | Coagulum F5 | Coagulum F6 |
|---|---|---|---|---|
| Fat (Bligh & Dyer) | g/100 g sample | 7.8 | 11.8 | 9.9 |
| Triacylglycerol | g/100 g fat | 47 | 40 | 50 |
| Diacylglycerol | g/100 g fat | <0.5 | 1 | 0.7 |
| Monocylglycerol | g/100 g fat | <1 | <1 | <1 |
| Free fatty acids | g/100 g fat | 12 | 0.2 | 0.4 |
| Cholesterol | g/100 g fat | 0.3 | <0.3 | <0.3 |
| Cholesterol esters | g/100 g fat | 0.8 | <0.3 | <0.3 |
| Phosphatidyl ethanolamine | g/100 g fat | 5.3 | 2.3 | 2.2 |
| Phosphatidyl inositol | g/100 g fat | <1 | <1 | <1 |
| Phosphatidyl serine | g/100 g fat | <1 | <1 | <1 |
| Phosphatidyl choline | g/100 g fat | 33 | 43.1 | 42.3 |
| Lyso-Phosphatidyl choline | g/100 g fat | 2.4 | <1 | <1 |
| Total polar lipids | g/100 g fat | 41.3 | 45.5 | 44.5 |
| Total neutral lipids | g/100 g fat | 61.0 | 41.3 | 51.2 |
| Sum lipids | g/100 g fat | 102.3 | 86.8 | 95.7 |

The proportion of phosphatidyl choline increased from 33% in krill to 42-46% in the coagulum. The other phospholipids quantified, phosphatidyl ethanolamine and lyso-phosphatidyl choline, had lower concentrations in the coagulum than in krill. The free fatty acids were almost absent in the coagulum.

The cooking time in test F5 was 6.75 min, in test F6 it was 4.00 min. The results in Table 4 show no dependence of the distribution of the lipid classes with the cooking time.

The amino acid composition of the coagulum is not much different the amino acid composition in krill. There seems to be a slight increase in the apolar amino acids in the coagulum compared to krill (Table 5). For a protein to have good emulsion properties it is the distribution of amino acids within the protein that is of importance more than the amino acid composition.

TABLE 5

Amino acids in coagulum from cooking Example 2.

|  |  | Coagulum F 10-2 March/April 2007 | Coagulum 70-100° C. 24 Jun. 2006 | Krill 24 Jun. 2006 |
|---|---|---|---|---|
| Aspartic acid | g/100 g protein | 8.8 | 10.8 | 7.8 |
| Glutamic acid | g/100 g protein | 10.1 | 11.6 | 10.7 |
| Hydroxiproline | g/100 g protein | <0.10 | <0.10 | <0.10 |
| Serine | g/100 g protein | 4.3 | 4.6 | 3.0 |
| Glycine | g/100 g protein | 3.7 | 3.4 | 4.1 |
| Histidine | g/100 g protein | 1.7 | 1.6 | 1.6 |
| Arginine | g/100 g protein | 4.4 | 4.4 | 5.7 |
| Threonine | g/100 g protein | 5.2 | 5.6 | 3.4 |
| Alanine | g/100 g protein | 4.7 | 4.6 | 4.7 |
| Proline | g/100 g protein | 4.2 | 4.3 | 3.9 |
| Tyrosine | g/100 g protein | 4.3 | 4.7 | 2.7 |
| Valine | g/100 g protein | 6.4 | 6.6 | 4.2 |
| Methionine | g/100 g protein | 2.1 | 2.1 | 2.4 |
| Isoleucine | g/100 g protein | 8.0 | 8.5 | 4.5 |
| Leucine | g/100 g protein | 10.8 | 11.6 | 6.7 |
| Phenylalanine | g/100 g protein | 4.3 | 4.3 | 3.6 |
| Lysine | g/100 g protein | 7.5 | 8.2 | 6.2 |
| Cysteine/Cystine | g/100 g protein | 0.75 |  |  |

TABLE 5-continued

Amino acids in coagulum from cooking Example 2.

| | | Coagulum F 10-2 March/April 2007 | Coagulum 70-100° C. 24 Jun. 2006 | Krill 24 Jun. 2006 |
|---|---|---|---|---|
| Tryptophan | g/100 g protein | 0.63 | | |
| Sum amino acids | | 91.9 | 96.9 | 75.2 |
| Polar amino acids | | 47% | 48% | 51% |
| Apolar amino acids | | 53% | 52% | 49% |

The fatty acid profile of the coagulum is presented in Table 6. The content of EPA (20:5) is about 12.4 g/100 g extracted fat and the content of DHA (22:6) is about 5.0 g/100 g extracted fat.

TABLE 6

Fatty acid content of coagulum

| Fatty acid | Unit | Amount |
|---|---|---|
| 14:0 | g/100 extracted fat | 11.5 |
| 16:0 | g/100 extracted fat | 19.4 |
| 18:0 | g/100 extracted fat | 1.1 |
| 20:0 | g/100 extracted fat | <0.1 |
| 22:0 | g/100 extracted fat | <0.1 |
| 16:1 n-7 | g/100 extracted fat | 7.0 |
| 18:1 (n-9) + (n-7) + (n-5) | g/100 extracted fat | 18.4 |
| 20:1 (n-9) + (n-7) | g/100 extracted fat | 1.3 |
| 22:1 (n-11) + (n-9) + (n-7) | g/100 extracted fat | 0.8 |
| 24:1 n-9 | g/100 extracted fat | 0.1 |
| 16:2 n-4 | g/100 extracted fat | 0.6 |
| 16:3 n-4 | g/100 extracted fat | 0.2 |
| 16:4 n-4 | g/100 extracted fat | <0.1 |
| 18:2 n-6 | g/100 extracted fat | 1.2 |
| 18:3 n-6 | g/100 extracted fat | 0.1 |
| 20:2 n-6 | g/100 extracted fat | <0.1 |
| 20:3 n-6 | g/100 extracted fat | <0.1 |
| 20:4 n-6 | g/100 extracted fat | 0.2 |
| 22:4 n-6 | g/100 extracted fat | <0.1 |
| 18:3 n-3 | g/100 extracted fat | 0.8 |
| 18:4 n-3 | g/100 extracted fat | 2.5 |
| 20:3 n-3 | g/100 extracted fat | <0.1 |
| 20:4 n-3 | g/100 extracted fat | 0.4 |
| 20:5 n-3 | g/100 extracted fat | 12.4 |
| 21:5 n-3 | g/100 extracted fat | 0.4 |
| 22:5 n-3 | g/100 extracted fat | 0.3 |
| 22:6 n-3 | g/100 extracted fat | 5.0 |

Example 4

To evaluate the two stage cooking process described above, a laboratory scale test was performed. The tests are described below.

Materials and Methods

Raw material. Frozen krill were obtained by Aker Biomarine and 10 tons were stored at Norway Pelagic, Bergen, and retrieved as required. The krill was packed in plastic bags in cardboard boxes with 2×12.5 kg krill. The boxes with krill were placed in a single layer on the floor of the process plant the day before processing. By the time of processing the krill varied from +3° C. to −3° C.

Analytical methods.

Protein, Kjeldahl's method: Nitrogen in the sample is transformed to ammonium by dissolution in concentrated sulfuric acid with cupper as catalyst. The ammonia is liberated in a basic distillation and determined by titration, (ISO 5983:1997(E), Method A 01). Uncertainty: 1%.

Protein, Combustion: Liberation of nitrogen by burning the sample at high temperature in pure oxygen. Detection by thermal conductivity. Percent protein in the sample is calculated by a multiplication of analysed percent nitrogen and a given protein factor, (AOAC Official Method 990.03, 16th ed. 1996, Method A 25).

Moisture: Determination of the loss in mass on drying at 103° C. during four hours (ISO 6496 (1999). Method A 04). Uncertainty: 4%.

Ash: Combustion of organic matter at 550° C. The residue remaining after combustion is defined as the ash content of the sample. (ISO 5984:2002. Method A 02). Uncertainty: 3%.

Fat, Ethyl acetate extraction: Absorption of moisture in wet sample by sodium sulphate, followed by extraction of fat by ethyl acetate (NS 9402, 1994 (modified calculation). Method A 29).

Fat, Soxhlet: Extraction of fat by petroleum ether. Mainly the content of triglycerides is determined, (AOCS Official Method Ba 3-38 Reapproved 1993. Method A 03).

Fat, Bligh and Dyer: Extraction of fat by a mixture of chloroform, methanol, and water in the proportion 1:2:0.8 which build a single phase system. Addition of chloroform and water gives a chloroform phase with the lipids and a water/methanol phase. The lipids are determined in an aliquot of the chloroform phase after evaporation and weighing. The extraction includes both triglycerides and phospholipids. (E. G. Bligh & W. J. Dyer: A rapid method of total lipid extraction and purification. Can. J. Biochem. Physiol. Vol 37 (1959). Metode A 56).

Astaxanthin: Extraction with ethanol and di-chloromethane. Polar products are removed by open column chromatography on silica gel. Isomers are separated on normal phase HPLC on Si 60 column and detection at 470 nm. (Schierle J. & Härdi W. 1994. Determination of stabilized astaxanthin in Carophyll® Pink, premixes and fish feeds. Edition 3. Revised Supplement to: Hoffman P, Keller H E, Schierle J., Schuep W. Analytical methods for vitamins and carotenoids in feed. Basel: Department of Vitamin Research and Development, Roche. Method A 23)

Moisture in oil: Determination of actual water content of fats and oils by titration with Karl Fischer reagent, which reacts quantitatively with water, (AOCS Official Method CA 2e-84. Reapproved 1993. Method A 13).

Dry matter in stick water during processing is correlated to refract meter which gives ° Brix. Amino acids were determined as urea derivatives by reversed phase HPLC with fluorescence detection. (Cohen S. A. and Michaud D. P., Synthesis of a Fluorescent Derivatizing Reagent, 6-Aminoquinolyl-N-Hydroxysuccinimidyl Carbamate, and Its Application for the Analysis of Hydrolysate Amino Acids via High-Performance Liquid Chromatography. Analytical Biochemistry 211, 279-287, 1993. Method A42). TVB-N, TMA-N and TMAO-N were determined in a 6% trichloro-acetic acid extract by micro diffusion and titration. (Conway, E. I., and A. Byrne. An absorption apparatus for the micro determination of certain volatile substances. Biochem. J. 27:419-429, 1933, and Larsen, T, SSF rapport nr. A-152, 1991). Fatty acids were determined by esterifying the fatty acids to methyl esters, separate the esters by GLC, and quantify by use of C23:0 fatty acid methyl ester as internal standard. (AOCS Official Method Ce 1b-89, Method A 68). Lipids were separated by HPLC and detected with a Charged Aerosol Detector. Vitamins A, D and E were analysed at AnalyCen, Kambo.

Results and Discussion

Raw material of krill. Table 7 gives the results of analysis of the raw material of the krill that was used in the pilot trials. Besides the first trial, the same shipment of krill was used for all trials. The dry matter was about 21-22%, fat 6%, protein 13-14%, salt 1% pH, total volatile nitrogen (TVN) 18 mgN/100 g, trimethylamine (TMA) 4 mg N/100 g and trimethylamineoxide (TMAO) 135 mg N/100 g. Compared to fish pH, TMAO and salt (Cl—) is high for krill.

TABLE 7

Analysis of raw krill on wet base (wb)
Sample: Raw material of krill

| Analysis: Date: | Dry matter g/100 g | Fat, B&D g/100 g | Protein g/100 g | Ash g/100 g | Salt g/100 g | pH | TVN mg N/100 g | TMA mg N/100 g | TMAO mg N/100 g | Marks |
|---|---|---|---|---|---|---|---|---|---|---|
| Aug. 08, 2007 | 22.8 | 7.1 | 13.5 | 2.5 | | | | | | Saga Sea 04.07.06 Lot. L1 |
| Sep. 18, 2007 | 21.3 | 6.0 | | | | | | | | |
| Oct. 04, 2007 | 21.6 | 6.3 | 13.5 | | | | | | | Krillråstoff CO5S |
| Oct. 04, 2007 | 20.5 | 5.9 | 12.8 | | | | | | | Krillråstoff AO6S |
| Oct. 25, 2007 | 22.1 | 6.0 | 13.9 | 2.9 | 1.1 | 7.4 | 20.8 | 5.8 | 128.3 | Krillråstoff CO5S |
| Oct. 25, 2007 | 21.3 | 6.0 | 13.2 | 2.7 | 1.1 | 7.4 | 15.0 | 2.3 | 140.6 | Krillråstoff AO6S |
| Nov. 22, 2007 | 21.9 | 5.9 | | | | 7.8 | 17.9 | 3.5 | 123.7 | |
| Average | 21.6 | 6.2 | 13.5 | 2.7 | 1.1 | 7.4 | 17.9 | 4.0 | 134.5 | |

Table 8 gives the analysis of raw krill on dry base. If these figures are multiplied with 0.93 it will give the figures on meal base with 7% water.

TABLE 8

Analysis of raw krill on dry base (db)
Sample: Raw material of krill

| Analysis: Date: | Dry matter g/100 g | Fat, B&D g/100 g | Protein g/100 g | Ash g/100 g | Salt g/100 g | TVN mg N/100 g | TMA mg N/100 g | TMAO mg N/100 g |
|---|---|---|---|---|---|---|---|---|
| Aug. 07, 2007 | 100 | 31.1 | 59.2 | 11.0 | | | | |
| Sep. 18, 2007 | 100 | 28.2 | | 0.0 | | | | |
| Oct. 04, 2007 | 100 | 29.2 | 62.5 | 0.0 | | | | |
| Oct. 04, 2007 | 100 | 28.8 | 62.4 | 0.0 | | | | |
| Oct. 25, 2007 | 100 | 27.1 | 62.9 | 13.1 | 5.0 | 94.1 | 26.1 | 580.5 |
| Oct. 25, 2007 | 100 | 28.2 | 62.0 | 12.7 | 5.2 | 70.6 | 10.9 | 660.2 |
| Nov. 22, 2007 | 100 | 26.9 | | | | 81.7 | 16.0 | 564.8 |
| Average | 100 | 28.5 | 62.5 | 12.3 | 5.1 | 82.4 | 18.5 | 620.4 |

Separation of coagulum and pressing for krill oil. 99 kg krill was processed by adding batches of 20 kg krill to 80 l of water at 95° C. in a steam heated kettle (200 l). The steam on the kettle was closed, and the krill and water were gently mixed manually for 3 minutes, and the mixed temperature became 75° C. (heating step no. 1). The heated krill was separated from the water by sieving. Sieved preheated krill (75° C.) was added 20 kg hot water and heated to 85° C. within a minute, (heating step 2). The krill was sieved again and feed into the press. The liquid from step 1 (krill milk) was coagulated at 95° C. All the krill was cooked and the press liquid was separated for oil. From 99 kg krill about 0.5 kg of unpolished krill oil was separated from the press liquid. Tables 9 and 10 provide an analysis of cooked krill after first cooking step on wet base and dry base.

TABLE 9

Analysis of cooked krill on wet base (wb)
Sample: Cooked krill

| Analysis: Date: | Dry matter g/100 g | Fat, B&D g/100 g | Protein g/100 g | Ash g/100 g | pH | TVN mg N/100 g | TMA mg N/100 g | TMAO mg N/100 g |
|---|---|---|---|---|---|---|---|---|
| Aug. 07, 2007 | 20.2 | 4.7 | 13.5 | 2.2 | | | | |
| Sep. 18, 2007 | 19.8 | 4.6 | | | | | | |
| Oct. 25, 2007 | 15.2 | 3.2 | 10.3 | 2.0 | 8.2 | 10.5 | 3.5 | 75.4 |

TABLE 10

Analysis of cooked krill on dry base (db)
Sample: Cooked krill

| Analysis: Date: | Dry matter g/100 g | Fat, B&D g/100 g | Protein g/100 g | Ash g/100 g | TVN mg N/100 g | TMA mg N/100 g | TMAO mg N/100 g |
|---|---|---|---|---|---|---|---|
| Aug. 07, 2007 | 100.0 | 23.3 | 66.8 | 10.9 | | | |
| Sep. 18, 2007 | 100 | 23.2 | | | | | |
| Oct. 25, 2007 | 100 | 21.1 | 67.8 | 13.2 | 69.3 | 23.1 | 496.3 |

Compared to raw krill (Table 8) there is a reduction in dry matter for cooked krill. The fat content in dry matter is reduced because of the fat in the krill milk which is separated from the cooked krill. The content of protein is increased on dry base, but the ash seems to be at the same level. TMAO in the krill is reduced and is found in the cooking liquid.

Micro filtration. The krill milk (70° C.) from step 1 was coagulated at >95° C. and separated from the liquid through microfiltration (Soby Miljøfilter). Coagulum was then pressed in a press and dried. Tables 11 and 12 gives analyses of coagulum on wet base and dry base. The dry matter of the coagulum was between 12.8 and 16.7%. On dry base the fat content about 60% and TMAO 340 mg N/100 g. The dry matter of the coagulum increased to 34-38% by pressing. The fat content also increased on dry base (Table 13), but the TMAO was reduced to 145 mg N/100 g. After washing the press cake with 1 part water to 1 part press cake of coagulum and then press again, the TMAO was reduced to 45 mg N/100 g on dry base (Table 18).

Figure 2:
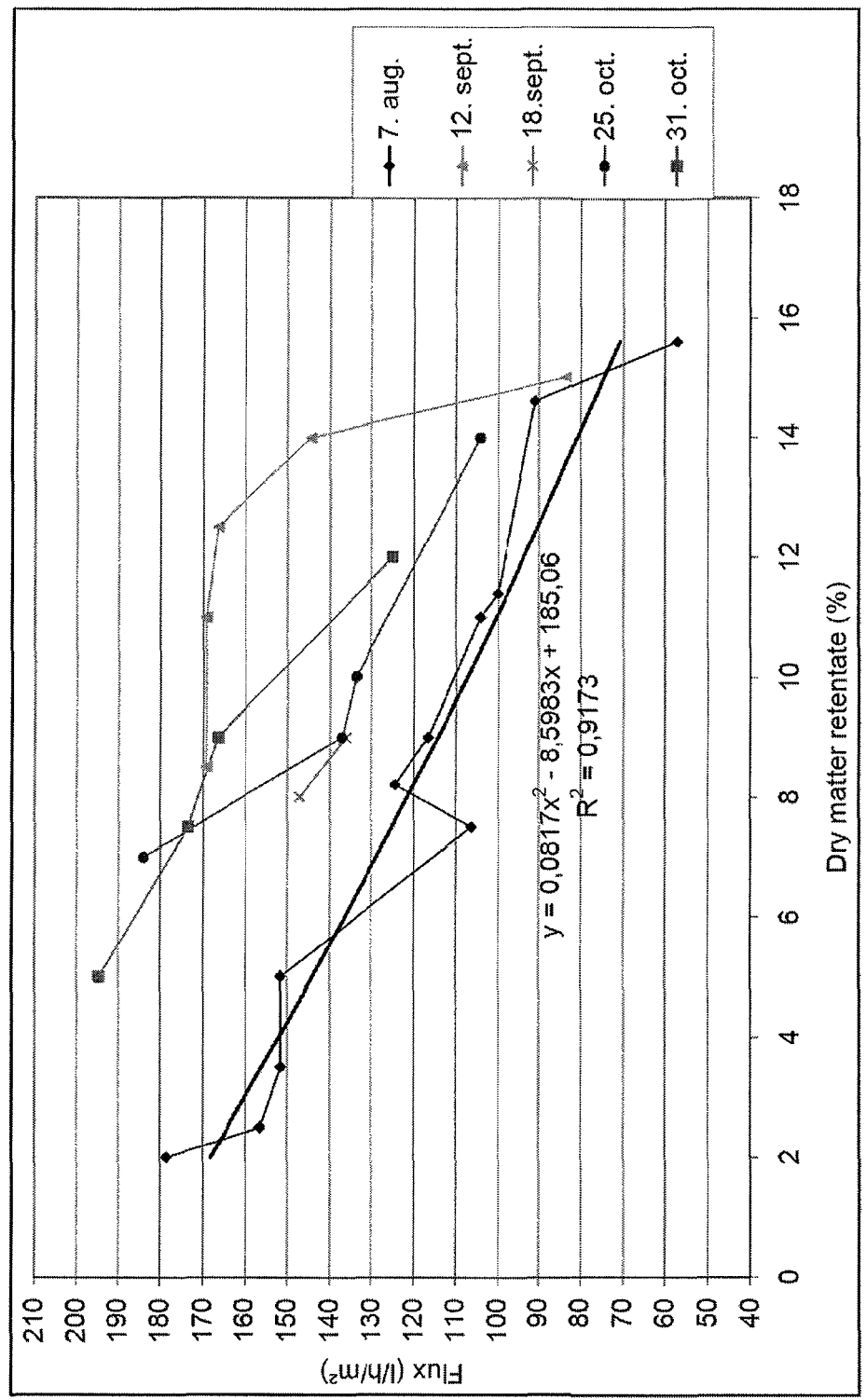
FIG. 2 is a graph of the Permeate flux as function of dry matter of the retentate (%) (° Brix).
Figure 3:
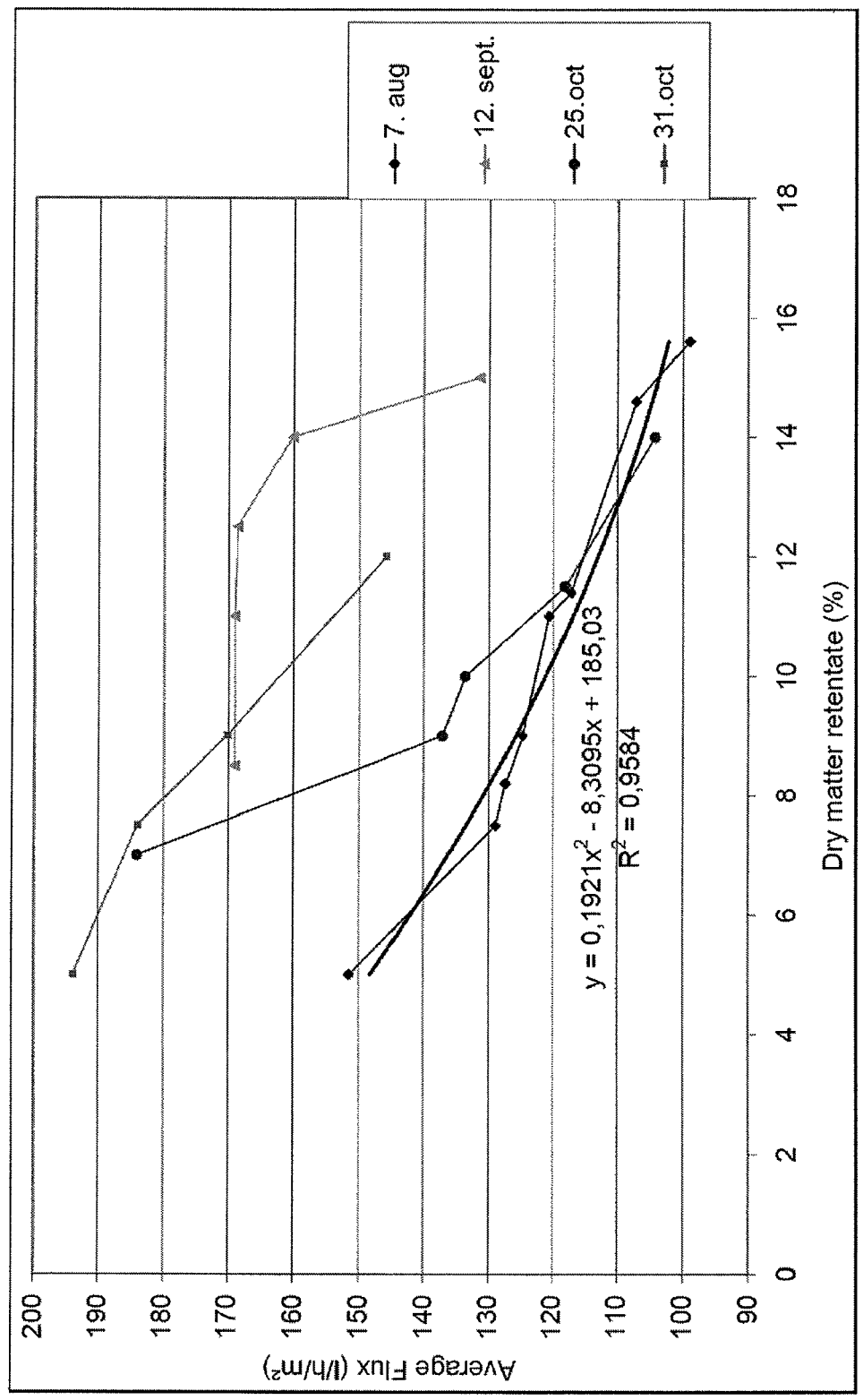
FIG. 3 is a graph of Average Flux as function of dry matter in retentate.

The opening of the micro-filter was 100 nm. 80 kg krill was processed by starting by 80 kg water (95° C.) and 20 kg krill into the kettle as described. For the first 2 batches of krill clean water was used (160 kg), but for the last 2 batches permeate from the membrane filter was used instead of water. The membrane filtration was followed with a refract meter calibrated for sugar solution (° Brix). The Brix-value is near the dry matter concentration in the process liquids. The flux value for the filter at about 60° C. was 350 l/m2/h for retentate with 7.8° Brix (refract meter) and reduced to 290 l/m2/h when the Brix value increased to 9.9°. The Brix value for the permeate was only 1° due to high dilution when the amount to be filtered is small. See FIGS. 2 and 3. The permeate was golden and transparent.

All permeate was evaporated in a kettle to >65°Brix. Retentate, 2 liter, was evaporated in a laboratory evaporator at 70° C. and 12 mm Hg. At 27.5° Brix the retentate was still flowing well. As the concentration continued the retentate

TABLE 11

Analysis of coagulum on wet base (wb)
Sample: Coagulum

| Analysis: Date: | Dry matter g/100 g | Fat, B&D g/100 g | Protein g/100 g | Ash g/100 g | TVN mg N/100 g | TMA mg N/100 g | TMAO mg N/100 g |
|---|---|---|---|---|---|---|---|
| Oct. 10, 2007 | 12.8 | 7.9 | | | | | |
| Oct. 25, 2007 | 14.3 | 8.3 | 5.4 | 1.0 | 5.9 | 2.3 | 48.6 |
| Oct. 31, 2007 | 16.7 | 9.3 | 6.2 | | | | |
| Average | 14.6 | 8.5 | 5.8 | | | | |

TABLE 12

Analysis of coagulum on dry base (db)
Sample: Coagulum

| Analysis: Date: | Dry matter g/100 g | Fat, B&D g/100 g | Protein g/100 g | Ash g/100 g | TVN mg N/100 g | TMA mg N/100 g | TMAO mg N/100 g |
|---|---|---|---|---|---|---|---|
| Oct. 10, 2007 | 100 | 61.7 | | | | | |
| Oct. 25, 2007 | 100 | 58.0 | 37.8 | 7.0 | 41.0 | 16.4 | 340.1 |
| Oct. 31, 2007 | 100 | 55.7 | 37.1 | | | | |
| Average | 100 | 58.5 | 37.4 | | | | |

TABLE 13

Analysis of press cake from coagulum on wet base
Sample: Press cake of coagulum

| Analysis: Date: | Dry matter g/100 g | Fat, B&D g/100 g | TVN mg N/100 g | TMA mg N/100 g | TMAO mg N/100 g | Raw krill worked up kg | Coagulum perss cake kg | Coagulum PK per kg raw krill kg/kg |
|---|---|---|---|---|---|---|---|---|
| Nov. 22, 2007 | 38.8 | 23.6 | 7.9 | 4.5 | 56.1 | 1000 | 54.2 | 0.0542 |
| Dec. 11, 2007 | 33.8 | 22.5 | 3.4 | 0 | 45.3 | 500 | 21.92 | 0.0438 |
| Dec. 11, 2007* | 33.6 | 21.3 | 0 | 0 | 15.3 | 500 | 15 | 0.0300 |

*After 1 wash (Press cake:water = 1:1)

Membrane filtration. Another way to collect the lipids from the krill milk is to separate by membrane filtration. For this to be possible the milk must not coagulate, but be brought to the membrane filter from the sieve (heating step no. 1).

Before the krill milk could enter the membrane filter the milk is pre-filtrated, which was done by the sieve (100 μm).

became more and more viscous, first as a paste and finely to a dry mass. The concentrated retentate (27° Brix), permeate (>65° Brix) and dry retentate were analyzed and the results are given in Table 14 on sample base (% wb) and Table 15 on dry matter base (% db) (sample no 1, 2 and 3). A sample of coagulum was dried as for the retentate (sample no 4).

TABLE 14

Analysis of concentrate from retentate, permeate and coagulum on wet base (wb)

| Sample | Dry matter % wb | Fat (polar + apolar) Bligh & Dyer % wb | Crude Protein % wb | Ash % wb | TVN mg N/ 100 g wb | TMA mg N/ 100 g wb | TMAO mg N/ 100 g wb | Water activity 25° C. aw |
|---|---|---|---|---|---|---|---|---|
| No. 1 Concentrate of retentat | 26.0 | 16.3 | 9.5 | 1.6 | 5.7 | <1 | 99 | 0.978 |
| No. 2 Consentrate of permeat | 72.7 | 1.0 | 51.1 | 24.7 | 138 | 110 | 1 157 | 0.385 |
| No. 3 Vakuum dried retentate | 64.9 | 39.3 | 24 | 4.1 | 12.8 | 29.4 | 196 | 0.875 |
| No. 4 Vakuum died coagulum | 60.3 | 37.1 | 20.9 | 4.4 | 52.9 | 28.1 | 216 | 0.912 |

TABLE 15

Analysis of concentrate from retentate, permeate and coagulum on dry matter base (db)

| Sample | Dry matter % db | Fat (polar + apolar) Bligh & Dyer % db | Crude Protein % db | Ash % db | TVN mg N/100 g db | TMA mg N/100 g db | TMAO mg N/100 g db |
|---|---|---|---|---|---|---|---|
| No. 1 Concentrate of retentat | 100.0 | 62.7 | 36.5 | 6.2 | 21.9 | <1 | 382 |
| No. 2 Consentrate of permeat | 100.0 | 1.4 | 70.3 | 34.0 | 190 | 152 | 1 592 |
| No. 3 Vakuum dried retentate | 100.0 | 60.6 | 37.0 | 6.3 | 19.7 | 45.3 | 302 |
| No. 4 Vakuum died coagulum | 100.0 | 61.5 | 34.7 | 7.3 | 87.7 | 46.6 | 358 |

These results indicate that micro filtration of krill milk was promising and is an alternative to coagulate the krill milk. The protein portion was high in taurine. The content of fat, protein, ash and TMAO were almost similar between retentate and coagulum. Permeate can be concentrated to 70% dry matter and will have a water activity below 0.4 at 25° C. which means that it can be stored at ambient temperature.

Press cake and press liquid. Tables 16 and 17 provide an analysis of press cake on wet and dry base from the different trials. The average amount of press cake per kg raw krill was found to be 0.23 kg. The dry matter of the press cake was between 44 and 48%. The fat content in dry matter was reduced from 21% before to 15-20% after pressing. This will give a press cake meal from 14 to 18.5% fat, about 67% protein and 7% moisture. TMAO was reduced from about 500 mg N/100 g dry matter in cooked krill to 95 mg N/100 g dry matter in the press cake.

TABLE 16

Analysis on wet base (wb) of press cake and calculations

| Sample: Analysis: Date: | Press cake Dry matter g/100 g | Fat, B&D g/100 g | Protein g/100 g | TVN mg N/100 g | TMA mg N/100 g | TMAO mg N/100 g | Raw krill worked up kg | Press cake kg | Kg press cake per kg raw krill kg/kg |
|---|---|---|---|---|---|---|---|---|---|
| Sep. 18, 2007 | 48.1 | 8.0 | | | | | 327 | 90 | 0.28 |
| Oct. 04, 2007 | 47.9 | 7.0 | 34.8 | | | | | | |
| Oct. 10, 2007 | 44.8 | 9.3 | | | | | 250 | 55 | 0.22 |
| Oct. 31, 2007 | 47.4 | 7.2 | 33.8 | | | | 709 | 143 | 0.20 |
| Nov. 22, 2007 | 44.4 | 8.1 | | 8.4 | 2.1 | 42.2 | 1000 | 226 | 0.23 |
| Dec. 11, 2007 | 43.8 | 7.3 | | 5.6 | 2.2 | 46.7 | 500 | 117 | 0.23 |
| Average: | 46.1 | 7.8 | 34.3 | 7 | 2.2 | 44.5 | | | 0.23 |

TABLE 17

Analysis on dry base (db) of press cake

| Press cake Dry matter g/100 g | Fat, B&D g/100 g | Protein g/100 g | TVN mg N/100 g | TMA mg N/100 g | TMAO mg N/100 g |
|---|---|---|---|---|---|
| 100 | 16.6 | | | | |
| 100 | 14.6 | 72.7 | | | |
| 100 | 20.8 | | | | |
| 100 | 15.2 | 71.3 | | | |
| 100 | 18.2 | | 18.9 | 4.7 | 95.0 |
| 100 | 16.7 | | 12.8 | 5.0 | 106.6 |
| 100 | 17.0 | 72.0 | 15.9 | 4.9 | 100.8 |

Oil was produced from the krill solids by centrifugation. Table 18. The oil was almost free for water and the content of astaxanthin was quite high (1.8 g/kg).

TABLE 18

Analysis of krill oil

| Tricanter oil (krill oil) | | Date: Oct. 31, 2007 | Date: Nov. 22, 2007 |
|---|---|---|---|
| Astaxanthin, Free | mg/kg | 22 | 29 |
| Trans | mg/kg | 12 | 14 |

TABLE 18-continued

Analysis of krill oil

| Tricanter oil (krill oil) | | Date: Oct. 31, 2007 | Date: Nov. 22, 2007 |
|---|---|---|---|
| 9-cis | mg/kg | 2.3 | 3.2 |
| 13-cis | mg/kg | 5.4 | 7.8 |
| Astaxanthin, Esters | mg/kg | 1802 | 1785 |
| Diester | mg/kg | 1142 | 1116 |
| Monoester | mg/kg | 660 | 669 |
| Astaxanthin - total | mg/kg | 1824 | 1814 |
| Water, Karl F. | g/100 g | 0.17 | 0.04 |
| FFA | g/100 g | | 0.9 |
| Vitamin A | IE/kg | | 602730 |
| Vitamin D3 | IE/kg | | <1000 |
| Vitamin E (alfa-tokoferol) | mg/kg | | 630 |

TABLE 19

Analysis of press cake from coagulum on dry base

Sample: Press cake of coagulum

| Analysis: Date: | Dry matter g/100 g | Fat, B&D g/100 g | TVN mg N/ 100 g | TMA mg N/ 100 g | TMAO mg N/ 100 g |
|---|---|---|---|---|---|
| Nov. 22, 2007 | 100 | 60.8 | 20.4 | 11.6 | 144.6 |
| Dec. 12, 2007 | 100 | 66.6 | 10.1 | 0.0 | 134.0 |
| Dec. 12, 2007* | 100 | 63.4 | 0.0 | 0.0 | 45.5 |

*After 1 wash (Press cake:water = 1:1)

The yield of coagulum press cake was about 5% of raw krill. The compositions of coagulum and retentate from micro filtration is compared in Table 20. There was hardly any difference between the products from the two process alternatives. Press cake of coagulum was dried, and Table 21 gives the analysis of the coagulum and final coagulum meal. The proximate composition based on dry matter did not change during drying, and the amino acid composition and fatty acid composition is near identical. There was some loss of phospholipids during drying. This is most probable caused by oxidation of fatty acids, but other chemical modification of the phospholipids may also be of consequence.

TABLE 20

Analysis of Retentate from micro filtration and Coagulum

| | | Retentat 25 Oct. 2007 | Coagulum 25 Oct. 2007 |
|---|---|---|---|
| Protein | g/100 g | 5.8 | 5.4 |
| Dry matter | g/100 g | 13.5 | 14.3 |
| Ash | g/100 g | 1.1 | 1.0 |
| Fat (B&D) | g/100 g | 7.3 | 8.3 |
| pH | | 8.5 | |
| TFN | mg N/100 g | 5.9 | 5.9 |
| TMA | mg N/100 g | 2.3 | 2.3 |
| TMAO | mg N/100 g | 61.0 | 48.6 |
| Lipd classes: | | | |
| Triacylglycerol | g/100 g extracted fat | 59.0 | 51 |
| Diacylglycerol | g/100 g extracted fat | 1.3 | 1 |
| Monocylglycerol | g/100 g extracted fat | <1 | <1 |
| Free fatty acids | g/100 g extracted fat | 3.8 | 3.2 |
| Cholesterol | g/100 g extracted fat | <0.5 | <0.5 |
| Cholesterol esters | g/100 g extracted fat | 1.0 | 0.8 |
| Phosphatidyl ethanolamine | g/100 g extracted fat | 1.8 | 3 |
| Phosphatidyl inositol | g/100 g extracted fat | <1 | <1 |
| Phosphatidyl serine | g/100 g extracted fat | <1 | <1 |
| Phosphatidyl choline | g/100 g extracted fat | 35.0 | 40 |
| Lyso-Phosphatidyl choline | g/100 g extracted fat | 0.8 | 1.2 |
| Total polar lipids | g/100 g extracted fat | 37.6 | 44.2 |
| Total neutral lipids | g/100 g extracted fat | 67.1 | 56.0 |
| Sum lipids | g/100 g extracted fat | 103.4 | 100.2 |
| Fatty acid composition: | | | |
| 14:0 | g/100 g extracted fat | 10.6 | 10.4 |
| 16:0 | g/100 g extracted fat | 16.4 | 16.2 |
| 18:0 | g/100 g extracted fat | 1.1 | 1.2 |
| 20:0 | g/100 g extracted fat | 0.1 | 0.1 |
| 22:0 | g/100 g extracted fat | <0.1 | <0.1 |
| 16:1 n-7 | g/100 g extracted fat | 6.3 | 6.4 |
| 18:1 (n-9) + (n-7) + (n-5) | g/100 g extracted fat | 15.5 | 15.4 |
| 20:1 (n-9) + (n-7) | g/100 g extracted fat | 1.1 | 1.1 |
| 22:1 (n-11) + (n-9) + (n-7) | g/100 g extracted fat | 0.6 | 0.5 |
| 24:1 n-9 | g/100 g extracted fat | 0.1 | 0.1 |
| 16:2 n-4 | g/100 g extracted fat | 0.5 | 0.5 |
| 16:3 n-4 | g/100 g extracted fat | 0.2 | 0.2 |
| 18:2 n-6 | g/100 g extracted fat | 1.4 | 1.4 |
| 18:3 n-6 | g/100 g extracted fat | 0.2 | 0.2 |
| 20:2 n-6 | g/100 g extracted fat | 0.1 | 0.1 |
| 20:3 n-6 | g/100 g extracted fat | 0.1 | 0.1 |
| 20:4 n-6 | g/100 g extracted fat | 0.3 | 0.3 |
| 22:4 n-6 | g/100 g extracted fat | <0.1 | <0.1 |
| 18:3 n-3 | g/100 g extracted fat | 0.7 | 0.7 |

TABLE 20-continued

Analysis of Retentate from micro filtration and Coagulum

| | | Retentat 25 Oct. 2007 | Coagulum 25 Oct. 2007 |
|---|---|---|---|
| 18:4 n-3 | g/100 g extracted fat | 1.7 | 1.7 |
| 20:3 n-3 | g/100 g extracted fat | <0.1 | <0.1 |
| 20:4 n-3 | g/100 g extracted fat | 0.3 | 0.3 |
| 20:5 n-3 (EPA) | g/100 g extracted fat | 10.5 | 10.3 |
| 21:5 n-3 | g/100 g extracted fat | 0.3 | 0.3 |
| 22:5 n-3 | g/100 g extracted fat | 0.5 | 0.4 |
| 22:6 n-3 (DHA) | g/100 g extracted fat | 5.1 | 5.0 |
| Sum saturated fat acides | g/100 g extracted fat | 28.2 | 27.9 |
| Sum monoene fat acides | g/100 g extracted fat | 23.6 | 23.4 |
| Sum PUFA (n-6) fat acides | g/100 g extracted fat | 2.1 | 2 |
| Sum PUFA (n-3) feat acides | g/100 g extracted fat | 19.1 | 18.7 |
| Sum PUFA fat acides total | g/100 g extracted fat | 21.9 | 21.4 |
| Sum fat acides total | g/100 g extracted fat | 73.7 | 72.7 |
| EPA/DHA | | 2.1 | 2.1 |

TABLE 21

Analysis of Coagulum press cake and meal dried in a Rotadisc dryer on wet and dry base

| | | Coagulum press cake Nov. 22, 2007 | Coagulum meal Nov. 22, 2007 | Coagulum press cake Nov. 22, 2007 | Coagulum meal Nov. 22, 2007 |
|---|---|---|---|---|---|
| Analysis: | | wb | wb | db | db |
| Protein | g/100 g | 14.6 | 35.3 | 37.6 | 37.4 |
| Moisture | g/100 g | 61.2 | 5.7 | 0.0 | 0.0 |
| Fat B&D | g/100 g | 23.6 | 55.1 | 60.8 | 58.4 |
| Ash | g/100 g | | 5.9 | | 6.3 |
| TMA | mg N/100 g | 4.5 | 7 | 11.6 | 7 |
| TMAO | mg N/100 g | 56.1 | 140 | 144.6 | 148 |
| Fatty acid composition: | | | | | |
| 14:0 | g/100 g extracted fat | 10.4 | 10.4 | | |
| 16:0 | g/100 g extracted fat | 17 | 17 | | |
| 18:0 | g/100 g extracted fat | 1.2 | 1.2 | | |
| 20:0 | g/100 g extracted fat | 0.1 | 0.1 | | |
| 22:0 | g/100 g extracted fat | 0.1 | 0.1 | | |
| 16:1 n-7 | g/100 g extracted fat | 6.4 | 6.4 | | |
| 18:1 (n-9) + (n-7) + (n-5) | g/100 g extracted fat | 15.2 | 15.3 | | |
| 20:1 (n-9) + (n-7) | g/100 g extracted fat | 1.1 | 1.1 | | |
| 22:1 (n-11) + (n-9) + (n-7) | g/100 g extracted fat | 0.5 | 0.6 | | |
| 24:1 n-9 | g/100 g extracted fat | 0.1 | 0.1 | | |
| 16:2 n-4 | g/100 g extracted fat | 0.5 | 0.5 | | |
| 16:3 n-4 | g/100 g extracted fat | 0.2 | 0.2 | | |
| 18:2 n-6 | g/100 g extracted fat | 1.5 | 1.4 | | |
| 18:3 n-6 | g/100 g extracted fat | 0.2 | 0.2 | | |
| 20:2 n-6 | g/100 g extracted fat | 0.1 | 0.1 | | |
| 20:3 n-6 | g/100 g extracted fat | <0.1 | <0.1 | | |
| 20:4 n-6 | g/100 g extracted fat | 0.3 | 0.3 | | |
| 22:4 n-6 | g/100 g extracted fat | <0.1 | <0.1 | | |
| 18:3 n-3 | g/100 g extracted fat | 0.7 | 0.7 | | |
| 18:4 n-3 | g/100 g extracted fat | 1.7 | 1.7 | | |
| 20:3 n-3 | g/100 g extracted fat | <0.1 | <0.1 | | |
| 20:4 n-3 | g/100 g extracted fat | 0.4 | 0.4 | | |
| 20:5 n-3 (EPA) | g/100 g extracted fat | 10.9 | 10.5 | | |
| 21:5 n-3 | g/100 g extracted fat | 0.3 | 0.3 | | |
| 22:5 n-3 | g/100 g extracted fat | 0.3 | 0.3 | | |
| 22:6 n-3 (DHA) | g/100 g extracted fat | 5.3 | 5.1 | | |
| Sum saturated fat acides | g/100 g extracted fat | 28.7 | 28.7 | | |
| Sum monoene fat acides | g/100 g extracted fat | 23.3 | 23.3 | | |
| Sum PUFA (n-6) fat acides | g/100 g extracted fat | 2 | 2 | | |
| Sum PUFA (n-3) feat acides | g/100 g extracted fat | 19.7 | 19 | | |
| Sum PUFA fat acides total | g/100 g extracted fat | 22.4 | 21.7 | | |
| Sum fat acides total | g/100 g extracted fat | 74.4 | 73.8 | | |
| Amino acids: | | | | | |
| Aspartic acid | g/100 g protein | 10.5 | 10.5 | | |
| Glutamic acid | g/100 g protein | 11.2 | 11.6 | | |
| Hydroxiproline | g/100 g protein | <0.10 | <0.10 | | |
| Serine | g/100 g protein | 4.3 | 4.2 | | |
| Glycine | g/100 g protein | 4 | 4 | | |
| Histidine | g/100 g protein | 2 | 1.9 | | |

TABLE 21-continued

Analysis of Coagulum press cake and meal dried in a Rotadisc dryer on wet and dry base

| | | Coagulum press cake Nov. 22, 2007 | Coagulum meal Nov. 22, 2007 | Coagulum press cake Nov. 22, 2007 | Coagulum meal Nov. 22, 2007 |
|---|---|---|---|---|---|
| Arginine | g/100 g protein | 4.8 | 4.7 | | |
| Threonine | g/100 g protein | 4.9 | 4.9 | | |
| Alanine | g/100 g protein | 4.8 | 4.9 | | |
| Proline | g/100 g protein | 4.2 | 4.1 | | |
| Tyrosine | g/100 g protein | 3.7 | 3.5 | | |
| Valine | g/100 g protein | 6 | 5.9 | | |
| Methionine | g/100 g protein | 2.4 | 2.4 | | |
| Isoleucine | g/100 g protein | 6.9 | 6.7 | | |
| Leucine | g/100 g protein | 9.6 | 9.4 | | |
| Phenylalanine | g/100 g protein | 4.5 | 4.4 | | |
| Lysine | g/100 g protein | 7.7 | 7.6 | | |
| Sum AA | g/100 g protein | 91.5 | 90.7 | | |
| Lipid classes: | | | | | |
| Triacylglycerol | g/100 g extracted fat | 48 | 63 | | |
| Diacylglycerol | g/100 g extracted fat | 1.2 | 1.3 | | |
| Monoacylglycerol | g/100 g extracted fat | <1 | <1 | | |
| Free fatty acids | g/100 g extracted fat | 3.2 | 3.1 | | |
| Cholesterol | g/100 g extracted fat | 1.2 | <0.5 | | |
| Cholesterol esters | g/100 g extracted fat | 0.5 | 0.9 | | |
| Phosphatidyl ethanolamine | g/100 g extracted fat | 3.1 | 1.1 | | |
| Phosphatidyl inositol | g/100 g extracted fat | <1 | <1 | | |
| Phosphatidyl serine | g/100 g extracted fat | <1 | <1 | | |
| Phosphatidyl choline | g/100 g extracted fat | 38 | 34 | | |
| Lyso-Phosphatidyl choline | g/100 g extracted fat | 1.2 | <1 | | |
| Total polar lipids | g/100 g extracted fat | 42 | 34.8 | | |
| Total neutral lipids | g/100 g extracted fat | 54.6 | 67.9 | | |
| Sum lipids | g/100 g extracted fat | 96.7 | 103.6 | | |

Krill meal. Final krill meal was produced. Press cake and press cake with stick water concentrate were dried in a hot air dryer or steam drier.

TABLE 22

Analysis of krill meal from

| Date: Nov. 22, 2007 | | Forberg Air dried Press cake meal of krill | Forberg Air dried Krill meal with stickwater | Rota disc. Steam dried Krill meal with stickwater |
|---|---|---|---|---|
| Wet base: | | | | |
| Protein | g/100 g | 66.4 | 63.6 | 66.3 |
| Moisture | g/100 g | 5.9 | 7.1 | 3.7 |
| Fat Soxhlet | g/100 g | 8.7 | 10.4 | |
| Fat B&D | g/100 g | 15.9 | 15.6 | 15.2 |
| Ash | g/100 g | 9.8 | 13.0 | 13.4 |
| Salt | g/100 g | 1.3 | 4.3 | 4.4 |
| Water sol. protein | g/100 g prot. | 11.1 | 28.0 | 27.1 |
| pH | | 8.6 | 8.3 | |
| TVN | mg N/100 g | 18.8 | 39.9 | 38.6 |
| TMA | mg N/100 g | 11.1 | 22.2 | 29.8 |
| TMAO | mg N/100 g | 109.7 | 442.1 | 399.5 |
| Dry matter base: | | | | |
| Protein | g/100 g db | 70.6 | 68.5 | |
| Fat Soxhlet | g/100 g db | 9.2 | 11.2 | |
| Fat B&D | g/100 g db | 16.9 | 16.8 | 15.8 |
| Ash | g/100 g db | 10.4 | 14.0 | |
| Salt | g/100 g db | 1.4 | 4.6 | |
| TVN | mg N/100 g db | 20.0 | 42.9 | 40.1 |
| TMA | mg N/100 g db | 11.8 | 23.9 | 30.9 |
| TMAO | mg N/100 g db | 116.6 | 475.9 | 414.9 |
| Astaxanthin on wet base: | | | | |
| Astaxanthin, Free | mg/kg | 4.6 | 3.6 | <1 |
| Trans | mg/kg | 2.5 | 1.9 | <1 |
| 9-cis | mg/kg | 0.4 | 0.4 | <1 |

TABLE 22-continued

Analysis of krill meal from

| | | Forberg Air dried Press cake meal of krill | Forberg Air dried Krill meal with stickwater | Rota disc. Steam dried Krill meal with stickwater |
|---|---|---|---|---|
| Date: Nov. 22, 2007 | | | | |
| 13-cis | mg/kg | 1.3 | 0.9 | <1 |
| Astaxanthin, Esters | mg/kg | 112.0 | 100 | 58.0 |
| Diester | mg/kg | 80.0 | 72.0 | 50.0 |
| Monoester | mg/kg | 32.0 | 27.0 | 8.1 |
| Astaxanthin - total | mg/kg | 116.6 | 103.6 | 58.0 |
| Astaxanthin on fat base: | | | | |
| Astaxanthin, Fritt | mg/kg fat | 28.9 | 23.1 | <7 |
| Trans | mg/kg fat | 15.7 | 12.2 | <7 |
| 9-cis | mg/kg fat | 2.5 | 2.6 | <7 |
| 13-cis | mg/kg fat | 8.2 | 5.8 | <7 |
| Astaxanthin, Estere | mg/kg fat | 704.4 | 641.0 | 381.6 |
| Diester | mg/kg fat | 503.1 | 461.5 | 328.9 |
| Monoester | mg/kg fat | 201.3 | 173.1 | 53.3 |
| Astaxanthin - totalt | mg/kg fat | 733.3 | 664.1 | 381.6 |
| Amino acids: | | | | |
| Aspartic acid | g/100 g protein | 10.6 | 9.2 | 9.2 |
| Glutamic acid | g/100 g protein | 14.1 | 12.4 | 12.3 |
| Hydroxiproline | g/100 g protein | <0.5 | <0.5 | 0.1 |
| Serine | g/100 g protein | 4.2 | 3.7 | 3.8 |
| Glycine | g/100 g protein | 4.4 | 4.4 | 4.5 |
| Histidine | g/100 g protein | 2.3 | 1.9 | 1.9 |
| Arginine | g/100 g protein | 6.6 | 6.0 | 6.1 |
| Threonine | g/100 g protein | 4.3 | 3.7 | 4.1 |
| Alanine | g/100 g protein | 5.4 | 4.9 | 5.3 |
| Proline | g/100 g protein | 3.7 | 4.1 | 4 |
| Tyrosine | g/100 g protein | 4.4 | 3.1 | 4.7 |
| Valine | g/100 g protein | 5.1 | 4.4 | 4.5 |
| Methionine | g/100 g protein | 3.2 | 2.7 | 2.7 |
| Isoleucine | g/100 g protein | 5.3 | 4.5 | 4.5 |
| Leucine | g/100 g protein | 8.0 | 6.9 | 6.9 |
| Phenylalanine | g/100 g protein | 4.6 | 3.9 | 4 |
| Lysine | g/100 g protein | 8.2 | 7.0 | 6.6 |
| Sum AA | g/100 g protein | 94.4 | 82.8 | 85.2 |
| Lipide classes: | | | | |
| Triacylglycerol | g/100 g extracted fat | | 41.0 | 63 |
| Diacylglycerol | g/100 g extracted fat | | 1.7 | 1.3 |
| Monocylglycerol | g/100 g extracted fat | | <1 | <1 |
| Free fatty acids | g/100 g extracted fat | | 8.8 | 3.1 |
| Cholesterol | g/100 g extracted fat | | 2.4 | <0.5 |
| Cholesterol esters | g/100 g extracted fat | | <0.5 | 0.9 |
| Phosphatidyl ethanolamine | g/100 g extracted fat | | 3.6 | 1.1 |
| Phosphatidyl inositol | g/100 g extracted fat | | <1 | <1 |
| Phosphatidyl serine | g/100 g extracted fat | | <1 | <1 |
| Phosphatidyl choline | g/100 g extracted fat | | 43.0 | 34 |
| Lyso-Phosphatidyl choline | g/100 g extracted fat | | 1.1 | <1 |
| Total polar lipids | g/100 g extracted fat | | 47.2 | 34.8 |
| Total neutral lipids | g/100 g extracted fat | | 54.2 | 67.9 |
| Sum lipids | g/100 g extracted fat | | 101.4 | 103.6 |

Example 5

Figure 4:
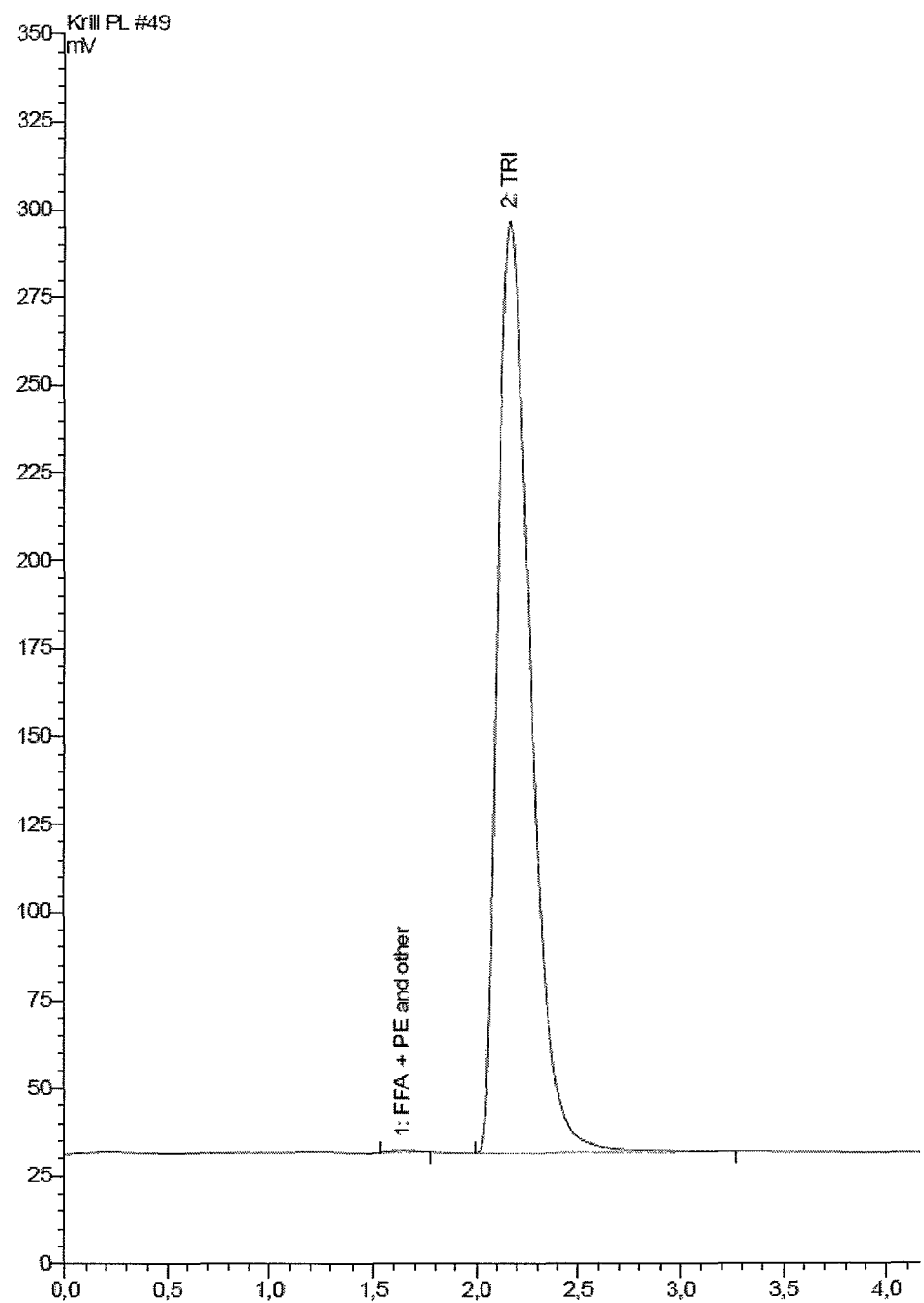
FIG. 4 is a GC of the neutral fraction extracted from krill coagulate.
Figure 5:
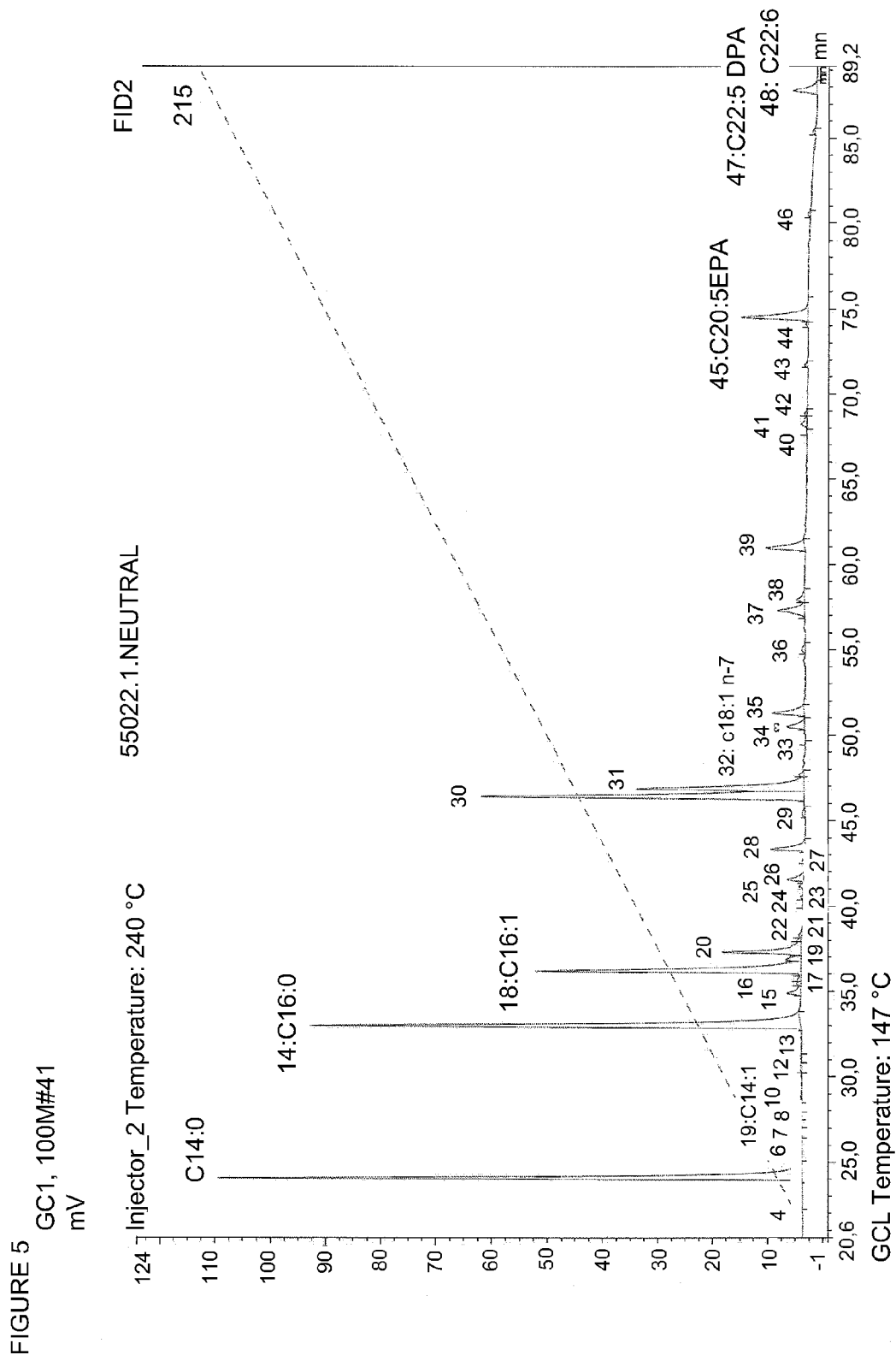
FIG. 5 is a GC analysis of the neutral fraction extracted from krill coagulate.

Coagulum meal produced as described in Example 4 was extracted using lab scale SFE. 4.885 g of coagulum (freeze dried over night) via a two step extraction: 1) SFE: $CO_2$, 500 Bar, 60° C., 70 min at a medium flow rate of 1.8 ml/min of $CO_2$; 2) SFE: $CO_2$+15% EtOH, 500 Bar, 60° C., 70 min at a medium flow rate of 2.5 ml/min of $CO_2$+EtOH. The first step extracted 1.576 g of extracted neutral fraction (NF). As shown in FIGS. 4 and 5, the analysis at HPLC show lower than the detectable limit content on PL in the NF. It was extracted about 32.25% of the total material. Table 29 provides the peak areas of the components of the neutral fraction as determined by GC.

TABLE 29

| Rel. Area % | Peakname | Ret. Time min | Area mV * min | Height mV | Rel. Area % |
|---|---|---|---|---|---|
| 0.29 | n.a. | 17.455 | 0.2864 | 2.271 | 0.29 |
| 19.49 | C14:0 | 24.073 | 19.0301 | 105.696 | 19.49 |
| 21.16 | C16:0 | 32.992 | 20.6601 | 88.859 | 21.16 |
| 11.99 | C16:1 | 36.197 | 11.7032 | 48.125 | 11.99 |
| 3.5 | n.a. | 37.28 | 3.4166 | 14.344 | 3.5 |
| 1.57 | n.a. | 43.331 | 1.5375 | 6.141 | 1.57 |
| 15.6 | n.a. | 46.425 | 15.2285 | 58.605 | 15.6 |
| 8.81 | n.a. | 46.873 | 8.5983 | 30.65 | 8.81 |
| 0.93 | n.a. | 50.499 | 0.9055 | 3.164 | 0.93 |
| 1.56 | n.a. | 51.292 | 1.5216 | 5.746 | 1.56 |
| 1.67 | n.a. | 57.312 | 1.6281 | 4.78 | 1.67 |
| 2.03 | n.a. | 60.985 | 1.98 | 6.963 | 2.03 |
| 0.02 | n.a. | 67.761 | 0.0189 | 0.116 | 0.02 |

TABLE 29-continued

| Rel. Area % | Peakname | Ret. Time min | Area mV * min | Height mV | Rel. Area % |
|---|---|---|---|---|---|
| 0.11 | n.a. | 68.833 | 0.1066 | 0.423 | 0.11 |
| 0.11 | n.a. | 71.705 | 0.1028 | 0.497 | 0.11 |
| 0.08 | n.a. | 74.053 | 0.0806 | 0.398 | 0.08 |
| 3.92 | C20:5 EPA | 74.489 | 3.826 | 12.07 | 3.92 |
| 0.11 | n.a. | 80.519 | 0.1095 | 0.48 | 0.11 |
| 0.08 | C22:5 DPA | 85.369 | 0.0785 | 0.41 | 0.08 |
| 1.3 | C22:6 DHA | 87.787 | 1.2719 | 4.253 | 1.3 |

Figure 6:
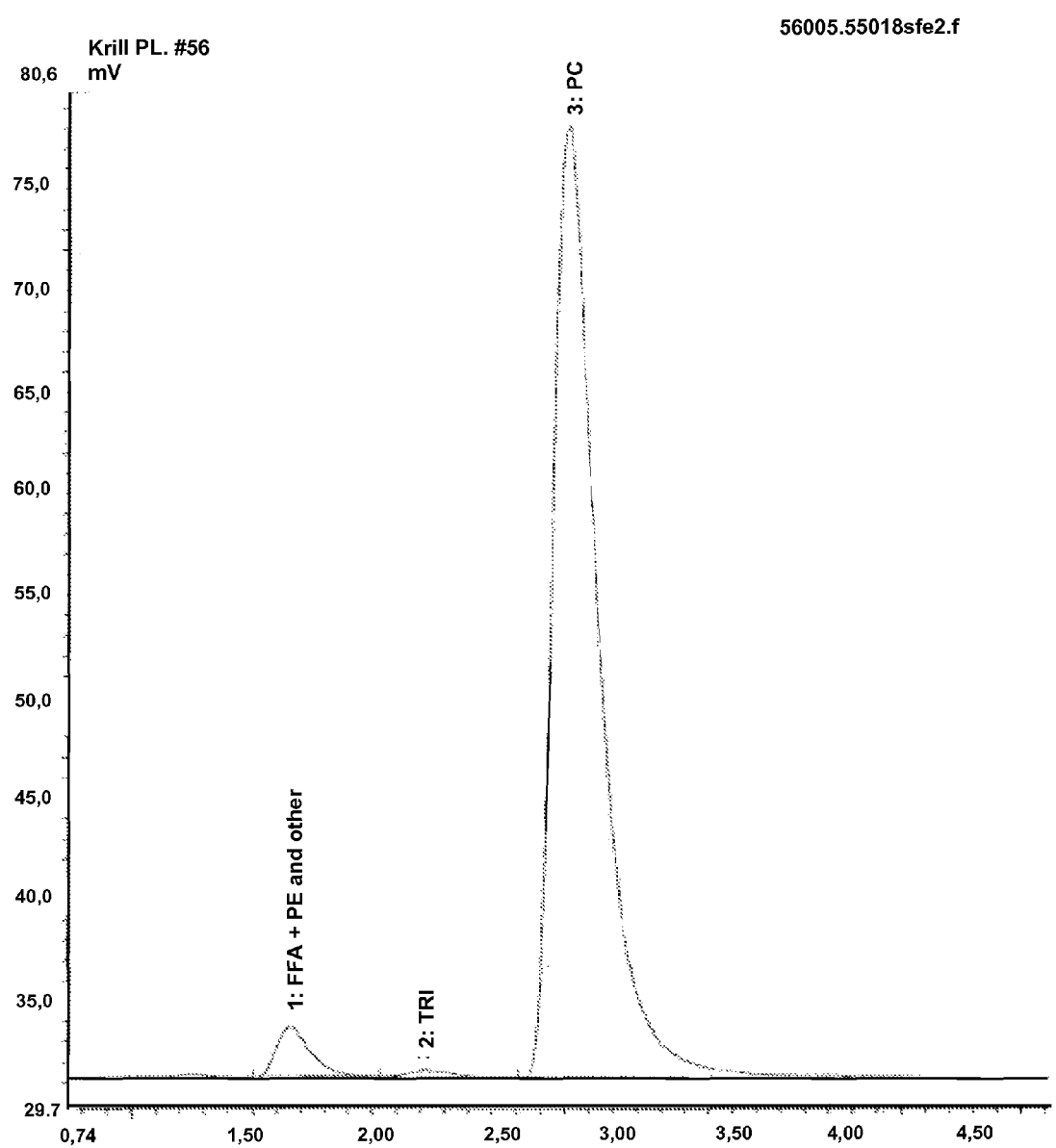
FIG. 6 is a GC of the polar fraction extracted from krill coagulate.

The second step extracted a polar fraction of 1.023 g corresponding to 20.95% of the total material. The polar fraction consisted mostly of PL and just less than 1% TG. See FIGS. 6 and 7. Table 30 provides the peak areas of the components of the polar fraction as determined by GC.

TABLE 30

| Rel. Area % | Peakname | Ret. Time min | Area mV * min | Height mV | Rel. Area % |
|---|---|---|---|---|---|
| 2.87 | C14:0 | 24.025 | 4.8099 | 28.243 | 2.87 |
| 28.5 | C16:0 | 33.084 | 47.7079 | 182.756 | 28.5 |
| 1.82 | C16:1 | 36.155 | 3.0402 | 13.166 | 1.82 |
| 1.13 | n.a. | 43.304 | 1.8848 | 8.208 | 1.13 |
| 3.89 | n.a. | 46.336 | 6.5129 | 27.429 | 3.89 |
| 5.46 | n.a. | 46.852 | 9.1467 | 35.825 | 5.46 |
| 2.15 | n.a. | 51.265 | 3.6015 | 14.095 | 2.15 |
| 1.6 | n.a. | 57.121 | 2.6735 | 7.213 | 1.6 |
| 1.72 | n.a. | 60.944 | 2.8832 | 10.686 | 1.72 |
| 2.03 | n.a. | 68.259 | 3.3913 | 8.025 | 2.03 |
| 30.09 | C20:5 EPA | 74.599 | 50.3768 | 163.312 | 30.09 |
| 12.11 | C22:6 DHA | 87.832 | 20.2774 | 68.714 | 12.11 |

The coagulate was dried over night with a weight loss of about 5.53% w/w. The total extracted was about 53.2% of the starting weight of the dried material.

Example 6

Freshly harvested krill were processed into coagulum on board the ship either 10 minutes or six hours post harvest. The coagulum produced from both the 10 minute post harvest krill and the 6 hour post harvest krill contained less than 1 mg/100 g volatile nitrogen, less than 1 mg/100 g trimethylamine (TMA), and less than 1 g/100 g lysophosphatidylcholine. This can be compared to the coagulum produced from frozen krill in Example 4 above, which contained higher levels of volatile nitrogen, and lysophosphatidylcholine. The methods of the invention which utilize freshly harvested krill provide krill products that are characterized in being essentially free of TMA, volatile nitrogen, and lysophosphatidylcholine.

Example 7

Coagulum meal, 250 g, and krill oil were mixed in a kitchen mixer. The aim was to add 300-500 mg astaxanthin/kg coagulum meal. If the oil contains 1500 mg astaxanthin/kg krill oil, at least 200 g oil should be added to one kg of coagulum meal. The flow of the meal was markedly reduced by addition of 10% oil, and the oil came off on the packaging when the addition of oil was increased to 14 and 20%. 3.5 kg coagulum from was thawed and milled on a Retsch ZM1 with a 2 mm sieve. The quantity of milled powder was 2.96 kg. The 2.96 kg dried coagulum was added 300 g krill oil in three portions. The knives in the mixer (Stephan UM12) were to far from the bottom to give a good mixing, so the mixture was mixed by hand and mixer intermittently. The astaxanthin content in the final mixture was 40% lower than calculated. New analyses of astaxanthin were performed on the oil and on the fortified meal. The krill oil had been stored in a cold room at 3° C. for 4 months, and the astaxanthin content in the oil did not change during this storage. A new sample were drawn from the fortified meal after 4 weeks frozen storage, and the astaxanthin content was the same in both samples (Table 31).

TABLE 31

Composition of steam dried coagulum fortified with 10% krill oil.

| | | Analysed Meal with oil | Calculated Meal with oil | New analysis Krill oil | New analysis Meal with oil |
|---|---|---|---|---|---|
| Dry matter | g/100 g | 98.0 | 99.2 | | |
| Protein | g/100 g | | 33.6 | | |
| Fat (B&D) | g/100 g | 58.9 | 60.7 | | |
| Ash | g/100 g | | 5.9 | | |
| Water soluble protein | g/100 g protein | | 15.8 | | |
| TFN | mg N/100 g | | 10 | | |
| TMA | mg N/100 g | | 10 | | |
| TMAO | mg N/100 g | | 113 | | |
| Astaxanthin, Free | mg/kg | 2.5 | 4.9 | 27 | 2.8 |
| Trans | mg/kg | 1.4 | 2.5 | 14 | 1.5 |
| 9-cis | mg/kg | 0.35 | 0.6 | 3.1 | 0.4 |
| 13-cis | mg/kg | 0.57 | 1.2 | 6.2 | 0.7 |
| Astaxanthin, Esters | mg/kg | 193 | 338 | 1805 | 197 |
| Diester | mg/kg | 126 | 216 | 1128 | 127 |
| Monoester | mg/kg | 67 | 122 | 677 | 70 |
| Astaxanthin - total | mg/kg | 196 | 343 | 1832 | 200 |
| Astaxanthin, Free | mg/kg lipid | 4.2 | 8.1 | | |
| Trans | mg/kg lipid | 2.4 | 4.2 | | |
| 9-cis | mg/kg lipid | 0.6 | 1.0 | | |
| 13-cis | mg/kg lipid | 1.0 | 2.0 | | |
| Astaxanthin, Esters | mg/kg lipid | 328 | 556 | | |
| Diester | mg/kg lipid | 214 | 356 | | |

TABLE 31-continued

Composition of steam dried coagulum fortified with 10% krill oil.

|  |  | Analysed Meal with oil | Calculated Meal with oil | New analysis Krill oil | New analysis Meal with oil |
|---|---|---|---|---|---|
| Monoester | mg/kg lipid | 114 | 200 |  |  |
| Astaxanthin - total | mg/kg lipid | 332 | 564 |  |  |
| Ffa | g/100 g extracted fat |  | 4.4 |  |  |
| Total polar lipids | g/100 g extracted fat |  | 39.7 |  |  |
| Total neutral lipids | g/100 g extracted fat |  | 60.1 |  |  |

The astaxanthin content in fortified coagulum meal is 58% of the amount in the ingredients. This reduction in astaxanthin takes place during mixing of dried coagulum and krill oil, and indicate that dried coagulum is easily oxidized.

Example 8

The dried coagulum meal was extracted by supercritical fluid extraction. The extracted oil was analyzed as presented in Tables 32-34.

TABLE 32

Lipid composition

| Phosphatidylcholine | 34 g/100 g lipid |
| Phosphatidylethanolamine | 1.3 g/100 g lipid |
| Triglycerides | 48 g/100 g lipid |
| Cholesterol | n.d. |
| Free fatty acids | 1.0 g/100 g lipid |

TABLE 33

Fatty acid profile

| Total saturated fatty acids | 26.3 g/100 g lipid |
| Total omega-3 fatty acids | 18.1 g/100 g lipid |
| Total fatty acids | 67.3 g/100 g lipid |

TABLE 34

Miscellaneous properties

| Astaxanthin | 130 mg/kg |
| TMAO | 87 mg N/100 g |
| TMA | <1 mg N/100 g |
| Viscosity at 25° C. | 61 mPa s |

Example 9

Coagulum meal prepared as described above was administered to two human subjects and absorption of the product was determined by measuring omega-3 fatty acids in total lipids and in phospholipids in plasma. Subject 1 consumed 8 g of coagulum in combination with yoghurt, whereas subject 2 consumed 8 g of krill oil without yoghurt. The data is presented in Tables 35 (Subject 1) and 36 (Subject 2).

TABLE 35

| Time (h) | C20:5 W3 (EPA) | C22:5 W3 (DPA) | C22:6 W3 (DHA) |
|---|---|---|---|
| 0 | 0.117 | 0.062 | 0.267 |
| 0.5 | 0.118 | 0.063 | 0.270 |
| 1 | 0.113 | 0.061 | 0.260 |
| 1.5 | 0.117 | 0.064 | 0.272 |
| 2 | 0.116 | 0.063 | 0.271 |
| 2.5 | 0.119 | 0.063 | 0.271 |
| 3 | 0.123 | 0.065 | 0.281 |
| 3.5 | 0.122 | 0.063 | 0.275 |
| 4 | 0.123 | 0.063 | 0.275 |
| 5 | 0.141 | 0.065 | 0.294 |
| 6 | 0.153 | 0.064 | 0.286 |
| 7 | 0.154 | 0.062 | 0.277 |
| 8 | 0.165 | 0.063 | 0.292 |
| 10 | 0.167 | 0.063 | 0.291 |
| 12 | 0.163 | 0.061 | 0.275 |
| 16 | 0.169 | 0.062 | 0.301 |
| 24 | 0.173 | 0.074 | 0.323 |

TABLE 36

| Time (h) | C20:5 W3 (EPA) | C22:5 W3 (DPA) | C22:6 W3 (DHA) |
|---|---|---|---|
| 0 | 0.146 | 0.052 | 0.260 |
| 0.5 | 0.142 | 0.052 | 0.260 |
| 1 | 0.146 | 0.054 | 0.268 |
| 1.5 | 0.142 | 0.053 | 0.263 |
| 2 | 0.145 | 0.054 | 0.267 |
| 2.5 | 0.140 | 0.053 | 0.258 |
| 3 | 0.143 | 0.054 | 0.264 |
| 3.5 | 0.155 | 0.056 | 0.278 |
| 4 | 0.155 | 0.055 | 0.277 |
| 5 | 0.179 | 0.057 | 0.295 |
| 6 | 0.217 | 0.057 | 0.316 |
| 7 | 0.204 | 0.057 | 0.304 |
| 8 | 0.211 | 0.060 | 0.320 |
| 10 | 0.187 | 0.057 | 0.293 |
| 12 | 0.171 | 0.054 | 0.272 |
| 16 | 0.166 | 0.052 | 0.272 |
| 24 | 0.169 | 0.061 | 0.290 |

These data show that absorption patterns of the coagulum and krill oil are different for the two subjects. The EPA pattern in subject 1 (coagulum) shows that a high EPA level is maintained over a long time despite the fact that coagulum contains less lipid than the krill oil. The coagulum has also enriched the circulating PL pool which could be an indication of absorption/incorporation of krill oil fatty acids in PL form. We have previously observed that krill oil is more efficient in enriching tissue lipid fatty acid profiles than fish oil. These data indicate that coagulum is even more bioeffective than krill oil.

Example 10

The phospholipid content of the retentate was further analyzed by NMR. Table 37 provides the results.

TABLE 37

| Phospholipid | % (w/w) |
|---|---|
| Phosphatidylcholine | 16.5 |
| Alkylacylphosphatidylcholine | 1.7 |
| Lyso-alkylacylphosphatidylcholine | 0.28 |
| 2-lysophosphatidylcholine | 0.52 |
| Phosphatidylethanolamine | 0.59 |
| N-acylphosphatidylethanolamine | 3.6 |
| Total phospholipid | 23.23 |

Example 11

This example provides an analysis of the volatile compounds in oil extracted from krill meal and oil extracted from coagulum meal. Table 38. Briefly, oil was extracted by SFE from regular krill meal or meal prepared from coagulum as described above. The oil prepared from coagulum meal had substantially reduced amounts of volatile compounds as compared to the oil prepared from regular krill meal. In particular, 1-penten-3-one was detected in oil prepared from regular krill meal and was absent in oil prepared from coagulum meal. 1-pentene-3-one have previously been identified has a key marker of fishy and metallic off-flavor in fish oil and fish oil enriched food products (Jacobsen et al., J. Agric Food Chem, 2004, 52, 1635-1641).

TABLE 38

| Compound | TIC peak area (Krill oil extracted from krill meal using SFE) | Description | TIC peak area (Krill oil extracted from coagulum using SFE) | Description |
|---|---|---|---|---|
| dimethyl amine | 180403283 | | 22848535 | |
| trimethyl amine | 255213688 | old fish, strong bad | 49040416 | old fish |
| ethanol | 394615326 | fresh | 1426886614 | vodka, ethanol |
| acetone | 875959 | | 0 | |
| acetic acid | 36136270 | weak smell | 0 | |
| methyl vinyl ketone | 515892 | | 0 | |
| 2-butanone | 2807131 | sweet | 23124362 | |
| ethyl acetate | 6231705 | | 404501 | |
| 1-[dimethylamino]-2-propanone | 23316404 | | 15380603 | |
| 1-penten-3-one | 5627101 | rubbery | 0 | weak dishcloth |
| n-heptane | 291386 | | 0 | |
| 2-ethyl furan | 1640866 | weak sweet | 0 | |
| ethyl propionate | 909959 | | 0 | |
| 2-methyl-2-pentenal | 6996219 | | 0 | |
| pyridine | 2085743 | | 0 | |
| acetamide | 6169014 | pleasant | 0 | |
| toluene | 4359806 | | 0 | |
| N,N-dimethyl formamide | 177968590 | garden hose, mint | 0 | garden hose |
| ethyl butyrate | 1122805 | | 0 | |
| 2-ethyl-5-methyl furan | 1550476 | good, flower | 427805 | |
| butyl acetate | 306001 | | 856292 | |
| 3-methyl-1,4-heptadiene | 1617339 | | 0 | weak smell, rubber |
| isovaleric acid | 1528541 | foot sweat, weak | 0 | |
| methyl pyrazine | 1335979 | peculiar | 0 | |
| ethyl isovalerate | 1043918 | fruity | 0 | fruity |
| N,N-dimethyl acetamide | 9895351 | | 0 | smell, solvent |
| 2-heptanone | 7397187 | blue cheese | 0 | |
| 2-ethyl pyridine | 317424 | | 0 | |
| butyrolactone | 652076 | butter, pleasant | 0 | |
| 2,5-dimethyl pyrazine | 2414087 | | 0 | |
| ethyl pyrazine | 1909284 | metallic | 0 | soft |
| N,N-dimethyl propanamide | 1160830 | unpleasant | 0 | |
| benzaldehyde | 3134653 | | 0 | |
| 2-octanone | 2068169 | disgusting | 0 | |
| β-myrcene | 2618870 | | 0 | |
| dimethyl trisulfide | 3279406 | sewer | 0 | |
| n-decane | 1851488 | | 331629 | |

TABLE 38-continued

| Compound | TIC peak area (Krill oil extracted from krill meal using SFE) | Description | TIC peak area (Krill oil extracted from coagulum using SFE) | Description |
|---|---|---|---|---|
| trimethyl pyrazine | 4186679 | unpleasant | 0 | |
| 1-methyl-2-pyrrolidone | 9577873 | | 0 | |
| eucalyptol | 0 | | 868411 | peppermint |
| asetofenoni | 1146348 | smell, pleasant | 350688 | |

Example 12

Krill meal produced by the traditional process (Tables 39-42) was compared with krill meal produced from the solid fraction remaining after removal of krill milk (Tables 43-46).

TABLE 39

| | | |
|---|---|---|
| 14:0 | g/100 g total fat | 8.3 |
| 16:0 | g/100 g total fat | 15.4 |
| 18:0 | g/100 g total fat | 1.0 |
| 20:0 | g/100 g total fat | <0.1 |
| 22:0 | g/100 g total fat | <0.1 |
| 16:1 n-7 | g/100 g total fat | 4.7 |
| 18:1 (n-9) + (n-7) + (n-5) | g/100 g total fat | 13.5 |
| 20:1 (n-9) + (n-7) | g/100 g total fat | 0.9 |
| 22:1 (n-11) + (n-9) + (n-7) | g/100 g total fat | 0.6 |
| 24:1 n-9 | g/100 g total fat | 0.1 |
| 16:2 n-4 | g/100 g total fat | 0.6 |
| 16:3 n-4 | g/100 g total fat | 0.3 |
| 18:2 n-6 | g/100 g total fat | 1.1 |
| 18:3 n-6 | g/100 g total fat | 0.1 |
| 20:2 n-6 | g/100 g total fat | <0.1 |
| 20:3 n-6 | g/100 g total fat | <0.1 |
| 20:4 n-6 | g/100 g total fat | 0.3 |
| 22:4 n-6 | g/100 g total fat | <0.1 |
| 18:3 n-3 | g/100 g total fat | 0.8 |
| 18:4 n-3 | g/100 g total fat | 1.8 |
| 20:3 n-3 | g/100 g total fat | <0.1 |
| 20:4 n-3 | g/100 g total fat | 0.4 |
| 20:5 n-3 | g/100 g total fat | 11.3 |
| 21:5 n-3 | g/100 g total fat | 0.4 |
| 22:5 n-3 | g/100 g total fat | 0.3 |
| 22:6 n-3 | g/100 g total fat | 6.5 |

TABLE 40

| | | |
|---|---|---|
| * Fat Bligh & Dyer | % | 22.8 |
| Sum saturated fatty acids | g/100 g total fat | 24.7 |
| Sum monounsaturated fatty acids | g/100 g total fat | 19.8 |
| Sum PUFA (n-6) | g/100 g total fat | 1.6 |
| Sum PUFA (n-3) | g/100 g total fat | 21.5 |
| Sum PUFA | g/100 g total fat | 24.0 |
| Sum fatty acids total | g/100 g total fat | 68.5 |

TABLE 41

| | | |
|---|---|---|
| Triacylglycerol | g/100 g total fat | 46 |
| Diacylgyycerol | g/100 g total fat | 1.0 |
| Monoacylglycerol | g/100 g total fat | <1 |
| Free fatty acids | g/100 g total fat | 4.4 |
| Cholesterol | g/100 g total fat | 1.6 |
| Cholesterol ester | g/100 g total fat | 0.8 |
| Phosphatidylethanolamine | g/100 g total fat | 4.6 |
| Phosphatidylinositol | g/100 g total fat | <1 |
| Phosphatidylserine | g/100 g total fat | <1 |
| Phosphatidylcholine | g/100 g total fat | 37 |
| Lyso-Phosphatidylcholine | g/100 g total fat | 2.0 |
| Total polar lipids | g/100 g total fat | 36.2 |

TABLE 41-continued

| | | |
|---|---|---|
| Totale neutral lipids | g/100 g total fat | 54.0 |
| Total sum lipids | g/100 g total fat | 96.2 |

TABLE 42

| | | |
|---|---|---|
| Protein Kjeldahl (N * 6.25) | % | 60.9 |
| Total | % | 92.7 |
| Salt (NaCI) | % | 2.9 |
| Trimetylamine-N | Mg N/100 gram | 4 |
| Trimethylaminoxide-N | Mg N/100 gram | 149 |
| Free Astaxanthin | Mg/kg | <1 |
| Astaxanthin ester | Mg/kg | 122 |

TABLE 43

| | | |
|---|---|---|
| 14:0 | g/100 g total fat | 5.0 |
| 16:0 | g/100 g total fat | 13.9 |
| 18:0 | g/100 g total fat | 0.8 |
| 20:0 | g/100 g total fat | <0.1 |
| 22:0 | g/100 g total fat | <0.1 |
| 16:1 n-7 | g/100 g total fat | 3.0 |
| 18:1 (n-9) + (n-7) + (n-5) | g/100 g total fat | 11.4 |
| 20:1 (n-9) + (n-7) | g/100 g total fat | 0.5 |
| 22:1 (n-11) + (n-9) + (n-7) | g/100 g total fat | 0.4 |
| 24:1 n-9 | g/100 g total fat | 0.1 |
| 16:2 n-4 | g/100 g total fat | 0.4 |
| 16:3 n-4 | g/100 g total fat | 0.2 |
| 18:2 n-6 | g/100 g total fat | 1.2 |
| 18:3 n-6 | g/100 g total fat | 0.1 |
| 20:2 n-6 | g/100 g total fat | 0.1 |
| 20:3 n-6 | g/100 g total fat | 0.1 |
| 20:4 n-6 | g/100 g total fat | 0.4 |
| 22:4 n-6 | g/100 g total fat | <0.1 |
| 18:3 n-3 | g/100 g total fat | 0.7 |
| 18:4 n-3 | g/100 g total fat | 1.2 |
| 20:3 n-3 | g/100 g total fat | 0.1 |
| 20:4 n-3 | g/100 g total fat | 0.3 |
| 20:5 n-3 | g/100 g total fat | 13.1 |
| 21:5 n-3 | g/100 g total fat | 0.3 |
| 22:5 n-3 | g/100 g total fat | 0.3 |
| 22:6 n-3 | g/100 g total fat | 10.0 |

TABLE 44

| | | |
|---|---|---|
| * Fat Bligh & Dyer | % | 10.2 |
| Sum saturated fatty acids | g/100 g total fat | 19.7 |
| Sum monounsaturated fatty acids | g/100 g total fat | 15.3 |
| Sum PUFA (n-6) | g/100 g total fat | 1.8 |
| Sum PUFA (n-3) | g/100 g total fat | 26.1 |
| Sum PUFA | g/100 g total fat | 28.5 |
| Sum fatty acids | g/100 g total fat | 63.5 |

TABLE 45

| | | |
|---|---|---|
| Triacylglycerol | g/100 g total fat | 25 |
| Diacylgyycerol | g/100 g total fat | 0.7 |
| Monoacylglycerol | g/100 g total fat | <1 |
| Free fatty acids | g/100 g total fat | 0.9 |
| Cholesterol | g/100 g total fat | 3.1 |
| Cholesterol ester | g/100 g total fat | <0.5 |
| Phosphatidylethanolamine | g/100 g total fat | 12.8 |
| Phosphatidylinositol | g/100 g total fat | <1 |
| Phosphatidylserine | g/100 g total fat | <1 |
| Phosphatidylcholine | g/100 g total fat | 49 |
| Lyso-Phosphatidylcholine | g/100 g total fat | 1.3 |
| Total polar lipid | g/100 g total fat | 63.2 |
| Total neutral lipid | g/100 g total fat | 29.7 |
| Total sum lipid | g/100 g total fat | 92.9 |

TABLE 46

| | | |
|---|---|---|
| Protein Kjeldahl (N * 6.25) | % | 73.9 |
| Total | % | 90.2 |
| Salt (NaCl) | % | 1.9 |
| Trimetylamine-N | Mg N/100 gram | 7 |
| Trimethylaminoxide-N | Mg N/100 gram | 224 |
| Free Astaxanthin | Mg/kg | 2.8 |
| Astaxanthin ester | Mg/kg | 89 |

Neusilin ULF2 as an adsorption agent. Different compositions were compacted; all showed tablet strength below 50 N and laminated/capped.

Wet granulation. By wet granulation, the binding properties of the powder can be improved. The adsorption agent was added to the powder blend prior to granulation.

Procedure. Granulation liquid was made by dissolving the binder in the solvent. Krill powder was blended with Neusilin UFL2 and wetted with the granulation liquid. The wet mass was forced through a 25 mesh screen. The granules were dried at 40° C. for 12 hours and passed through a 18 mesh screen.

Tabletting. The dry granules were mixed with the other excipients (Table 47), and tablets were compacted using a single punch tablet press. Tablet hardness was measured on a fracture resistant tester.

TABLE 47

| Excipients | |
|---|---|
| Ingredient | Amount (% of total) |
| Neusilin UFL2 | 10 |
| Avicel PH102 | 10 |
| Ac-Di-Sol | 5 |

TABLE 48

List of ingredients

| Name of ingredients | Containing | Function | Quality |
|---|---|---|---|
| Krill Calgary (Aker BioMarine) | | Active ingredient | |
| Neusilin UFL2 (Fuji chemical) | Magnesium aluminometasilicate | Adsorption agent | Ph. Jap. curr. ed. |
| Klucel EF (Hercules) | Hydroxypropyl cellulose | Binding agent | Ph. Eur. curr. ed. |
| Kollidon 30 (BASF) | Polyvinyl pyrrolidone | Binding agent | Ph. Eur. curr. ed. |
| Ac-Di-Sol (FMC) | Croscaramellose sodium | Disintegrant | Ph. Eur. curr. ed. |
| Avicel PH102 (FMC) | Microcrystalline cellulose | Binding agent | Ph. Eur. curr. ed. |
| Ethanol (96%) | | Solvent | Ph. Eur. curr. ed. |
| Purified water | | Solvent | Ph. Eur. curr. ed. |
| Magnesium stearate | Magnesium stearate | Antiadherant | Ph. Eur. curr. ed. |

Example 13

The krill powder made from coagulum described above is characterised as a powder containing large amounts of fat or fatty acids (40%). As a consequence of this, the powder has poor flow properties with typical values of Carr index of 20%. A challenge is to reach a high pay load of the tablets, reaching tables that have acceptable technical properties.

Typical problems related to tabletting of the krill powder are: 1) Large mass variation of tablets due to poor flow properties; and 2) Low tablet strength due to high amount of fats. The following example shows that flow properties can be improved by adding a glidant or by granulation. Compaction of pure krill powder results in poor tablets, which do not hold together. This example shows that improvement of compacting properties by adding an adsorptive agent.

Direct compression. Initially direct compression was performed. A glidant such as colloidal silica was added as well as Process description. A typical batch size of 1 kg was made by wet granulation, following drying, sieving, mixing and tabletting. The following compositions were made and tested.

Composition 1

| Name of ingredient | Amount (%) |
|---|---|
| Krill Calgary (1 mm) | 61 |
| Neusilin UFL2 | 22 |
| Kollidon 30 | 3 |
| Avicel PH102 | 10 |
| Ac-Di-Sol | 5 |

Composition 2

| Name of ingredient | Amount (%) |
|---|---|
| Krill Calgary (1 mm) | 63 |
| Neusilin UFL2 | 22 |
| Kollidon 30 | 1 |
| Avicel PH102 | 10 |
| Ac-Di-Sol | 5 |

Composition 3

| Name of ingredient | Amount (%) |
|---|---|
| Krill Calgary (1 mm) | 66 |
| Neusilin UFL2 | 16 |
| Kollidon 30 | 3 |
| Avicel PH102 | 10 |
| Ac-Di-Sol | 5 |

Composition 4

| Name of ingredient | Amount (%) |
|---|---|
| Krill Calgary (1 mm) | 68 |
| Neusilin UFL2 | 16 |
| Kollidon 30 | 1 |
| Avicel PH102 | 10 |
| Ac-Di-Sol | 5 |

Composition 5

| Name of ingredient | Amount (%) |
|---|---|
| Krill Calgary (1 mm) | 59 |
| Neusilin UFL2 | 22 |
| Klucel EF | 4 |
| Avicel PH102 | 10 |
| Ac-Di-Sol | 5 |

Composition 6

| Name of ingredient | Amount (%) |
|---|---|
| Krill Calgary (1 mm) | 61 |
| Neusilin UFL2 | 22 |
| Klucel EF | 2 |
| Avicel PH102 | 10 |
| Ac-Di-Sol | 5 |

Composition 7

| Name of ingredient | Amount (%) |
|---|---|
| Krill Calgary (1 mm) | 65 |
| Neusilin UFL2 | 16 |
| Klucel EF | 4 |
| Avicel PH102 | 10 |
| Ac-Di-Sol | 5 |

Composition 8

| Name of ingredient | Amount (%) |
|---|---|
| Krill Calgary (1 mm) | 67 |
| Neusilin UFL2 | 16 |
| Klucel EF | 2 |
| Avicel PH102 | 10 |
| Ac-Di-Sol | 5 |

Tablet hardness. The hardness of the tablets was almost independent of the compaction pressure. Maximum hardness is given in Table 49. The tablet hardness should be at least 60 N, which is achieved by adding 22% of Neusilin UFL2. Both binders gave acceptable tablet strength, whereby Klucel EF gave somewhat harder tablets.

A standard USP test was used for hardness. The test is intended to determine, under defined conditions, the resistance to crushing of tablets, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the tablet. The apparatus is calibrated using a system with a precision of 1 newton. The tablet is placed between the jaws, taking into account, where applicable, the shape, the break-mark and the inscription; for each measurement the tablet is oriented in the same way with respect to the direction of application of the force. The measurement is carried out on 10 tablets, taking care that all fragments of tablets have been removed before each determination.

TABLE 49

| Composition | Hardness (N) |
|---|---|
| 1 | 60 |
| 2 | 78 |
| 3 | 52 |
| 4 | 35 |
| 5 | 98 |
| 6 | 89 |
| 7 | 56 |
| 8 | 47 |

Disintegration. Disintegration was measured on composition 5 and 6 using a standard USP disintegration tester. Disintegration time was in the range of 10 min. The standard protocol is as follows. This test is provided to determine whether tablets or capsules disintegrate within the prescribed time when placed in a liquid medium under the experimental conditions presented below.

For the purposes of this test, disintegration does not imply complete dissolution of the unit or even of its active constituent. Complete disintegration is defined as that state in which any residue of the unit, except fragments of insoluble coating or capsule shell, remaining on the screen of the test apparatus or adhering to the lower surface of the discs, if used, is a soft mass having no palpably firm core.

Apparatus. The apparatus consists of a basket-rack assembly, a 1 litre, low-form beaker, 149±11 mm in height and having an inside diameter of 106±9 mm for the immersion fluid, a thermostatic arrangement for heating the fluid between 35° C. and 39° C., and a device for raising and lowering the basket in the immersion fluid at a constant frequency rate between 29 and 32 cycles per minute, through a distance of 55±2 mm. The volume of the fluid in the vessel is such that at the highest point of the upward stroke the wire mesh remains at least 15 mm below the surface of the fluid, and descends to not less than 25 mm from the bottom of the vessel on the downward stroke. At no time should the top of the basket-rack assembly become submerged. The time required for the upward stroke is equal to the time required for the downward stroke, and the change in stroke direction is a smooth transition, rather than an abrupt reversal of motion. The basket-rack assembly moves vertically along its axis. There is no appreciable horizontal motion or movement of the axis from the vertical.

Basket-rack assembly. The basket-rack assembly consists of 6 open-ended transparent tubes, each 77.5±2.5 mm long and having an inside diameter of 21.85±1.15 mm and a wall 1.9±0.9 mm thick; the tubes are held in a vertical position by 2 plates, each 90±2 mm in diameter and 6.75±1.75 mm in thickness, with 6 holes, each 24±2 mm in diameter, equidistant from the centre of the plate and equally spaced from one another. Attached to the under surface of the lower plate is a woven stainless steel wire cloth, which has a plain square weave with 2.0±0.2 mm mesh apertures and with a wire diameter of 0.615±0.045 mm. The parts of the apparatus are assembled and rigidly held by means of 3 bolts passing through the 2 plates. A suitable means is provided to suspend the basket-rack assembly from the raising and lowering device using a point on its axis.

The design of the basket-rack assembly may be varied somewhat provided the specifications for the glass tubes and the screen mesh size are maintained. The basket-rack assembly conforms to the dimensions shown in FIG. 2.9.1.-1.

Discs. The use of discs is permitted only where specified or allowed. Each tube is provided with a cylindrical disc 9.5±0.15 mm thick and 20.7±0.15 mm in diameter. The disc is made of a suitable, transparent plastic material having a specific gravity of 1.18-1.20. 5 parallel 2±0.1 mm holes extend between the ends of the cylinder. One of the holes is centered on the cylindrical axis. The other holes are centered 6±0.2 mm from the axis on imaginary lines perpendicular to the axis and parallel to each other. 4 identical trapezoidal-shaped planes are cut into the wall of the cylinder, nearly perpendicular to the ends of the cylinder. The trapezoidal shape is symmetrical; its parallel sides coincide with the ends of the cylinder and are parallel to an imaginary line connecting the centres of 2 adjacent holes 6 mm from the cylindrical axis. The parallel side of the trapezoid on the bottom of the cylinder has a length of 1.6±0.1 mm and its bottom edges lie at a depth of ▶ 1.5 mm to 1.81 ◀ mm from the cylinder's circumference. The parallel side of the trapezoid on the top of the cylinder has a length of 9.4±0.2 mm and its centre lies at a depth of 2.6±0.1 mm from the cylinder's circumference. All surfaces of the disc are smooth.

If the use of discs is specified, add a disc to each tube and operate the apparatus as directed under Procedure. The discs conform to the dimensions shown in FIG. 2.9.1.-1. The use of automatic detection employing modified discs is permitted where the use of discs is specified or allowed. Such discs must comply with the requirements of density and dimension given in this chapter.

Procedure. One dosage unit is placed in each of the 6 tubes of the basket and, if prescribed, a disc is added. The apparatus is operated using the specified medium, maintained at 37±2° C., as the immersion fluid. At the end of the specified time, the basket is lifted from the fluid and the dosage units observed. If 1 or 2 dosage units fail to disintegrate, repeat the test on 12 additional dosage units. The requirements of the test are met if not less than 16 of the 18 dosage units tested have disintegrated.

Example 14

The following example describes compositions that did not produce tablets with satisfactory properties. In the following compositions, 10 g of Neusilin substituted with 10 g of Fujicalin.

Composition 309

| Name of ingredient | Amount (%) |
|---|---|
| Krill Calgary (1 mm) | 66 |
| Neusilin UFL2 | 6 |
| Kollidon 30 | 3 |
| Fujicalin | 10 |
| Avicel PH102 | 10 |
| Ac-Di-Sol | 5 |

Composition 313

| Name of ingredient | Amount (%) |
|---|---|
| Krill Calgary (1 mm) | 68 |
| Neusilin UFL2 | 6 |
| Kollidon 30 | 1 |
| Fujicalin | 10 |
| Avicel PH102 | 10 |
| Ac-Di-Sol | 5 |

Composition 321

| Name of ingredient | Amount (%) |
|---|---|
| Krill Calgary (1 mm) | 65 |
| Neusilin UFL2 | 6 |
| Klucel EF | 4 |
| Fujicalin | 10 |
| Avicel PH102 | 10 |
| Ac-Di-Sol | 5 |

Composition 323

| Name of ingredient | Amount (%) |
| --- | --- |
| Krill Calgary (1 mm) | 67 |
| Neusilin UFL2 | 6 |
| Klucel EF | 2 |
| Fujicalin | 10 |
| Avicel PH102 | 10 |
| Ac-Di-Sol | 5 |

In the following compositions, 10 g of Avicel is substituted with 10 g of Fujicalin.

Composition 409

| Name of ingredient | Amount (%) |
| --- | --- |
| Krill Calgary (1 mm) | 66 |
| Neusilin UFL2 | 16 |
| Kollidon 30 | 3 |
| Fujicalin | 10 |
| Ac-Di-Sol | 5 |

Composition 413

| Name of ingredient | Amount (%) |
| --- | --- |
| Krill Calgary (1 mm) | 68 |
| Neusilin UFL2 | 16 |
| Kollidon 30 | 1 |
| Fujicalin | 10 |
| Ac-Di-Sol | 5 |

Composition 421

| Name of ingredient | Amount (%) |
| --- | --- |
| Krill Calgary (1 mm) | 65 |
| Neusilin UFL2 | 16 |
| Klucel EF | 4 |
| Fujicalin | 10 |
| Ac-Di-Sol | 5 |

Composition 423

| Name of ingredient | Amount (%) |
| --- | --- |
| Krill Calgary (1 mm) | 67 |
| Neusilin UFL2 | 16 |
| Klucel EF | 2 |
| Fujicalin | 10 |
| Ac-Di-Sol | 5 |

The hardness of the tablets was almost independent of the compaction pressure. Maximum hardness is given in the table. As can be seen the tablets with Avicel showed somewhat better tablet strength than the others, but all compositions failed, as capping and lamination was observed by all formulations.

| Composition | Hardness (N) |
| --- | --- |
| 309 | 26 |
| 313 | 23 |
| 321 | 30 |
| 323 | 20 |
| 409 | 49 |
| 413 | 59 |
| 421 | 51 |
| 423 | 49 |

Example 15

Powder characterization. Krill powder is characterised as a powder containing large amounts of fat or fatty acids (40%). Both qualities of the substance show poor flow properties (Table 1).

|  | Carr index (%) | Loss on drying (%) |
| --- | --- | --- |
| Calgary | 17 | 5 |
| Powder | 18 | 4.5 |

Typical problems related to tabletting of krill powder are thus:
a) Large mass variation of tablets due to poor flow properties;
b) Low tablet strength due to high amount of fats

| Name of ingredients | Containing | Function | Quality |
| --- | --- | --- | --- |
| Krill Calgary (Aker BioMarine) |  | Active ingredient |  |
| Krill powder (Aker BioMarine) |  | Active ingredient |  |
| Neusilin UFL2 (Fuji chemical) | Magnesium aluminometasilicate | Adsorption agent | Ph. Jap. curr. ed. |
| Fujicalin (Fuji chemical) | Anhydrous dibasic calcium phosphate | Adsorption agent, binder | Ph. Jap. curr. ed. |
| Klucel EF (Hercules) | Hydroxypropyl cellulose (HPC) | Binding agent | Ph. Eur. curr. ed. |

| Name of ingredients | Containing | Function | Quality |
|---|---|---|---|
| Kollidon 30 (BASF) | Polyvinyl pyrrolidone | Binding agent | Ph. Eur. curr. ed. |
| Kollidon CL (BASF) | Polyvinyl pyrrolidone (cross linked) | Disintegrant | Ph. Eur. curr. ed. |
| Ac-Di-Sol (FMC) | Croscaramellose sodium | Disintegrant | Ph. Eur. curr. ed. |
| Avicel PH102 (FMC) | Microcrystalline cellulose | Binding agent | Ph. Eur. curr. ed. |
| Ethanol (96%) | | Solvent | Ph. Eur. curr. ed. |
| Purified water | | Solvent | Ph. Eur. curr. ed. |

Direct compression. Direct compression was performed initially without a disintegration agent. It was not necessary to add lubricant, as the fat itself had this function. Only some of the best batches were further characterized (tablet strength), as the challenge was to avoid capping and reach a high pay load. The ingredients were mixed by hand in a vessel and tabletted using a single punch tabletting machine (DIAF, Denmark). Due to limited amounts of API, the typical batch size was 15 g. Punch: Flat, 12 mm diameter.

The following table shows the results when standard excipients were tested. Typical problems related to poor binding properties (capping at higher pressure) and that oil was squeezed out during compression, was observed. Fujicalin was not acceptable as binder/adsorbing agent.

| Test no | Krill (%) | Avicel PH 101 (%) | Fujicalin (%) | Tabletting properties |
|---|---|---|---|---|
| 1 | 50 | 50 | | Oily, at high pressure the fat was pressed out |
| 3 | 50 | | 50 | At low pressure, acceptable tablets At high pressure, capping |
| 5 | 50 | 25 | 25 | Less capping than test 3 |

Fujicalin was then substituted with Neusilin. It has a large specific surface area and has good compression properties. A coarser quality of Avicel was also tested.

| Test no | Krill (%) | Avicel PH 101 (%) | Avicel PH 102 (%) | Neusilin (%) | Tabletting properties |
|---|---|---|---|---|---|
| 2 | 50 | | | 50 | At low pressure, acceptable tablets At high pressure, capping |
| 6 | 50 | 25 | | 25 | No capping observed, even at high pressure |
| 7 | 50 | | 25 | 25 | Same properties as test 6, better flow properties |

As a consequence of the above results, it was decided to use a mix of Avicel PH 102 and Neusilin as excipients. In the next step, the pay load was increased. As can be seen, the mix of 15% of both excipients gave the best results. Increasing the amount of krill to 80%, causes capping.

| Test no | Krill (%) | Avicel PH 102 (%) | Neusilin (%) | Tabletting properties |
|---|---|---|---|---|
| 8 | 70 | 15 | 15 | Hard tablets, no capping |
| 9 | 70 | 20 | 10 | Hard tablets, capping |
| 10 | 70 | 10 | 20 | Softer tablets than test 9, capping |
| 4 | 80 | | 20 | At low pressure, acceptable tablets At high pressure, capping |
| 11 | 80 | 10 | 10 | Capping |

Disintegrant. As a conclusion of the experiments without a disintegrant, it was decided to add disintegrant to the composition in test 8. A high amount of disintegrant was necessary, and Ac-Di-Sol proved best.

| Test no | Krill (%) | Avicel PH 102 (%) | Neusilin (%) | Ac-Di-Sol (%) | Kollidon CL (%) | Tabletting properties |
|---|---|---|---|---|---|---|
| 14 | 69 | 15 | 15 | 1 | | Does not disintegrate |
| 15 | 67 | 14 | 14 | 5 | | Disintegrates slowly |
| 16 | 67 | 14 | 14 | | 5 | Does not disintegrate |

The DC tests showed that acceptable tables could be produced, but the tablets strength of all compositions was below 50 N. The disintegration properties were not acceptable. DC was abandoned, and wet granulation had to be tested.

Wet granulation. By wet granulation, the binding properties of the powder can be improved. The adsorption agent was added to the powder blend prior to granulation and the disintegrant was added to the outer phase.

Procedure. Granulation liquid was made by dissolving the binder in the solvent. Krill Calgary was before blending forced through a 25 mesh screen. Krill was blended with Neusilin UFL2 and wetted with the granulation liquid. The wet mass was forced through a 25 mesh screen. The granules were dried at 40° C. for 12 hours and passed through a 18 mesh screen. The granulation liquid was made as 20% PVP and 10% HPC solutions. After adding the prescribed amount of dissolved binder, water or ethanol was added q.s. to obtain the desired consistency.

Tabletting. The dry granules were mixed with the other excipients (outer phase), and tablets were compacted using a single punch tablet press (DIAF). Tablet hardness was measured on a fracture resistant tester.

Inner phase screening. The following parameters were screened at different levels.

| Parameter | Level | |
|---|---|---|
| Krill | Calgary | Powder |
| Neusilin UFL2 | 16% | 9% |
| Binder | PVP 30 (4%) | PVP 30 (1%) |
|  | HPC (5%) | HPC (2%) |
| Granulation liquid | Water | Ethanol |

Combining all parameters gives a matrix with 32 experiments. The experiments which included krill powder and HPC were not performed. The inner phase was mixed with an outer phase according to the following table and tablets were compacted.

| Name of ingredient | Amount (g) |
|---|---|
| Inner phase | 8 |
| Neusilin | 1 |
| Avicel PH 102 | 1 |
| Ac-Di-Sol | 0.5 |

Complete composition

| | Inner phase no | | | | | | | | | | | | | | | |
|---|---|---|---|---|---|---|---|---|---|---|---|---|---|---|---|---|
| Ingredient | 1 | 3 | 5 | 7 | 9 | 10 | 13 | 14 | 17 | 18 | 19 | 20 | 21 | 22 | 23 | 24 |
| Calgary | 40 | 40 | 40 | 40 | 40 | 40 | 40 | 40 | 40 | 40 | 40 | 40 | 40 | 40 | 40 | 40 |
| Neusilin | 8 | 8 | 8 | 8 | 4 | 4 | 4 | 4 | 8 | 8 | 8 | 8 | 4 | 4 | 4 | 4 |
| PVP 30 | 2 | 0.5 | 2 | 0.5 | 2 | 2 | 0.5 | 0.5 | | | | | | | | |
| HPC | | | | | | | | | 2.5 | 2.5 | 1 | 1 | 2.5 | 2.5 | 1 | 1 |
| Gran. Liq. | W | W | E | E | W | E | W | E | W | E | W | E | W | E | W | E |
| Crushing str. (N) | 76 | 78 | 60 | 49 | 52 | 45 | 35 | 41 | 98 | 63 | 89 | 50 | 56 | 52 | 47 | 45 |

Amounts of inner phase (g) using Krill Calgary

The crushing strength depicted in the table above refers to tablets consisting of the inner phase mixed with outer phase. Water as granulation liquid gave harder tablets compared to ethanol. For the subsequent trials water is the preferred granulating liquid. It is difficult to interpret the effect of the binder, but it seems that the binders (both type and amount) have less influence on tablet strength. Reducing the amount of Neusilin seems to give tablets with lower crushing strength.

| | Inner phase no | | | | | | | |
|---|---|---|---|---|---|---|---|---|
| Ingredient | 2 | 4 | 6 | 8 | 11 | 12 | 15 | 16 |
| Powder | 40 | 40 | 40 | 40 | 40 | 40 | 40 | 40 |
| Neusilin | 8 | 8 | 8 | 8 | 4 | 4 | 4 | 4 |
| PVP 30 | 2 | 0.5 | 2 | 0.5 | 2 | 2 | 0.5 | 0.5 |
| HPC | | | | | | | | |
| Gran. Liq. | W | W | E | E | W | E | W | E |

Amounts of inner phase (g) using Krill Powder

Krill powder all gave granules with poor flow properties (Table 9). Additionally the tablets showed capping and were softer. Krill powder was abandoned for the subsequent experiments.

Outer phase. As one goal was to increase the pay load of krill, it was desirable to reduce the amount of excipients. The inner phase (experiments 9, 13, 21, 23) were used for the optimization of the outer phase. The same ingredients as tested in the direct compression experiments were added as the outer phase (see following table).

| Name of ingredient | Outer phase 1 | Outer phase 3 | Outer phase 4 | Outer phase 5 |
|---|---|---|---|---|
| Inner phase | 8 | 8 | 8 | 8 |
| Neusilin | 1 | | 1 | 0.7 |
| Avicel PH 102 | 1 | 1 | | 0.7 |
| Fujicalin | | 1 | 1 | 0.7 |
| Ac-Di-Sol | 0.5 | 0.5 | 0.5 | 0.5 |

Complete compositions (g) of different outer phases

The crushing strength was measured on the different compositions (following table). Neither of the compositions showed acceptable crushing strength. However, completely removing Neusilin in the outer phase seemed to even worsen the effect. The amount of Neusilin in the inner phase had to be increased.

| Inner phase no | Outer phase 1 | Outer phase 3 | Outer phase 4 | Outer phase 5 |
|---|---|---|---|---|
| 9 | 52 | 26 | 34 | 38 |
| 13 | 35 | 23 | 49 | 45 |
| 21 | 56 | 30 | 51 | 59 |
| 23 | 47 | 20 | 49 | 37 |

Crushing strength (N) using different outer phases

Optimization. The amount of Neusilin in the inner phase was increased compared to the initial experiments and at the same time the amount of Neusilin in the outer phase was reduced (see following tables).

| | Inner phase no | | | |
|---|---|---|---|---|
| Ingredient | 25 | 26 | 27 | 28 |
| Calgary | 40 | 40 | 40 | 40 |
| Neusilin | 12 | 12 | 10 | 10 |
| PVP 30 | 2 | | 2 | |

|  | Inner phase no | | | |
|---|---|---|---|---|
| Ingredient | 25 | 26 | 27 | 28 |
| HPC |  |  | 2 |  | 2 |
| Gran. Liq. | W | W | W | W |

Amounts of inner phase (g) using Krill Calgary

| Name of ingredient | Outer phase 1 | Outer phase 6 | Outer phase 7 | Outer phase 9 |
|---|---|---|---|---|
| Inner phase | 8 | 8 | 8 | 8 |
| Neusilin | 1 |  | 1 | 0.5 |
| Avicel PH 102 | 1 | 1 |  |  |
| Fujicalin |  |  |  |  |
| Ac-Di-Sol | 0.5 | 0.5 | 0.5 | 0.5 |

Complete compositions (g) of different outer phases

The crushing strength was measured on the different compositions (following table). Increasing the compaction pressure caused harder tablets. Capping could be observed by a high pressure. For the composition containing outer phase 9 (reduced Neusilin and no Avicel), capping was observed even at lower compaction pressure. Substituting Neusilin with Avicel also seemed to decrease crushing strength.

| Inner phase no | Outer phase 1 | Outer phase 6 | Outer phase 7 | Outer phase 9 |
|---|---|---|---|---|
| 25 | 120 | 80 | 110 | 70 |
| 26 | 120 | 70 | 90 | 70 |

Crushing strength (N) using different outer phases

Further optimization was done by reducing the amount of Neusilin in the inner phase (inner phase no 27 and 28).

| Name of ingredient | Outer phase 7 | Outer phase 8 |
|---|---|---|
| Inner base | 8 | 8 |
| Neusilin | 1 | 1.23 |
| Avicel PH 102 |  |  |
| Fujicalin |  |  |
| Ac-Di-Sol | 0.5 | 0.5 |

Complete compositions (g) of different outer phases

The crushing strength was measured on the different compositions (following table). Reducing the amount of Neusilin in the inner phase seemed to have a negative impact on tablet hardness. If the total amount of Neusilin was kept identical as in the previous experiments (inner phase 25 and 26, outer phase 7), the composition of outer phase 8 was generated. Comparing the data shows that substituting some of the Neusilin from the inner phase to the outer phase, gives a lower crushing strength. Additionally capping was observed at higher pressure.

| Inner phase no | Outer phase 7 | Outer phase 8 |
|---|---|---|
| 27 | 80 | 85 |
| 28 | 70 | 85 |

Crushing strength (N) using different outer phases

Rotary Press:
Tablets according to the complete composition:

| Inner phase: | 8 |
|---|---|
| Neusilin: | 1 |
| Ac.Di-Sol: | 0.5 | where inner phase consists of:

| Krill powder: | 40 |
|---|---|
| Neusilin: | 12 |
| HPC: | 2 | were compacted at a Fette 102i rotary press with typical technical data:
Dwell time with EU1/B-punches:
　Low speed: (5 rpm) 600 ms
　Maximum speed: (120 rpm) 25 ms
Tablets per time (8 stations):
　Low speed: (5 rpm) 2400 tab/h
　Maximum speed: (120 rpm) 57600 tab/h
At low speed capping was not observed, whereas at higher speeds capping occurred.

Tablets containing 63% of krill Calgary could successfully be compacted at a rotary press a low speed and at a single punch compactor. Increasing the amount of krill or decreasing the amount of Neusilin caused capping. It thus seems that the dwell time is critical.

Example 16

The following example describes coating of the tablets.

20.000 tablets were produced with the composition described below. As the tables are hydrophilic it was desirable to use ethanol as a coating solution. However as ethanol causes production challenges due to risk of explosion, water based coating solutions were tested: Sepifilm 050 and Sepisperse Dry (incl./5220 red). The products are dry powders (granules) and must be dispersed in water before use. The color intensity depends on the internal rate and total amount of the products. Typical production parameters using drum coaters are:
　Spraying rate: 7-15 g/min/kg
　Atomizing pressure: 2-3 bar
　Inlet temp.: 60-70° C.
　Outlet temp.: 44-47° C.
　Core temperature: 38-43° C.
　Spraying time (3% weight gain): 1-1.5 h A Uniglatt equipped with a bottom spray unit was used for the experiments. The principle is a fluid bed process equipped with a Wurster-column. As the coating principle differs from drum coating, the parameters were held as close to the recommended where possible. In order to avoid sticking, the spraying rate was kept at a low level. A core temperature of 40° C. is achieved using the following process parameters:
  Batch size: 400 g
  Spraying rate: 20 r.u. (Ismatec pump), corresponding to 4 mL/min
  Atomizing pressure: 2 bar
  Inlet temp.: 55-60° C.
  Outlet temp.: 44-47° C.
  Core temperature: 40° C.
Tablet Composition:

|   |   |   |
|---|---|---|
| Krill powder | 300 |   |
| Neusilin UFL2 | 140 |   |
| Klucel EF | 15 |   |
| Ac-Di-Sol | 25 |   |

Method of Manufacture:
Granulation:

| I | Krill calgary | 740 |
|---|---|---|
| II | Neusilin UFL2 | 220 |
| III | 5% Klucel EF800 |   |
| IV | Dem. vann | q.s. |

III is made by dissolving 40 g Klucel EF in 760 g demineralized vann. Agiatate until there are no visible lumps.

I is forced through a 18 mesh screen an blended in a high shear mixer with II until a uniform blend is achieved. The mix is wetted with III during mixing, and IV is added until the desired consistence is obtained. Thereafter the wet mass is mixed at high speed (with chopper) until visible granules are obtained. The moist granules are dried at shelves at 40° C. over night in a tray drier.

After drying, the granules are forced through a 16 mesh screen. Loss on drying is measured.
End Mixing:

| I-III | Granulation | 842 |
|---|---|---|
| V | Neusilin UFL2 | 105 |
| VI | Ac-Di-Sol | 53 |

The granulation (I-III) is mixed with V and VI in a high shear mixer until a uniform blend is achieved.
Tabletting:
Tablets are compacted using a rotary press at low speed gaining tablets with a minimum hardness of 100N. Punch: Oblong, biconvex.
Tablet Characterization:
Friability. The friability was measured using a Roche friabulator at 25 rpm for 15 min. Initial weight: 7.534 g (10 tablets); Final weight: 7.515 g (10 tablets); Friability: 0.25%. Friability must not exceed 0.3%, and should be as low as 0.1%. The tablet core had no visible damages.

Crushing strength. The mechanical strength was determined using a fracture resistant tester. As the table cores were oblong, the test was performed both in the longitudinal and latitude direction:

| Longitude (N) | 95 | 110 | 98 | 108 | 115 | 101 | 120 | 111 | 107 | 104 |
|---|---|---|---|---|---|---|---|---|---|---|
| Latitude (N) | 96 | 112 | 85 | 104 | 109 | 87 | 112 | 117 | 77 | 87 |

Conclusion—tablet cores. The crushing strength is acceptable. The friability is somewhat high, but is dependent on the sharp edges of the cores. The cores can however be coated.

Experiment 1

Coating Composition

Sepifilm 050: 100 g
Demineralized water: 900 g

| Spraying time | Weight coating solution | Tablet weight | Number of tablets. | Average weight | Weight increase |
|---|---|---|---|---|---|
| Start |   | 74.4 g | 100 | 0.744 g |   |
| 11 min | 1380 g | 7.41 g | 10 | 0.741 g | −0.4% |
| 71 min | 1200 g | 7.78 g | 10 | 0.778 g | 4.8% |
| 109 min | 1025 g | 79.8 g | 100 | 0.798 g | 7.3% |

A spraying time of 45 min seems to cause a weight gain of 3%. The mass variation of the tablets is too large that only 10 tables could be check weighted. 100 tablets should be used for this subsequent control.

Experiment 2

Coating Composition

Sepifilm 050: 60 g
Sepisperse Dry: 40 g
Demineralized water: 900 g

| Spraying time | Tablet weight | Number of tablets | Average weight | Weight increase |
|---|---|---|---|---|
| Start | 74.4 g | 100 | 0.744 g |   |
| 30 min | 75.3 g | 100 | 0.753 g | 0.7% |
| 60 min | 76.7 g | 100 | 0.767 g | 3.1% |

The composition of the coating dispersion caused a less weight increase per time unit. The film cracked at the edges of the cores. Additionally there were technical problems during the coating. The experiment was repeated and additionally vanilin was added as a flavoring agent.

Experiment 3

Coating Composition

Sepifilm 050: 60 g
Sepisperse Dry: 40 g
Vanilin: 20 g
Demineralized water: 900 g

| Spraying time | Tablet weight | Number of tablets | Average weight | Weight increase |
|---|---|---|---|---|
| Start | 74.4 g | 100 | 0.744 g |   |
| 30 min | 76.2 g | 100 | 0.762 g | 2.4% |
| 60 min | 77.4 g | 100 | 0.773 g | 3.9% |

The coating dispersion contains 11.8% dry substance. The dispersion is very viscous. A less vicious dispersion is desirable.

Experiment 4

Coating Composition

Sepifilm 050: 60 g
Sepisperse Dry: 40 g
Vanilin: 20 g
Demineralized water: 1180 g

| Spraying time | Tablet weight | Number of tablets | Average weight | Weight increase |
|---|---|---|---|---|
| Start | 74.4 g | 100 | 0.744 g | |
| 30 min | 75.6 g | 100 | 0.756 g | 1.6% |
| 60 min | 77.0 g | 100 | 0.770 g | 3.5% |

The coating dispersion contained 9.2% dry substance. The viscosity was lower, and did not cause any problems as sticking of the nozzles. A spraying time of about 1 h also seemed to be adequate to achieve a weight gain of about 3%.

CONCLUSION

The process parameters are within acceptable limits. The spraying rate is not too high, and sticking is not observed. The film has a tendency to crack at the edges of the tablets. This can be overcome by: a) Avoiding sharp edges of the tablets, use more convex punches; and b) Avoid cracking during compaction.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

The invention claimed is:

1. A solid dosage form comprising an active ingredient in a concentration of greater than about 40% by weight of said dosage form, wherein said active ingredient is a krill protein-phospholipid composition comprising protein in a concentration of about 30% to about 50% by weight of said active ingredient and fat in a concentration of about 50% to about 75% by weight of said active ingredient, wherein said fat comprises phospholipids in a concentration of about 35% to about 60% by weight of said fat; and an aluminometasilicate adsorption agent in a concentration of from about 18% to about 30% by weight of said dosage form; wherein said dosage form has a hardness of greater than about 60 N.

2. The solid dosage form of claim 1, wherein said active ingredient further comprises astaxanthin.

3. The solid dosage form of claim 2, wherein said active ingredient comprises from about 1 to about 200 mg/kg astaxanthin.

4. The solid dosage form of claim 1, wherein said fat comprises omega-3 fatty acids residues in a concentration of from about 10% to about 35% by weight of said fat.

5. The solid dosage form of claim 1, wherein said phospholipids comprise phosphatidylcholine in a concentration of greater than about 65% by weight of said phospholipids.

6. The solid dosage form of claim 1, wherein said phospholipids comprise alkylacylphosphatidylcholine in a concentration of from about 2% to about 10% by weight of said phospholipids.

7. The solid dosage form of claim 1, said adsorption agent is provided in a concentration of from about 18% to about 25% by weight of said dosage form.

8. The solid dosage form of claim 1, further comprising a binding agent in a concentration of from about 8% to about 15% by weight of said dosage form.

9. The solid dosage form of claim 1, further comprising a disintegrant in a concentration of from about 2% to about 8% by weight of said dosage form.

10. The solid dosage form of claim 1, wherein said solid dosage form comprises omega-3 fatty residues in a concentration of about 2.5% to 15% by weight of said dosage form.

11. The solid dosage form of claim 1, wherein said fat comprises triglycerides in a concentration of from about 40% to about 65% by weight of said fat.

12. The solid dosage form of claim 1, wherein said protein comprises from about 8% to about 14% leucine by weight of said protein.

13. The solid dosage form of claim 1, wherein the dissolution of the dosage form in a medium containing demineralized water as a solvent is greater than 75 percent at about 10 minutes where the tablet is raised and lowered in said solvent at a constant frequency rate between 29 and 32 cycles per minute, through a distance of 55±2 mm.

14. The solid dosage form of claim 1, wherein said dosage form is a tablet.

15. A solid dosage form comprising an active ingredient in a concentration of about 55% to about 65% by weight of said dosage form, wherein said active ingredient is a krill protein-phospholipid composition comprising protein in a concentration of about 30% to about 50% by weight of said active ingredient and fat in a concentration of about 50% to about 75% by weight of said active ingredient, wherein said fat comprises phospholipids in a concentration of about 35% to about 60% by weight of said fat; an aluminometasilicate adsorption agent in a concentration of about 18% to about 25% by weight of said dosage form, a binding agent in a concentration of about 8% to about 15% by weight of said dosage form; wherein said dosage form has a hardness of greater than about 60 N.

16. A process for the preparation of the solid dosage form of claim 1 comprising:
 wet granulating an inner phase comprising an active ingredient, wherein said active ingredient is a krill protein-phospholipid composition comprising protein in a concentration of about 30% to about 50% by weight of said active ingredient and fat in a concentration of about 50% to about 75% by weight of said active ingredient, wherein said fat comprises phospholipids in a concentration of about 35% to about 60% by weight of said fat, and an aluminometasilicate adsorption agent;
 forming an outer phase comprising one or more pharmaceutically acceptable excipients;
 mixing said outer phase with said inner phase to form a compressible mixture; and
 compressing said compressible mixture to form a tablet.

* * * * *